US008147833B2

(12) United States Patent
Schenk et al.

(10) Patent No.: US 8,147,833 B2
(45) Date of Patent: Apr. 3, 2012

(54) PREVENTION AND TREATMENT OF SYNUCLEINOPATHIC AND AMYLOIDOGENIC DISEASE

(75) Inventors: Dale B. Schenk, Burlingame, CA (US); Eliezer Masliah, San Diego, CA (US); Manuel J. Buttini, Emeryville, CA (US); Tamie J. Chilcote, San Francisco, CA (US); Edward Rockenstein, Chula Vista, CA (US); Kate Dora Games, Belmont, CA (US)

(73) Assignees: Neotope Biosciences Limited, Dublin (IE); The Regents of the University of California, Oakland, CA (US)

( * ) Notice: Subject to any disclaimer, the term of this patent is extended or adjusted under 35 U.S.C. 154(b) by 0 days.

(21) Appl. No.: 12/528,439

(22) PCT Filed: Feb. 22, 2008

(86) PCT No.: PCT/US2008/002392
§ 371 (c)(1),
(2), (4) Date: Dec. 7, 2009

(87) PCT Pub. No.: WO2008/103472
PCT Pub. Date: Aug. 28, 2008

(65) Prior Publication Data
US 2010/0086545 A1 Apr. 8, 2010

Related U.S. Application Data

(63) Continuation-in-part of application No. 11/697,646, filed on Apr. 6, 2007, which is a continuation-in-part of application No. 11/710,248, filed on Feb. 23, 2007.

(60) Provisional application No. 60/984,721, filed on Nov. 1, 2007.

(51) Int. Cl.
*A61K 39/395* (2006.01)
(52) U.S. Cl. ................. 424/133.1; 424/139.1; 424/141.1
(58) Field of Classification Search .................. None
See application file for complete search history.

(56) References Cited

U.S. PATENT DOCUMENTS

| 4,883,666 | A  | 11/1989 | Sabel et al. |
| 5,576,184 | A  | 11/1996 | Better et al. |
| 5,583,112 | A  | 12/1996 | Kensil et al. |
| 5,589,154 | A  | 12/1996 | Anderson |
| 5,604,102 | A  | 2/1997  | McConlogue et al. |
| 5,753,624 | A  | 5/1998  | McMichael |
| 5,780,587 | A  | 7/1998  | Potter |
| 5,807,741 | A  | 9/1998  | Brown et al. |
| 5,851,996 | A  | 12/1998 | Kline |
| 5,958,883 | A  | 9/1999  | Snow |
| 6,093,406 | A  | 7/2000  | Alving et al. |
| 6,172,122 | B1 | 1/2001  | Lawate et al. |
| 6,416,947 | B1 | 7/2002  | Baiasubramanian et al. |
| 6,504,080 | B1 | 1/2003  | Van Der Putten |
| 6,710,226 | B1 | 3/2004  | Schenk |
| 6,743,427 | B1 | 6/2004  | Schenk |
| 6,761,888 | B1 | 7/2004  | Schenk |
| 6,780,971 | B2 | 8/2004  | Wolozin et al. |
| 6,787,138 | B1 | 9/2004  | Schenk |
| 6,787,139 | B1 | 9/2004  | Schenk |
| 6,787,140 | B1 | 9/2004  | Schenk |
| 6,787,143 | B1 | 9/2004  | Schenk |
| 6,787,144 | B1 | 9/2004  | Schenk |
| 6,787,523 | B1 | 9/2004  | Schenk |
| 6,858,704 | B2 | 2/2005  | Kim |
| 6,866,849 | B2 | 3/2005  | Schenk |
| 6,866,850 | B2 | 3/2005  | Schenk |
| 6,875,434 | B1 | 4/2005  | Schenk |
| 6,890,535 | B1 | 5/2005  | Schenk |
| 6,923,964 | B1 | 8/2005  | Schenk |
| 6,946,135 | B2 | 9/2005  | Schenk et al. |
| 6,972,127 | B2 | 12/2005 | Schenk |
| 7,014,855 | B2 | 3/2006  | Schenk |
| 7,060,464 | B2 | 6/2006  | Kim |
| 7,138,255 | B2 | 11/2006 | Vodyanoy et al. |
| 7,306,945 | B2 | 12/2007 | Chilcote et al. |
| 7,358,331 | B2 | 4/2008  | Chilcote et al. |
| 7,479,482 | B2 | 1/2009  | Frangione et al. |
| 7,674,599 | B2 | 3/2010  | Chilcote |
| 7,727,957 | B2 | 6/2010  | Schenk |
| 7,910,333 | B2 | 3/2011  | Chilcote et al. |
| 7,964,192 | B1 | 6/2011  | Schenk |
| 2002/0094335 | A1 | 7/2002 | Chalifour et al. |
| 2002/0151464 | A1 | 10/2002 | Wolozin et al. |
| 2002/0160394 | A1 | 10/2002 | Wu |
| 2002/0187157 | A1 | 12/2002 | Jensen et al. |
| 2002/0197258 | A1 | 12/2002 | Ghanbari et al. |
| 2003/0086938 | A1 | 5/2003 | Jensen et al. |

(Continued)

FOREIGN PATENT DOCUMENTS

EP 0 613 007 A2 8/1994
(Continued)

OTHER PUBLICATIONS

U.S. Appl. No. 60/423,012, filed Nov. 1, 2002, Schenk et al.
Bradbury "Immunotherapy for Parkinson's disease: a developing therapeutic strategy" *News and Comment* (2005) DDT. 10(16): 1075-1076.
Choi, et al., "Fine epitope mapping of monoclonal antibodies specific to human a-synuclein." *Neuroscience Letters* 397 (2006) 53-58.
EP 08725981 Supplementary European Search Report completed Sep. 8, 2010.
Harlow et al., eds., *Antibodies, A Laboratory Manual*, Cold Spring Harbor Laboratory p. 71-82 (1988).
Jendroska et al., "Amyloid β-Peptide and the Dementia of Parkinson's Disease," *Movement Disorders*, 11(6):647-653 (1996).

(Continued)

*Primary Examiner* — Daniel E Kolker
(74) *Attorney, Agent, or Firm* — Alston & Bird LLP

(57) ABSTRACT

The invention provides improved agents and methods for treatment of diseases associated with synucleinopathic diseases, including Lewy bodies of alpha-synuclein in the brain of a patient. Such methods entail administering agents that induce a beneficial immunogenic response against the Lewy body. The methods are particularly useful for prophylactic and therapeutic treatment of Parkinson's disease.

4 Claims, 17 Drawing Sheets

U.S. PATENT DOCUMENTS

| | | |
|---|---|---|
| 2003/0157117 A1 | 8/2003 | Rasmussen et al. |
| 2003/0165496 A1 | 9/2003 | Basi et al. |
| 2003/0166558 A1 | 9/2003 | Frangione et al. |
| 2003/0166588 A1 | 9/2003 | Iversen et al. |
| 2003/0185827 A1 | 10/2003 | Rodriguez et al. |
| 2004/0136993 A1 | 7/2004 | Schenk et al. |
| 2004/0137523 A1 | 7/2004 | Vodyanoy et al. |
| 2004/0146521 A1 | 7/2004 | Schenk et al. |
| 2004/0197831 A1 | 10/2004 | Weksler et al. |
| 2005/0037013 A1 | 2/2005 | Schenk et al. |
| 2005/0123544 A1 | 6/2005 | Schenk et al. |
| 2005/0176078 A1 | 8/2005 | Allsop et al. |
| 2005/0196818 A1 | 9/2005 | Chilcote et al. |
| 2005/0198694 A1 | 9/2005 | Chilcote et al. |
| 2005/0203010 A1 | 9/2005 | Kim |
| 2005/0255113 A1 | 11/2005 | Huston et al. |
| 2006/0058233 A1 | 3/2006 | Schenk et al. |
| 2006/0259986 A1 | 11/2006 | Chilcote et al. |
| 2008/0014194 A1 | 1/2008 | Schenk et al. |
| 2008/0175838 A1 | 7/2008 | Schenk et al. |
| 2010/0086545 A1 | 4/2010 | Schenk |
| 2010/0203631 A1 | 8/2010 | Chilcote |
| 2011/0135660 A1 | 6/2011 | Schenk et al. |

FOREIGN PATENT DOCUMENTS

| | | |
|---|---|---|
| EP | 1 633 189 A2 | 3/2006 |
| WO | WO 91/16819 A1 | 11/1991 |
| WO | WO 95/06407 A1 | 3/1995 |
| WO | WO 99/06545 A2 | 2/1999 |
| WO | WO 99/06545 A3 | 2/1999 |
| WO | WO 99/27944 A1 | 6/1999 |
| WO | WO 99/40191 A1 | 8/1999 |
| WO | WO 99/50300 A1 | 10/1999 |
| WO | WO 99/60024 A1 | 11/1999 |
| WO | WO 00/18917 A2 | 4/2000 |
| WO | WO 00/18917 A3 | 4/2000 |
| WO | WO 00/20020 A2 | 4/2000 |
| WO | WO 00/72876 A2 | 12/2000 |
| WO | WO 00/72876 A3 | 12/2000 |
| WO | WO 00/72880 A2 | 12/2000 |
| WO | WO 00/72880 A3 | 12/2000 |
| WO | WO 01/06989 A2 | 2/2001 |
| WO | WO 01/06989 A3 | 2/2001 |
| WO | WO 01/53457 A2 | 7/2001 |
| WO | WO 01/53457 A3 | 7/2001 |
| WO | WO 01/60794 A2 | 8/2001 |
| WO | WO 01/60794 A3 | 8/2001 |
| WO | WO 02/03911 A2 | 1/2002 |
| WO | WO 03/000714 A2 | 1/2003 |
| WO | WO 03/000714 A3 | 1/2003 |
| WO | WO 03/045128 A2 | 6/2003 |
| WO | WO 03/045128 A3 | 6/2003 |
| WO | WO 2004/009625 A2 | 1/2004 |
| WO | WO 2004/009625 A3 | 1/2004 |
| WO | WO 2004/041067 A2 | 5/2004 |
| WO | WO 2004/041067 A3 | 5/2004 |
| WO | WO 2005/013889 A3 | 2/2005 |
| WO | WO 2005/047860 A2 | 5/2005 |
| WO | WO 2005/047860 A3 | 5/2005 |
| WO | WO 2006/020581 A2 | 2/2006 |
| WO | WO 2006/020581 A3 | 2/2006 |
| WO | WO 2006/045037 A2 | 4/2006 |
| WO | WO 2006/045037 A3 | 4/2006 |
| WO | WO 2007/011907 A2 | 1/2007 |
| WO | WO 2007/012061 A2 | 1/2007 |
| WO | WO 2007/012061 A3 | 1/2007 |
| WO | WO 2007/021255 A1 | 2/2007 |
| WO | WO 2008/103472 A2 | 8/2008 |
| WO | WO 2008/103472 A3 | 8/2008 |

OTHER PUBLICATIONS

Li et al., "Aggregation promoting C-terminal truncation of α-synuclein is a normal cellular process and is enhanced by the familial Parkinson's disease-linked mutations," *PNAS*, 102(6):2162-2167 (2005). Liu et al., "A Precipitating Role for Truncated α-Synuclein and the Proteasome in α-Synuclein Aggregation," *J. Biol. Chem.*, 280(24):22670-22678 (2005).

Miake et al., "Biochemical Characterization of the Core Structure of α-synuclein Filaments," *J. Biol. Chem.*, 277 (21): 19213-19219 (2002).
Murray et al., "Role of α-Synuclein Carboxy-Terminus on Fibril Formation in Vitro," *Biochemistry*, 42:8530-8540 (2003).
PCT/US03/34527 International Preliminary Examination Report issed May 24, 2004.
PCT/US05/28166 Search Report mailed Dec. 14, 2006.
PCT/US06/28273 International Preliminary Report on Patentability completed Aug. 6, 2009.
PCT/US90/28273 Written Opinion of International Searching Authority issued Sep. 24, 2007.
Serpell et al., "Fiber diffraction of synthetic α-synuclein Filaments shows amyloid-like cross-βconformation." *PNAS*, 97(9):4897-4902 (2000).
U.S. Appl. No. 11/894,772, filed Aug. 20, 2007, Schenk et al.
U.S. Appl. No. 11/894,744, filed Aug. 20, 2007, Schenk et al.
U.S. Appl. No. 11/894,605, filed Aug. 20, 2007, Schenk et al.
U.S. Appl. No. 11/841,996, filed Aug. 20, 2007, Schenk et al.
U.S. Appl. No. 11/710,248, filed Feb. 23, 2007, Schenk et al.
U.S. Appl. No. 11/660,015, filed Feb. 9, 2007, Schenk et al.
U.S. Appl. No. 10/850,570, filed May 19, 2004, Chilcote et al.
U.S. Appl. No. 60/518,140, filed Nov. 8, 2003, Chilcote et al.
U.S. Appl. No. 60/471,929, filed May 19, 2003, Chilcote et al.
Abbas et al., *Celluar and Molecular Immunology*, 522-523 (Elsevier Saunders) (5th Ed. Updated Ed., 2005).
Anderson et al., "Phosphorylation of SER-129 is the dominant pathological modification of alpha-synuclein in familial and sporadic Lewy body disease," *The Journal of Biological Chemistry*, 281:29739-29752 (2006).
Alves da Costa, "Recent Advances on α-Synuclein Cell Biology : Functions and Dysfunctions," *Current Molecular Medicines*, 3:17-24 (2003).
Bales et al., "Cholinergic dysfunction in a mouse model of Alzheimer disease is reversed by an anti-Aβantibody," *J. Clin. Invest.*, 116(3):825-832 (2006).
Bard et al., "Peripherally administered antibodies against amyloid β-peptide enter the central nervous system and reduce pathology in a mouse of Alzheimer disease," *Nature Medicine*, 6(8):916-919 (2000).
Bennett et al., "Degradation of α-Synuclein by Proteasome," *J. Biol. Chem.*, 274(48):33855-33858 (1999).
Bodles et al., "Toxicity of non-Aβ Component of Alzheimer's disease amyloid, and N-terminal fragments thereof, correlates to formation of β-sheet structure and fibrils," *Eur. J. Biochem.*, 267:2186-2194 (2000).
Brooks et al., "Synuclein proteins and Alzheimer's disease," *Trends Neurosci.*, 17(10):404-405 (1994).
Cao et al., "Development of an Alpha Synuclein Recombinant Protein as a Potential Candidate Against Parkinson's Disease," Program No. 594.3, Abstract Viewer/Itinerary Planner, Washington D.C.: Society for Neuroscience (2002).
Casadesus et al., "The Estrogen Myth; Potential Use of Gonadotropin-releasing hormone Agonists for Treatment of Alzheimer's Disease," *Drugs R&D*, 7(3):187-193 (2006).
Chang et al., "Adjuvant activity of incomplete Freund's adjuvant," *Advanced Drug Delivery Reviews*, 32:173-186 1998).
Chapman, "Model behavior," *Nature*, 408:915-916 (2000).
Chen et al., "Neurodegenerative Alzheimer-like pathology in PDAPP 717V→F transgenic mice," *Progress in Brain Research*, 117:327-337 (1998).
Chilcote et al., "Comparison of alpha-synuclein species in Lewy bodies and the soluble fraction of diffuse Lewy body disease brain," Database Biosis [Online] Biosciences Information Service, Phililadelphia, Pa, US (2003) Abstract only.
Clayton et al., "Synucleins in Synaptic Plasticity and Neurodegenerative Disorders," *J. Neurosci. Res.*, 58:120-129 (1999).
Clayton er al, "The synucleins: a family of protein involved in synaptic function, plasticity, neurodegeneration, and disease," *Trends Neurosci.*, 21(6):249-254 (1998).
Cleland et al., "Isomerization and Formulation Stability of the Vaccine Adjuvant QS-21," *J. of Pharm Sci.*, 85(1): 22-28 (1996).

Conway et al., "Acceleration of oligomerization, not fibrillization, is a shared property of both α-synuclein mutations linked to early-onset Parkinson's disease: Implications for pathogenesis and therapy," *PNAS*, 97(2):571-576 (2000).

Crowther et al., "Synthetic filaments assembled from C-terminally truncated a-synuclein," *FEBS Letters*, 436:309-312 (1998).

Culvenor et al., "Non-Aβ Component of Alzheimer's Disease Amyloid (NAC) Revisited, NAC and α-Synuclein are not Associated with Aβ Amyloid," *Am. J. Pathology*, 155(4):1173-1181 (1999).

De Lustig et al., "Peripheral markers and diagnostic criteria in Alzheimer's disease: Critical evaluations," *Rev. in Neurosci.*, 5:213-224 (1994).

Demattos et al., "Peripheral Anti Aβ Antibody Alters CNS And Plasma Aβ Clearance and Decreases Brain Aβ Burden in a Mouse Model of Alzheimer's Disease," published online before print Jul. 3, 2001 at 10.1073/pnas. 151261398; *PNAS*, 98(15):8850-8855 (2001).

Dictionary.com definition of "prophylactic", pp. 1-3 downloaded from internet Oct. 12, 2005.

Dictionary entry for "prophylactic", *Webster's New World Dictionary of American English*, 3rd College Edition, New York, p. 1078 (1988).

Di Monte et al., "Environmental Factors in Parkinson's Disease," *Neurotoxicology*, 23: 487-502 (2002).

Dixon, C. et al., "Alpha-Synuclein Targets the Plasma Membrane via the Secretory Pathway and Induces Toxicity in Yeast," *Genetics*, May 2005;170(1):47-59. Epub Mar. 2, 2005.

El-Agnaf et al., "α-Synuclein implicated in Parkinson's disease is present in extracellular biological fluids, including human plasma," *FASEB J.*, 17(3):1945-1947 (2003).

El-Agnaf et al., "α-Synuclein implicated in Parkinson's disease is present in extracellular biological fluids, including human plasma," *FASEB J. express artical 10.1096/fj.03-0098fje*, Published online Aug. 15, 2003. Abstract.

Elan, "Elan and AHP Provide an Update on the Phase 2A Clinical Trial on AN-1792," Press Release. (Jan. 18, 2002).

Elan, "Elan and Wyeth Provide Update on Status of Alzheimer's Collaboration," Press Release (Mar. 1, 2002).

Eliezer, D. et al., "Conformational Properties of Alpha-Synuclein in its Free and Lipid-associated States," *Journal of Molecular Biology*, 307(4):1061-1073 (2001).

Ellis et al., "α-Synuclein is Phosphorylated by Members of the Src Family of Protein-tyrosine Kinases," *J. Biol. Chem.*, 276(6):3879-3884 (2001).

Emadi, S. et al., "Inhibiting Aggregation of Alpha-Synuclein with Human Single Chain Antibody Fragments," *Biochemistry*, 43(10):2871-2878 (2004).

Esiri, "Is an effective immune intervention for Alzheimer's disease in prospect?", *Trends in Pharm, Sci.*, 22:2-3 (2001).

EP 04776059.0 European Supplementary Search Report completed Jun. 13, 2006.

EP 03783083.3 European Supplementary Search Report completed Oct. 10, 2008.

EP 05783732 European Supplementary Search Report completed Mar. 5, 2009.

EP 05814041.9 European Supplementary Search Report completed Oct. 29, 2008.

EP 06800177 European Supplementary Search Report completed Mar. 9, 2009.

Farrer, M.J., "Genetics of Parkinson disease: Paradigm shifts and future prospects," *Nat. Rev. Genet.*, 7:306-318 (2006).

Frenkel et al., "High affinity binding of monoclonal antibodies to the sequential epitope EFRH of β-amyloid peptide is essential for modulation of fibrillar aggregation," *J. of Neuroimmunology*, 95:136-142 (1999).

Frenkel et al., "Immunization against Alzheimer's β-amyloid plaques via EFRH phage administration," *PNAS*, 97:11455-11459 (2000).

Frenkel et al., "N-terminal EFRH sequence of Alzheimer's β-amyloid peptide represents the epitope of its anti-aggregating antibodies," *J. of Neuroimmunology*, 88:85-90 (1998).

Friedland, et al., "Neuroimaging of Vessel Amyloid in Alzheimer's Disease," in *Cerebrovascular Pathology in Alzheimer's Disease*, eds. de la Torre and Hachinski, New York Academy of Sciences, New York, New York, pp. 242-247 (1997).

Friedland et al., "Development of an anti-Aβ monoclonal antibody for in vivo imaging of amyloid angiopath in Alzheimer's disease," *Mol. Neurology*, 9:107-113 (1994).

Games et al., "Alzheimer-type neuropathology in transgenic mice overexpressing V717F β-amyloid precursor protein," *Nature*, 373(6514):523-527 (1995).

Games et al., "Prevention and Reduction of AD-type Pathology in PDAPP Mice Immunized with Aβ$_{1-42}$," *Annals of the New York Academy of Science*, 920:274-284 (2000).

Garzon, J. et al., "Transport of CSF antibodies to G-Alpha subunits across neural membranes requires binding to the target protein and protein kinase C activity," *Molecular Brain Research*, 65(2):151-166 (1999).

Giasson et al., "A Panel of Epitope-Specific Antibodies Detects Protein Domains Distributed Throughout Human α-Synuclein in Lewy Bodies of Parkinson's Disease," Journal of Neuroscience Research, 59:528-533 (2000).

Giasson et al., "Mutant and Wild Type Human α-Synucleins Assemble into Elongated Filaments with Distinct Morphologies in Vitro," *J. Biol. Chem.*, 274(12):7619-7622 (1999).

Goldsby et al., "Vaccines," Chapter 18 from *Immunology, 4th Edition*, W.H. Freeman and Company, New York, pp. 449-465 (2000).

Goldsteins et al., "Exposure of cryptic epitopes on transthyretin only in amypoid and in amyloidogenic mutants," *PNAS*, 96:3108-3113 (1999).

Grubeck-Loebenstein, et al., "Immunization with β-amyloid: could T-cell activation have a harmful effect?", *TINS*, 23:114 (2000).

Hamburger, A.W. et al., "Isolation and characterization of monoclonal antibodies reactive with endothelial cells," *Tissue & Cell*, 17(4): 451-459 (1985).

Hansen et al., "Chapter 14: Neurobiology of Disorders with Lewy Bodies," *Functional Neurobiology of Aging*, (Hof and Mobbs, Eds.) 173-182 (2001).

Harlow et al., eds., *Antibodies, A Laboratory Manual*, Cold Spring Harbor Laboratory, p. 98 (1988).

Hartman et al., "Treatment with an Amyloid-βAntibody Ameliorates Plaque Load, Learning Deficits, and Hippocampal Long-Term Potentiation in a Mouse Model of Alzheimer's Disease," *Journal of Neuroscience*, 25:6213-6220 (2005).

Hashimoto et al., "Alpha-synuclein in Lewy Body Disease and Alzheimer's Disease," *Brain Pathology*, 9:707-720 (1999).

Hashimoto et al., "β-synuclein inhibits [alpha]-synuclein aggregation: A possible role as an anti-Parkinsonian factor", *NEURON*, 32(2):213-223 (2001).

Heiser et al., "Inhibition of huntingtin fibrillogenesis by specific antibodies and small molecules: Implications for Huntington's disease therapy," Processings of the National Academy of Sciences of USA, 97(12):6739-6744 (2000), Abstract only.

Hsiao, K., "From prion diseases to Alzheimer's disease," *J. Neural. Transm. Suppl.* 49:135-144 (1997).

Hsu et al., "α-Synuclein Promotes Mitochondrial Deficit and Oxidative Stress," *Am. J. Pathology*, 157(2):401-410 (2000).

Hooper et al., *Celluar Peptidases in Immune Functions and Diseases 2*, (Langer and Ansorge, Eds., Plenum Publishers) 379-390 (2000).

Hornbeck et al., "Enzyme-Linked Immunosorbant Assays (ELISA)," *Current Protocols in Molecular Biology*, 11.2.1-11.2.22 (1991).

Hoyer, W. et al., "Dependence of alpha-Synuclein Aggregate Morphology on Solution Conditions," *J. Mol. Biol.*, 322:383-393 (2002).

Irizarry, M.C. "Nigral and cortical Lewy bodies and dystrophic nigral neurites in Parkinson's disease and cortical Lewy body disease contain α-synuclein immunoreactivity," *J. Neuropathol. Exp. Neurol.*, 57(4): 334-337 (1998).

Iwai, "Properties of NACP/alpha-synuclein and its role in Alzheimer's disease," *Molecular Basis of Disease*, 1502(1): 95-109 (2000).

Iwai et al., "The Precursor Protein of Non-Aβ Component of Alzheimer's Disease Amyloid is a Presynaptic Protein of the Central Nervous System," *Neuron*, 14:467-475 (1995).

Iwatsubo, T. et al., "Purification and Characterization of Lewy Bodies from the Brains of Patients with Diffuse Lewy Body Disease," *Am J Pathol.*, 148(5):1517-1529 (1996).

Jakes et al., "Epitope mapping of LB509, a monoclonal antibody directed against human α-synuclein," *Neurosci. Ltrs.*, 269:13-16 (1999).

Janeway et al., *Immunology*, 3rd edition, 8:18-8:19 (1997).

Jen, et al., "Preparation and purification of antisera against different regions or isoforms of beta-amyloid precursor protein," *Brain Research Protocols*, 2:23-30 (1997).

Jensen et al., "Residues in the synuclein consensus motif of the alpha-synuclein fragment, NAC, participate in transglutaminase-catalysed cross-linking to Alzheimer-disease amyloid beta A4 peptide," *Biochem. J.*, 310(Pt 1):91-94 (1995).

Jobling et al., "Analysis of structure and function of the B subunit of cholera toxin by the use of site-directed mutagenesis," *Molecular Microbiology*, 5(7):1755-1767 (1991).

Kim, T. D. et al., "Structural and Functional Implications of C-Terminal Regions of α-Synuclein," *Biochemistry*, 41:13782-13790 (2002).

Kim, T.D. et al., "Structural Changes in α-Synuclein Affect its Chaperone-like Activity in Vitro," *Protein Science*, 9:2489-2496 (2000).

Kotzbauer et al., "Lewy Body Pathology in Alzheimer's Disease," *Journal of Molecular Neuroscience*, 17(2): 225-232 (2001).

Kuby, J., eds., *Immunology*, pp. 92-97 and 110 (W.H. Freeman & Co., New York) (3rd Edition, 1997).

Kuby J., eds., *Immunology*, pp. 92-97 and 131 (W.H. Freeman & Co., New York) (3rd Edition, 1997).

Kuby J., eds., *Immunology*, pp. 156-158 (W.H. Freeman & Co., New York) 3rd Edition, 1997).

Lansbury Jr., P. T., "Evolution of amyloid: What normal protein folding may tell us about fibrillgenesis and disease," *Proc Natl Acad Sci*, 96(7): 3342-3344 (1999).

Lecerf et al., "Human singe-chain Fv intrabodies counteract in situ huntingtin aggregation in cellular models of Huntington's disease," Proceeding pf the National Academy of Sciences of USA, 98(8):4764-4769 (2001).

Lee et al., "Formation and Removal of α-Synuclein Aggregates in Cells Exposed to Mitochondrial Inhibitors," *J. Biol. Chem.*, 277(7):5411-5417 (2002).

Lee et al., "Human α-synuclein-harboring familial Parkinson's disease-linked Ala-53 → Thr mutation causes neurodegenerative disease with α-synuclein aggregation in transgenic mice," *PNAS*, 99:8968-8973 (2002).

Lee et al., "Truncated alpha-synuclein is generate in vivo and potentiates alpha synuclein aggregation," Database Biosis [Online] Biosciences Information Service, Philadelphia, PA, US (2003), Abstract only.

Lemere, C. A. et al., Amyloid-Beta Immunization in Alzheimer's Disease Transgenic Mouse Models and Wildtype Mice, *Neurochem Res.*, 28(7):1017-27.2003).

Lemere, et al., "Nasal Aβ treatment includes anti-Aβ antibody production and decreases cerebral amyloid burden in PD-APP mice," *Annals of the NY Acad. Sci.*, 920-328-331 (2000).

Lippa et al., "Antibodies to α-Synuclein Detect Lewy Bodies in Many Down's Syndrome Brains with Alzheimer's Disease," *Ann. Neurol.*, 45:353-357 (1999).

Lippa et al., "Alpha-Synuclein in Familial Alzheimer Disease: Epitope Mapping Parallels Dementia With Lewy Bodies and Parkinson Disease," *Archives of Neurology*, 58(11):1817-1820 (2001).

Lucking et al., "Alpha-synuclein and Parkinson's diease," *Cell. Mol. Life Sci.*, 57:1894-1908 (2000).

Luthi-Carter, R., "Progress towards a Vaccine for Huntington's Disease," *Mol Ther,*. 7(5,Pt 1):569-70 (2003).

Ma et al., "A-synuclein aggregation and neurodegeneraive disease," *Journal Alzheimer's Disease*, 5(2):139-148 (2003).

Masliah et al., "Dopaminergic Loss and Inclusion Body Formation in α-Synuclein Mice: Implications for Neurodegenerative Disorders," *Science*, 287:1265-1268 (2000).

Masliah et al., "Effects of α-Synuclein Immunization in a Mouse Model of Parkinson's Disease," *Neuron*, 46: 857-868 (2005).

Masliah et al., "β-Amyloid peptides enhance α-synuclein accumulation and neuronal deficits in a transgenic mouse model linking Alzheimer's disease and Parkinson's disease," 98(21):12245-12250 (2001).

McLean, et al., "Membrane Association and Protein Conformation of Alpha-Synuclein in Intact Neurons," *J Biol Chem.*, 275(12):8812-6 (2000).

Merriam-Webster online medical dictionary, entry for "cure", accessed Sep. 5, 2006.

Mishizen-Eberz et al., "Distinct cleavage patterns of normal and pathologic forms of α-synuclein by calpain I in vitro," *J. Neurochemistry*, 86:836-847 (2003).

Morgan, et al., "Aβ peptide vaccination prevents memory loss in an animal model of Alzheimer's disease," *Nature*, 408(6815):982-5 (2000).

Munch et al., "Potentional neurotoxic inflammatory responce to Aβ vaccination in humans," *J. Neural Transm.*, 109:1081-1087 (2002).

NCBI database search result for P37840 Alpha-synuclein conducted Oct. 21, 2002 at http://www.ncbi.nlm.nih.gov/entrez/query.fcgi?cmd=Retrieve&DB=protein&List_uids=58.

NCBI database search result for NP_009292 synuclein, alpha Oct. 21, 2002 at http://www.ncbi.nlm.nih.gov/entrez/query.fcgi?cmd=Retrieve&db=protein&list_uids=68.

Okochi, M. "Constitutive Phosphorylation of the Parkinson's Disease Assocated α-Synuclein," *J. Biol. Chem.*, 275(1): 390-397 (2000).

Palha et al., "Antibody recognition of amyloidogenic transthyretin variants in serum of patients with familial amyloidiotic polyneuropathy," *J. Mol. Med.*, 78:703-707 (2001).

PCT Search report of Apr. 7, 2009 for application PCT/US08/02392.

PCT/US05/37875 International Preliminary Report on Patentability Chapter 1 issued Apr. 24, 2007 with Written Opinion.

PCT/US05/28166 International Preliminary Report on Patentability Chapter 1 issued Feb. 13, 2007 with Written Opinion.

PCT/USO4/37444 International Preliminary Report on Patentability Chapter 1 issued Jun. 19, 2007 with Written Opinion.

PCT/US04/015836 International Preliminary Report on Patentability Chapter 1 issued Nov. 25, 2005 with Written Opinion.

PCT/US00/015239 International Preliminary Examination Report dated Aug. 13, 2001.

Perutz et al., "Amyloid fibers are water-filed nanotubes," *PNAS*, 99(8):5591-5595 (2002).

Perrin et al., "Epitope mapping and specificity of the anti-α-synuclein monoclonal antibody Syn-1 in mouse brain and cultured cell lines," *Neuroscience Letters*, 349:133-135 (2003) abstract only.

Primavera et al., "Brain Accumulation of Amyloid-β in Non-Alzheimer Neurodegeneration," *Journal of Alzheimer's Disease*, 1:183-193 (1999).

Que et al., "Effect of Carrier Selection on Immunogenicity of Protein Conjugate Vaccines against Plasmodium falciparum Circumsporozoites," *Infection and Immunity*, 56(10): 2645-2649 (1988).

Raso, "Immunotherapy of Alzheimer's Disease," *Immunotherapy Weekly*, Abstract (Apr. 2, 1998).

Rochet et al., "Inhabitation of fibrillization and accumulation of prefibrillar oligomers in mixtures of human and mouse α-synuclein" *Biochemistry*, 39(35):10619-10626 (2000).

Schenk, D., "Amyloid-β immunotherapy for Alzheimer's disease: the end of the beginning," *Nature Reviews*, 3:824-828 (2002).

Schenk et al., "Immunization with amyloid-β attenuates Alzheimer-disease-like pathology in the PDAPP mouse," *Nature*, 400:173-177 (1999).

Sidhu et al., "Does α-synuclein modulate dopaminergic synaptic content and tone at the synapse," FASEB, 18:637-647 (2004).

Sigurdsson et al., "Immunization Delays the Onset of Prion Disease in Mice," *American Journal of Pathology*, 161:13-17 (2002).

Spillantini et al., "α-Synuclein in Lewy bodies," Nature, 388:839-840 (1997).

Sigurdsson et al., "Anti-prion antibodies for prophyalxis following prion exposure in mice," *Neurosciences Letters*, 336:185-187 (2003).

SIPE, "Amyloidosis," *Annu. Rev. Biochem.*, 61:947-975 (1992).

Skipper et al., "Parkinson's Genetics: molecular Insights for the New Millennium," *Neurotoxicology*, 23: 503-514 (2002).

Skolnick and Fetrow, "From genes to protein structure and function: novel applications of computational approaches in the genomic era," *Trends in Biotech*, 18(1):34-39 (2000).

Small et al., "Alzheimer's disease and Abeta toxicity: from top to bottom," *Nat Rev Neurosci.*, 2(8):595-598 (2001).
Small et al., "Cerebral metabolic and cognitive decline in persons at genetic risk for Alzheimer's disease," *PNAS*, 97(11):6037-6042 (2000).
Solomon et al., "Monoclonal antibodies inhibit in vitro fibrillar aggregation of the Alzheimer β-amyloid peptide," *PNAS*, 93:452-455 (1996).
Solomon, B., "Immunological approaches as therapy for Alzheimer's disease," *Expert Opin. Biol. Ther.*, 2(8):907-917 (2002).
St. George-Hyslop et al., "Antibody clears senile plaques," *Nature*, 400:116-117 (1999).
Stein et al., "Lack of Neurodegeneration in Transgenic Mice Overexpressing Mutant Amyloid Precursor Protein is Associated with increased Levels of Transthyretin and Activation of Cell Survival Pathways," *The Journal of Neuroscience*, 22(17):7380-7388 (2002).
Su et al., "Intravascular infusions of soluble β-amyloid compromise the blood-brain barrier, activate CNS Glial cells and induce peripheral hemorrhage," *Brain Research*, 818:105-107 (1999).
Takahashi, M. "Phosphorylation of α-synuclein characteristic of synucleinopathy lesions is recapitulated in α-synuclein transgenic Drosophila," *Neuroscience Letters*, 336: 155-158 (2003).
Takeda et al., "Abnormal Accumulation of NACP/ α-Synuclein in Neurodegenerative Disorders," American Journal of Pathology, 152:367-372 (1998).
Takeda et al., "Abnormal Distribution of the Non-Aβ Component of Alzheimer's Disease Amyloid Precursor/alpha-synuclein in Lewy Body Disease as Revealed by Proteinase K and Fromic Acid Pretreatment," *Laboratory Investigation*, 79(9):1169-1177 (1998).
Takeda, A. et al., "C-terminal alpha-synuclein immunoreactivity in structures other than Lewy bodies in neurodegenerative disorders," *Acta Neuropathol*, 99:296-304 (2000).
Tal et al., "Complete Freund's Adjuvant Immunization Prolongs Survival in Experimental Prion Disease in Mice," *Journal of Neuroscience Research*, 71:286-290 (2003).
Tanaka et al., "NC-1900, an active fragment analog of arginine vasopressin, improves learning and memory deficits induced by beta-amyloid protein in rats," *European J. Pharmacology*, 352:135-142 (1998).
Tennent et al., "Serum amyloid P component prevents proteolysis of the amyloid fibrils of Alzheimer's disease and systemic amyloidosis," *PNAS*, 92:4299-4303 (1995).
Tofaris et al., "Physiological and Pathological Properties of α-synuclein," Cellular and Molecular Life Sciences, pp. 1-8 (2007).
Tofaris et al., "Ubiquitination of alpha-synuclein in Lewy bodies is a pathological event not associated with impairment of proteasome function," The Journal of Biological Chemistry, 278:44405-44411 (2003).
Tsim, K.W. et al., "Monoclonal antibodies specific for the different subunits of asymmetric acetylcholinesterase from chick muscle," *J. Neurochem.*, 51(1):95-104 (1988).
Ubol et al., "Roles of Immunoglobulin Valency and the Heavy-Chain Constant Domain in Antibody-Mediated Downregulation of Sindbis Virus Replication in Persistently Infected Neurons," *J. Virol.*, Mar. 1995; 69(3): 1990-1993.
Ueda et al., "Molecular cloning of cDNA encoding an unrecognized component of amyloid in Alzheimer disease," *PNAS*, 90:11282-11286 (1993).
Vickers, J.C., "A vaccine against Alzheimer's disease, Developments to date," *Drug Aging*, 19(7): 487-494 (2002).

Wakabayashi et al., "α-Synuclein immunoreactivity in glial cytoplasmic inclusions in multiple system atrophy," *Neuroscience Letters*, 249:180-182 (1998).
Wakabayashi et al., "NACP, a presynaptic protein, immunoreactivity in Lewy bodies in Parkinson's disease," *Neuroscience Letters*, 239(1) 45-48 (1997).
Wakabayashi et al., "Widespread occurrence of a-synuclein/NCAP-immunoreactive neuronal inclusions in juvenile and adult-onset Hallervorden-Spatz disease with Lewy bodies," *Neuropathology and Applied Neurobiology*, 25(5): 363-368 (1999).
Wakabayashi et al., "Accumulation of a-synuclein/NACP is a cytopathological feature common to Lewy body disease and multiple system atrophy," *Acta Neuropathol.*, 96(5): 445-452 (1998).
Walker et al., "Labeling of Cerebral Amyloid In Vivo with a Monoclonal Antibody," *J. Neuropath. Exp. Neurology*, 53(4):377-383 (1994).
Wanker, "Protein aggregation in Huntington's and Parkinson's disease: Implications or therapy," Molecular Medicine Today 2000 GB, 6(10):387-397 (2000), Abstract only.
Watson et al., "Chapter 14: The Introduction of Foreign Genes into Mice," *Molecular Biology of Watson Recombinant DNAs, 2nd ed.*, 255-272 (1993).
Weinreb et al., "NACP, A Protein Implicated in Alzheimer's Disease and Learning, Is Natively Unfolded," *Biochemistry*, 35(43):13709-13715 (1996).
Windisch et al., "Development of a new treatment for Alzheimer's disease and Parkinson's disease using anti-aggregatory [beta]-synuclein-derived peptides," Journal of Molecular Neuroscience, 19(2): 63-69 (2002) abstract only.
Wisniewski et al., "Therapeutics in Alzheimer's and Prion Diseases," *Biochemical Society Transactions*, 30(4):574-587 (2002).
Wong et al., "Neuritic Plaques and Cerebrovascular Amyloid in Alzheimer Disease are Antigenically Related," *PNAS*, 82:8729-8732 (1985).
Yoshimoto et al., "NACP, the precursor protein of the non-amyloid β/A4 protein (Aβ) component of Alzheimer disease amyloid, binds Aβ and stimulates Aβ aggregation," *PNAS*, 92:9141-9145 (1995).
Younkin, "Amyloid β vaccination: reduced plaques and improved cognition," *Nature Medicine*, 7(1):18-19 (2001).
Zhou et al., "A Human Single-Chain Fv Intrabody Blocks Aberrant Cellular Effects of Overexpressed alpha-Synuclein," *Mol. Ther.*, 10(6):1023-1031 (2004).
EP 10006567.5 Partial European Search Report completed May 11, 2011.
EP 10189868 European Search Report complete Jun. 28, 2011.
EP 11164647.7 Extended European Search Report completed Aug. 3, 2011.
Lantos et al., "Lewy Body in the brain of two members of a family with the 717 (Val to Ile) mutation of the amyloid precursor protein gene", *Neuroscience Letters*, 172 (1994) 77-79.
Lippa et al., "Lewy Bodies Contain Altered α-Synuclein in Brains of Many Familial Alzheimer's Disease Patients with Mutations in Presenilin and Amyloid Presursor Protein Genes". *American Journal of Pathology* vol. 153 No. 5 pp. (1998) 1365-1370.
PCT/US2006/028273 International Search Report mailed Sep. 24, 2007.
Revesz et al., "Pathology of familial Alzheimer's disease with Lewy bodies", *J Neural Transm* (1997) [Suppl] 51;121-135.
Spillantini et al., "Synuclein in flamentous inclusions of Lewy bodies from Parkinson's disease and dementia with Lewy bodies" Proc Natl Acad Sci USA 95(11):6469-6473 (1998).

| Residue # | | |
|---|---|---|
| (SEQ ID NO:1) | 1  5  10  15  20  25  30  35  40  45  50  55 | MDVFMKGLSKAKEGVVAAAEKTKQGVAEAAGKTKEGVLYVGSKTKEGVVHGVATVAE |

| Residue # | | |
|---|---|---|
| (SEQ ID NO:1) | 60  65  70  75  80  85  90  95  100  105  110 | KTKEQVTNVGGAVVTGVTAVAQKTVEGAGSIAAATGFVKKDQLGKNEEGAPQE |
| (SEQ ID NO:2) | | EQVTNVGGAVVTGVTAVAQKTVEGAGSIAAATGFV (residues 61-95) |
| (SEQ ID NO:3) | | KEQVTNVGGAVVTGVTAVAQKTVEGAGS (residues 60-87) |

| Residue # | | |
|---|---|---|
| (SEQ ID NO:1) | 115  120  125  130  135  140 | GILEDMPVDPDNEAYEMPSEEGYQDYEPEA (residues 1-140) |

Fig. 1

α-Synuclein Immunization Reduces the Formation SYN (+) Inclusion

Nontg | α-synuclein tg+CFA | α-syn tg+ vacc low tit | α-syn tg+ vacc high tit

SEQUENCE LISTING

<160> NUMBER OF SEQ ID NOS: 57

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Thr Gly Phe Val Lys
            85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 2
<211> LENGTH: 35
<212> TYPE: PRT
<213> ORGANISM: Homo sapiens

<400> SEQUENCE: 2

Glu Gln Val Thr Asn Val Gly Gly Ala Val Val Thr Gly Val Thr Ala
1               5                   10                  15

Val Ala Gln Lys Thr Val Glu Gly Ala Gly Ser Ile Ala Ala Ala Thr
            20                  25                  30

Gly Phe Val
        35

<210> SEQ ID NO 3
<211> LENGTH: 28
<212> TYPE: PRT
<213> ORGANISM: Homo sapiens

<400> SEQUENCE: 3

Lys Glu Gln Val Thr Asn Val Gly Gly Ala Val Val Thr Gly Val Thr
1               5                   10                  15

Ala Val Ala Gln Lys Thr Val Glu Gly Ala Gly Ser
            20                  25

<210> SEQ ID NO 4
<211> LENGTH: 13
<212> TYPE: PRT
<213> ORGANISM: Influenza virus

<400> SEQUENCE: 4

Pro Lys Tyr Val Lys Gln Asn Thr Leu Lys Leu Ala Thr
1               5                   10

```
<210> SEQ ID NO 5
<211> LENGTH: 16
<212> TYPE: PRT
<213> ORGANISM: Plasmodium sp.

<400> SEQUENCE: 5

Glu Lys Lys Ile Ala Lys Met Glu Lys Ala Ser Ser Val Phe Asn Val
1               5                   10                  15

<210> SEQ ID NO 6
<211> LENGTH: 10
<212> TYPE: PRT
<213> ORGANISM: Hepatitis B virus

<400> SEQUENCE: 6

Phe Phe Leu Leu Thr Arg Ile Leu Thr Ile
1               5                   10

<210> SEQ ID NO 7
<211> LENGTH: 19
<212> TYPE: PRT
<213> ORGANISM: Homo sapiens

<400> SEQUENCE: 7

Asp Gln Ser Ile Gly Asp Leu Ile Ala Glu Ala Met Asp Lys Val Gly
1               5                   10                  15

Asn Glu Gly

<210> SEQ ID NO 8
<211> LENGTH: 14
<212> TYPE: PRT
<213> ORGANISM: Mycobacterium bovis

<400> SEQUENCE: 8

Gln Val His Phe Gln Pro Leu Pro Pro Ala Val Val Lys Leu
1               5                   10

<210> SEQ ID NO 9
<211> LENGTH: 15
<212> TYPE: PRT
<213> ORGANISM: Clostridium tetani

<400> SEQUENCE: 9

Gln Tyr Ile Lys Ala Asn Ser Lys Phe Ile Gly Ile Thr Glu Leu
1               5                   10                  15

<210> SEQ ID NO 10
<211> LENGTH: 21
<212> TYPE: PRT
<213> ORGANISM: Clostridium tetani

<400> SEQUENCE: 10

Phe Asn Asn Phe Thr Val Ser Phe Trp Leu Arg Val Pro Lys Val Ser
1               5                   10                  15

Ala Ser His Leu Glu
            20

<210> SEQ ID NO 11
<211> LENGTH: 16
<212> TYPE: PRT
<213> ORGANISM: Human immunodeficiency virus

<400> SEQUENCE: 11
```

```
Lys Gln Ile Ile Asn Met Trp Gln Glu Val Gly Lys Ala Met Tyr Ala
1               5                   10                  15

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Cyclohexylalanine, Tyr or Phe
<220> FEATURE:
<223> OTHER INFORMATION: See specification as filed for detailed
      description of substitutions and preferred embodiments

<400> SEQUENCE: 12

Ala Lys Xaa Val Ala Ala Trp Thr Leu Lys Ala Ala Ala
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Glu Gln Val Thr Asn Val Cys Gly Gly Ala Val Val Thr
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Val Thr Ala Val Ala Gln Lys Thr Val Glu Cys Gly
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Amino-heptanoic acid

<400> SEQUENCE: 15

Cys Xaa Lys Asn Glu Glu Gly Ala Pro Cys Gln Glu Gly
1               5                   10

<210> SEQ ID NO 16
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

-continued

```
<222> LOCATION: (1)..(14)
<223> OTHER INFORMATION: This region may encompass SEQ ID NO: 13,
      SEQ ID NO: 14 or SEQ ID NO: 15
<220> FEATURE:
<223> OTHER INFORMATION: See specification as filed for detailed
      description of substitutions and preferred embodiments

<400> SEQUENCE: 16

Xaa Xaa Xaa Xaa Xaa Xaa Xaa Xaa Xaa Xaa Xaa Xaa Xaa Xaa Gln Tyr
1               5                   10                  15

Ile Lys Ala Asn Ser Lys Phe Ile Gly Ile Thr Glu Leu
            20                  25

<210> SEQ ID NO 17
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(14)
<223> OTHER INFORMATION: This region may encompass SEQ ID NO: 13,
      SEQ ID NO: 14 or SEQ ID NO: 15
<220> FEATURE:
<223> OTHER INFORMATION: See specification as filed for detailed
      description of substitutions and preferred embodiments

<400> SEQUENCE: 17

Xaa Xaa Xaa Xaa Xaa Xaa Xaa Xaa Xaa Xaa Xaa Xaa Xaa Xaa Phe Asn
1               5                   10                  15

Asn Phe Thr Val Ser Phe Trp Leu Arg Val Pro Lys Val Ser Ala Ser
            20                  25                  30

His Leu Glu
        35

<210> SEQ ID NO 18
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(14)
<223> OTHER INFORMATION: This region may encompass SEQ ID NO: 13,
      SEQ ID NO: 14 or SEQ ID NO: 15
<220> FEATURE:
<223> OTHER INFORMATION: See specification as filed for detailed
      description of substitutions and preferred embodiments

<400> SEQUENCE: 18

Xaa Xaa Xaa Xaa Xaa Xaa Xaa Xaa Xaa Xaa Xaa Xaa Xaa Xaa Gln Tyr
1               5                   10                  15

Ile Lys Ala Asn Ser Lys Phe Ile Gly Ile Thr Glu Leu
            20                  25

<210> SEQ ID NO 19
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(14)
<223> OTHER INFORMATION: This region may encompass SEQ ID NO: 13,
```

```
              SEQ ID NO: 14 or SEQ ID NO: 15
<220> FEATURE:
<223> OTHER INFORMATION: See specification as filed for detailed
      description of substitutions and preferred embodiments

<400> SEQUENCE: 19

Xaa Xaa Xaa Xaa Xaa Xaa Xaa Xaa Xaa Xaa Xaa Xaa Xaa Xaa Gln Tyr
1               5                   10                  15

Ile Lys Ala Asn Ser Lys Phe Ile Gly Ile Thr Glu Leu Phe Asn Asn
            20                  25                  30

Phe Thr Val Ser Phe Trp Leu Arg Val Pro Lys Val Ser Ala Ser His
        35                  40                  45

Leu Glu
    50

<210> SEQ ID NO 20
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Cyclohexylalanine, Tyr or Phe
<220> FEATURE:
<221> NAME/KEY: MOD_RES
<222> LOCATION: (14)..(27)
<223> OTHER INFORMATION: This region may encompass SEQ ID NO: 13,
      SEQ ID NO: 14 or SEQ ID NO: 15
<220> FEATURE:
<223> OTHER INFORMATION: See specification as filed for detailed
      description of substitutions and preferred embodiments

<400> SEQUENCE: 20

Ala Lys Xaa Val Ala Ala Trp Thr Leu Lys Ala Ala Ala Xaa Xaa Xaa
1               5                   10                  15

Xaa Xaa Xaa Xaa Xaa Xaa Xaa Xaa Xaa Xaa Xaa
            20                  25

<210> SEQ ID NO 21
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(14)
<223> OTHER INFORMATION: This region may encompass SEQ ID NO: 13,
      SEQ ID NO: 14 or SEQ ID NO: 15
<220> FEATURE:
<221> NAME/KEY: MOD_RES
<222> LOCATION: (15)..(28)
<223> OTHER INFORMATION: This region may encompass SEQ ID NO: 13,
      SEQ ID NO: 14 or SEQ ID NO: 15
<220> FEATURE:
<221> NAME/KEY: MOD_RES
<222> LOCATION: (29)..(42)
<223> OTHER INFORMATION: This region may encompass SEQ ID NO: 13,
      SEQ ID NO: 14 or SEQ ID NO: 15
<220> FEATURE:
<221> NAME/KEY: MOD_RES
<222> LOCATION: (45)..(45)
<223> OTHER INFORMATION: Cyclohexylalanine, Tyr or Phe
<220> FEATURE:
<223> OTHER INFORMATION: See specification as filed for detailed
      description of substitutions and preferred embodiments

<400> SEQUENCE: 21
```

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Ala Lys Xaa Val Ala Ala
        35                  40                  45

Trp Thr Leu Lys Ala Ala Ala
    50                  55

<210> SEQ ID NO 22
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Cyclohexylalanine, Tyr or Phe
<220> FEATURE:
<221> NAME/KEY: MOD_RES
<222> LOCATION: (14)..(27)
<223> OTHER INFORMATION: This region may encompass SEQ ID NO: 13,
      SEQ ID NO: 14 or SEQ ID NO: 15
<220> FEATURE:
<221> NAME/KEY: MOD_RES
<222> LOCATION: (28)..(41)
<223> OTHER INFORMATION: This region may encompass SEQ ID NO: 13,
      SEQ ID NO: 14 or SEQ ID NO: 15
<220> FEATURE:
<221> NAME/KEY: MOD_RES
<222> LOCATION: (42)..(55)
<223> OTHER INFORMATION: This region may encompass SEQ ID NO: 13,
      SEQ ID NO: 14 or SEQ ID NO: 15
<220> FEATURE:
<221> NAME/KEY: MOD_RES
<222> LOCATION: (56)..(69)
<223> OTHER INFORMATION: This region may encompass SEQ ID NO: 13,
      SEQ ID NO: 14 or SEQ ID NO: 15
<220> FEATURE:
<223> OTHER INFORMATION: See specification as filed for detailed
      description of substitutions and preferred embodiments

<400> SEQUENCE: 22

Ala Lys Xaa Val Ala Ala Trp Thr Leu Lys Ala Ala Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa
65

<210> SEQ ID NO 23
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(14)
<223> OTHER INFORMATION: This region may encompass SEQ ID NO: 13,
      SEQ ID NO: 14 or SEQ ID NO: 15
<220> FEATURE:
```

```
<221> NAME/KEY: MOD_RES
<222> LOCATION: (17)..(17)
<223> OTHER INFORMATION: Cyclohexylalanine, Tyr or Phe
<220> FEATURE:
<223> OTHER INFORMATION: See specification as filed for detailed
      description of substitutions and preferred embodiments

<400> SEQUENCE: 23

Xaa Xaa Xaa Xaa Xaa Xaa Xaa Xaa Xaa Xaa Xaa Xaa Xaa Xaa Ala Lys
1               5                   10                  15

Xaa Val Ala Ala Trp Thr Leu Lys Ala Ala Ala
            20                  25

<210> SEQ ID NO 24
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(14)
<223> OTHER INFORMATION: This region may encompass SEQ ID NO: 13,
      SEQ ID NO: 14 or SEQ ID NO: 15
<220> FEATURE:
<223> OTHER INFORMATION: See specification as filed for detailed
      description of substitutions and preferred embodiments

<400> SEQUENCE: 24

Xaa Xaa Xaa Xaa Xaa Xaa Xaa Xaa Xaa Xaa Xaa Xaa Xaa Xaa Ile Ser
1               5                   10                  15

Gln Ala Val His Ala Ala His Ala Glu Ile Asn Glu Ala Gly Arg
            20                  25                  30

<210> SEQ ID NO 25
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(27)
<223> OTHER INFORMATION: This region may encompass SEQ ID NO: 13,
      SEQ ID NO: 14 or SEQ ID NO: 15
<220> FEATURE:
<221> NAME/KEY: MOD_RES
<222> LOCATION: (28)..(41)
<223> OTHER INFORMATION: This region may encompass SEQ ID NO: 13,
      SEQ ID NO: 14 or SEQ ID NO: 15
<220> FEATURE:
<221> NAME/KEY: MOD_RES
<222> LOCATION: (42)..(55)
<223> OTHER INFORMATION: This region may encompass SEQ ID NO: 13,
      SEQ ID NO: 14 or SEQ ID NO: 15
<220> FEATURE:
<223> OTHER INFORMATION: See specification as filed for detailed
      description of substitutions and preferred embodiments

<400> SEQUENCE: 25

Pro Lys Tyr Val Lys Gln Asn Thr Leu Lys Leu Ala Thr Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa
    50                  55
```

```
<210> SEQ ID NO 26
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(14)
<223> OTHER INFORMATION: This region may encompass SEQ ID NO: 13,
      SEQ ID NO: 14 or SEQ ID NO: 15
<220> FEATURE:
<221> NAME/KEY: MOD_RES
<222> LOCATION: (28)..(41)
<223> OTHER INFORMATION: This region may encompass SEQ ID NO: 13,
      SEQ ID NO: 14 or SEQ ID NO: 15
<220> FEATURE:
<223> OTHER INFORMATION: See specification as filed for detailed
      description of substitutions and preferred embodiments

<400> SEQUENCE: 26

Xaa Xaa Xaa Xaa Xaa Xaa Xaa Xaa Xaa Xaa Xaa Xaa Xaa Xaa Pro Lys
1               5                   10                  15

Tyr Val Lys Gln Asn Thr Leu Lys Leu Ala Thr Xaa Xaa Xaa Xaa Xaa
            20                  25                  30

Xaa Xaa Xaa Xaa Xaa Xaa Xaa Xaa Xaa
        35                  40

<210> SEQ ID NO 27
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(14)
<223> OTHER INFORMATION: This region may encompass SEQ ID NO: 13,
      SEQ ID NO: 14 or SEQ ID NO: 15
<220> FEATURE:
<221> NAME/KEY: MOD_RES
<222> LOCATION: (15)..(28)
<223> OTHER INFORMATION: This region may encompass SEQ ID NO: 13,
      SEQ ID NO: 14 or SEQ ID NO: 15
<220> FEATURE:
<221> NAME/KEY: MOD_RES
<222> LOCATION: (29)..(42)
<223> OTHER INFORMATION: This region may encompass SEQ ID NO: 13,
      SEQ ID NO: 14 or SEQ ID NO: 15
<220> FEATURE:
<223> OTHER INFORMATION: See specification as filed for detailed
      description of substitutions and preferred embodiments

<400> SEQUENCE: 27

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Pro Lys Tyr Val Lys Gln
        35                  40                  45

Asn Thr Leu Lys Leu Ala Thr
    50                  55

<210> SEQ ID NO 28
<211> LENGTH: 41
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(14)
<223> OTHER INFORMATION: This region may encompass SEQ ID NO: 13,
      SEQ ID NO: 14 or SEQ ID NO: 15
<220> FEATURE:
<221> NAME/KEY: MOD_RES
<222> LOCATION: (15)..(28)
<223> OTHER INFORMATION: This region may encompass SEQ ID NO: 13,
      SEQ ID NO: 14 or SEQ ID NO: 15
<220> FEATURE:
<223> OTHER INFORMATION: See specification as filed for detailed
      description of substitutions and preferred embodiments

<400> SEQUENCE: 28

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Pro Lys Tyr Val
            20                  25                  30

Lys Gln Asn Thr Leu Lys Leu Ala Thr
        35                  40

<210> SEQ ID NO 29
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(14)
<223> OTHER INFORMATION: This region may encompass SEQ ID NO: 13,
      SEQ ID NO: 14 or SEQ ID NO: 15
<220> FEATURE:
<221> NAME/KEY: MOD_RES
<222> LOCATION: (80)..(93)
<223> OTHER INFORMATION: This region may encompass SEQ ID NO: 13,
      SEQ ID NO: 14 or SEQ ID NO: 15
<220> FEATURE:
<221> NAME/KEY: MOD_RES
<222> LOCATION: (94)..(107)
<223> OTHER INFORMATION: This region may encompass SEQ ID NO: 13,
      SEQ ID NO: 14 or SEQ ID NO: 15
<220> FEATURE:
<221> NAME/KEY: MOD_RES
<222> LOCATION: (108)..(121)
<223> OTHER INFORMATION: This region may encompass SEQ ID NO: 13,
      SEQ ID NO: 14 or SEQ ID NO: 15
<220> FEATURE:
<221> NAME/KEY: MOD_RES
<222> LOCATION: (122)..(135)
<223> OTHER INFORMATION: This region may encompass SEQ ID NO: 13,
      SEQ ID NO: 14 or SEQ ID NO: 15
<220> FEATURE:
<223> OTHER INFORMATION: See specification as filed for detailed
      description of substitutions and preferred embodiments

<400> SEQUENCE: 29

Xaa Xaa Xaa Xaa Xaa Xaa Xaa Xaa Xaa Xaa Xaa Xaa Xaa Xaa Pro Lys
1               5                   10                  15

Tyr Val Lys Gln Asn Thr Leu Lys Leu Ala Thr Glu Lys Ile Ala
            20                  25                  30

Lys Met Glu Lys Ala Ser Ser Val Phe Asn Val Gln Tyr Ile Lys Ala
        35                  40                  45

Asn Ser Lys Phe Ile Gly Ile Thr Glu Leu Phe Asn Asn Phe Thr Val
    50                  55                  60

Ser Phe Trp Leu Arg Val Pro Lys Val Ser Ala Ser His Leu Glu Xaa
```

```
                65                  70                  75                  80
Xaa Xaa Xaa Xaa Xaa Xaa Xaa Xaa Xaa Xaa Xaa Xaa Xaa Xaa Xaa
                        85                  90                  95

Xaa Xaa Xaa Xaa Xaa Xaa Xaa Xaa Xaa Xaa Xaa Xaa Xaa Xaa Xaa
                    100                 105                 110

Xaa Xaa Xaa Xaa Xaa Xaa Xaa Xaa Xaa Xaa Xaa Xaa Xaa Xaa Xaa
                115                 120                 125

Xaa Xaa Xaa Xaa Xaa Xaa Xaa Gln Tyr Ile Lys Ala Asn Ser Lys Phe
            130                 135                 140

Ile Gly Ile Thr Glu Leu Phe Asn Asn Phe Thr Val Ser Phe Trp Leu
145                 150                 155                 160

Arg Val Pro Lys Val Ser Ala Ser His Leu Glu
                165                 170

<210> SEQ ID NO 30
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(14)
<223> OTHER INFORMATION: This region may encompass SEQ ID NO: 13,
      SEQ ID NO: 14 or SEQ ID NO: 15
<220> FEATURE:
<221> NAME/KEY: MOD_RES
<222> LOCATION: (52)..(65)
<223> OTHER INFORMATION: This region may encompass SEQ ID NO: 13,
      SEQ ID NO: 14 or SEQ ID NO: 15
<220> FEATURE:
<221> NAME/KEY: MOD_RES
<222> LOCATION: (103)..(116)
<223> OTHER INFORMATION: This region may encompass SEQ ID NO: 13,
      SEQ ID NO: 14 or SEQ ID NO: 15
<220> FEATURE:
<223> OTHER INFORMATION: See specification as filed for detailed
      description of substitutions and preferred embodiments

<400> SEQUENCE: 30

Xaa Xaa Xaa Xaa Xaa Xaa Xaa Xaa Xaa Xaa Xaa Xaa Xaa Xaa Gln Tyr
1               5                   10                  15

Ile Lys Ala Asn Ser Lys Phe Ile Gly Ile Thr Glu Leu Cys Phe Asn
                20                  25                  30

Asn Phe Thr Val Ser Phe Trp Leu Arg Val Pro Lys Val Ser Ala Ser
            35                  40                  45

His Leu Glu Xaa Xaa Xaa Xaa Xaa Xaa Xaa Xaa Xaa Xaa Xaa Xaa Xaa
        50                  55                  60

Xaa Gln Tyr Ile Lys Ala Asn Ser Lys Phe Ile Gly Ile Thr Glu Leu
65                  70                  75                  80

Cys Phe Asn Asn Phe Thr Val Ser Phe Trp Leu Arg Val Pro Lys Val
                85                  90                  95

Ser Ala Ser His Leu Glu Xaa Xaa Xaa Xaa Xaa Xaa Xaa Xaa
                100                 105                 110

Xaa Xaa Xaa Xaa
        115

<210> SEQ ID NO 31
<211> LENGTH: 29
<212> TYPE: PRT
<213> ORGANISM: Artificial Sequence
<220> FEATURE:
<223> OTHER INFORMATION: Description of Artificial Sequence: Synthetic
```

```
                                -continued
        peptide
<220> FEATURE:
<221> NAME/KEY: MOD_RES
<222> LOCATION: (1)..(14)
<223> OTHER INFORMATION: This region may encompass SEQ ID NO: 13,
      SEQ ID NO: 14 or SEQ ID NO: 15
<220> FEATURE:
<223> OTHER INFORMATION: See specification as filed for detailed
      description of substitutions and preferred embodiments

<400> SEQUENCE: 31

Xaa Xaa Xaa Xaa Xaa Xaa Xaa Xaa Xaa Xaa Xaa Xaa Xaa Gln Tyr
1               5                   10                  15

Ile Lys Ala Asn Ser Lys Phe Ile Gly Ile Thr Glu Leu
            20                  25

<210> SEQ ID NO 32
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Glu Gln Val Thr Asn Val Gly Gly Ala Ile Ser Gln Ala Val His Ala
1               5                   10                  15

Ala His Ala Glu Ile Asn Glu Ala Gly Arg
            20                  25

<210> SEQ ID NO 33
<211> LENGTH: 43
<212> TYPE: PRT
<213> ORGANISM: Homo sapiens

<400> SEQUENCE: 33

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40

<210> SEQ ID NO 34
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Ala Glu Phe Arg His Asp Gln Tyr Ile Lys Ala Asn Ser Lys Phe
1               5                   10                  15

Ile Gly Ile Thr Glu Leu
            20

<210> SEQ ID NO 35
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35
```

```
Asp Ala Glu Phe Arg His Asp Phe Asn Asn Phe Thr Val Ser Phe Trp
1               5                   10                  15

Leu Arg Val Pro Lys Val Ser Ala Ser His Leu Glu
            20                  25
```

<210> SEQ ID NO 36
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Asp Ala Glu Phe Arg His Asp Gln Tyr Ile Lys Ala Asn Ser Lys Phe
1               5                   10                  15

Ile Gly Ile Thr Glu Leu Phe Asn Asn Phe Thr Val Ser Phe Trp Leu
            20                  25                  30

Arg Val Pro Lys Val Ser Ala Ser His Leu Glu
        35                  40
```

<210> SEQ ID NO 37
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Glu Phe Arg His Asp Ser Gly Gln Tyr Ile Lys Ala Asn Ser Lys Phe
1               5                   10                  15

Ile Gly Ile Thr Glu Leu
            20
```

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Cyclohexylalanine, Tyr or Phe
<220> FEATURE:
<223> OTHER INFORMATION: See specification as filed for detailed
      description of substitutions and preferred embodiments

<400> SEQUENCE: 38

```
Ala Lys Xaa Val Ala Ala Trp Thr Leu Lys Ala Ala Ala Asp Ala Glu
1               5                   10                  15

Phe Arg His Asp
            20
```

<210> SEQ ID NO 39
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Cyclohexylalanine, Tyr or Phe
<220> FEATURE:

<223> OTHER INFORMATION: See specification as filed for detailed
      description of substitutions and preferred embodiments

<400> SEQUENCE: 39

Asp Ala Glu Phe Arg His Asp Ala Glu Phe Arg His Asp Asp Ala
1               5                   10                  15

Glu Phe Arg His Asp Ala Lys Xaa Val Ala Ala Trp Thr Leu Lys Ala
                20                  25                  30

Ala Ala

<210> SEQ ID NO 40
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Cyclohexylalanine, Tyr or Phe
<220> FEATURE:
<223> OTHER INFORMATION: See specification as filed for detailed
      description of substitutions and preferred embodiments

<400> SEQUENCE: 40

Ala Lys Xaa Val Ala Ala Trp Thr Leu Lys Ala Ala Asp Ala Glu
1               5                   10                  15

Phe Arg His Asp Asp Ala Glu Phe Arg His Asp Asp Ala Glu Phe Arg
                20                  25                  30

His Asp

<210> SEQ ID NO 41
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Cyclohexylalanine, Tyr or Phe
<220> FEATURE:
<223> OTHER INFORMATION: See specification as filed for detailed
      description of substitutions and preferred embodiments

<400> SEQUENCE: 41

Asp Ala Glu Phe Arg His Asp Ala Lys Xaa Val Ala Ala Trp Thr Leu
1               5                   10                  15

Lys Ala Ala Ala
                20

<210> SEQ ID NO 42
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Ala Glu Phe Arg His Asp Ile Ser Gln Ala Val His Ala Ala His
1               5                   10                  15

Ala Glu Ile Asn Glu Ala Gly Arg
                20

<210> SEQ ID NO 43
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Phe Arg His Asp Ser Gly Tyr Ile Ser Gln Ala Val His Ala Ala His
1               5                   10                  15

Ala Glu Ile Asn Glu Ala Gly Arg
            20

<210> SEQ ID NO 44
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Glu Phe Arg His Asp Ser Gly Ile Ser Gln Ala Val His Ala Ala His
1               5                   10                  15

Ala Glu Ile Asn Glu Ala Gly Arg
            20

<210> SEQ ID NO 45
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Pro Lys Tyr Val Lys Gln Asn Thr Leu Lys Leu Ala Thr Asp Ala Glu
1               5                   10                  15

Phe Arg His Asp Asp Ala Glu Phe Arg His Asp Ala Glu Phe Arg
            20                  25                  30

His Asp

<210> SEQ ID NO 46
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Ala Glu Phe Arg His Asp Pro Lys Tyr Val Lys Gln Asn Thr Leu
1               5                   10                  15

Lys Leu Ala Thr Asp Ala Glu Phe Arg His Asp
            20                  25

<210> SEQ ID NO 47
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Asp Ala Glu Phe Arg His Asp Asp Ala Glu Phe Arg His Asp Ala
1               5                   10                  15

Glu Phe Arg His Asp Pro Lys Tyr Val Lys Gln Asn Thr Leu Lys Leu
            20                  25                  30

Ala Thr

<210> SEQ ID NO 48
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Ala Glu Phe Arg His Asp Asp Ala Glu Phe Arg His Asp Pro Lys
1               5                   10                  15

Tyr Val Lys Gln Asn Thr Leu Lys Leu Ala Thr
            20                  25

<210> SEQ ID NO 49
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Ala Glu Phe Arg His Asp Pro Lys Tyr Val Lys Gln Asn Thr Leu
1               5                   10                  15

Lys Leu Ala Thr Glu Lys Lys Ile Ala Lys Met Glu Lys Ala Ser Ser
            20                  25                  30

Val Phe Asn Val Gln Tyr Ile Lys Ala Asn Ser Lys Phe Ile Gly Ile
        35                  40                  45

Thr Glu Leu Phe Asn Asn Phe Thr Val Ser Phe Trp Leu Arg Val Pro
    50                  55                  60

Lys Val Ser Ala Ser His Leu Glu Asp Ala Glu Phe Arg His Asp
65                  70                  75

<210> SEQ ID NO 50
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ala Glu Phe Arg His Asp Asp Ala Glu Phe Arg His Asp Ala
1               5                   10                  15

Glu Phe Arg His Asp Gln Tyr Ile Lys Ala Asn Ser Lys Phe Ile Gly
            20                  25                  30

Ile Thr Glu Leu Asn Asn Phe Thr Val Ser Phe Trp Leu Arg Val Pro
        35                  40                  45

Lys Val Ser Ala Ser His Leu Glu
    50                  55

<210> SEQ ID NO 51
<211> LENGTH: 44
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 51

Asp Ala Glu Phe Arg His Asp Gln Tyr Ile Lys Ala Asn Ser Lys Phe
1               5                   10                  15

Ile Gly Ile Thr Glu Leu Cys Phe Asn Asn Phe Thr Val Ser Phe Trp
            20                  25                  30

Leu Arg Val Pro Lys Val Ser Ala Ser His Leu Glu
        35                  40

<210> SEQ ID NO 52
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ala Glu Phe Arg His Asp Gln Tyr Ile Lys Ala Asn Ser Lys Phe
1               5                   10                  15

Ile Gly Ile Thr Glu Leu Cys Phe Asn Asn Phe Thr Val Ser Phe Trp
            20                  25                  30

Leu Arg Val Pro Lys Val Ser Ala Ser His Leu Glu Asp Ala Glu Phe
        35                  40                  45

Arg His Asp
    50

<210> SEQ ID NO 53
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Ala Glu Phe Arg His Asp Gln Tyr Ile Lys Ala Asn Ser Lys Phe
1               5                   10                  15

Ile Gly Ile Thr Glu Leu
            20

<210> SEQ ID NO 54
<211> LENGTH: 14
<212> TYPE: PRT
<213> ORGANISM: Homo sapiens

<400> SEQUENCE: 54

Lys Glu Gln Val Thr Asn Val Cys Gly Gly Ala Val Val Thr
1               5                   10

<210> SEQ ID NO 55
<211> LENGTH: 13
<212> TYPE: PRT
<213> ORGANISM: Homo sapiens

<400> SEQUENCE: 55

Gly Val Thr Ala Val Ala Gln Lys Thr Val Glu Cys Gly
1               5                   10

<210> SEQ ID NO 56
<211> LENGTH: 13
```

```
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Amino-heptanoic acid

<400> SEQUENCE: 56

Cys Xaa Lys Asn Glu Glu Gly Ala Pro Cys Gln Glu Gly
1               5                   10

<210> SEQ ID NO 57
<211> LENGTH: 14
<212> TYPE: PRT
<213> ORGANISM: Homo sapiens
<220> FEATURE:
<223> OTHER INFORMATION: N-term acetylated

<400> SEQUENCE: 57

Pro Ser Glu Glu Gly Tyr Gln Asp Tyr Glu Pro Glu Cys
1               5                   10

Ala
```

PREVENTION AND TREATMENT OF SYNUCLEINOPATHIC AND AMYLOIDOGENIC DISEASE

CROSS-REFERENCE TO RELATED APPLICATIONS

This application is a national stage entry of International Application No. PCT/US2008/002392, filed Feb. 22, 2008, which claims priority under 35 U.S.C. 119(e) to U.S. Application No. 60/984,721, filed Nov. 1, 2007, and is also a continuation in-part of U.S. application Ser. No. 11/697,646, filed Apr. 6, 2007, which is a continuation in-part of U.S. application Ser. No. 11/710,248, filed Feb. 23, 2007. Each of the forgoing applications is herein incorporated by reference in its entirety for all purposes.

NAMES OF PARTIES TO JOINT RESEARCH AGREEMENT

The claimed invention was made pursuant to a joint written research agreement between Elan Pharmaceuticals, Inc. and The Regents of the University of California.

BACKGROUND OF THE INVENTION

Alpha-synuclein (alpha-SN) brain pathology is a conspicuous feature of several neurodegenerative diseases, including Parkinson's disease (PD), dementia with Lewy bodies (DLB), the Lewy body variant of Alzheimer's disease (LBVAD), multiple systems atrophy (MSA), and neurodegeneration with brain iron accumulation type-1 (NBIA-1). Common to all of these diseases, termed synucleinopathies, are proteinaceous insoluble inclusions in the neurons and the glia which are composed primarily of alphaSN.

Lewy bodies and Lewy neurites are intraneuronal inclusions which are composed primarily of alpha-SN. Lewy bodies and Lewy neurites are the neuropathological hallmarks Parkinson's disease (PD). PD and other synucleinopathic diseases have been collectively referred to as Lewy body disease (LBD). LBD is characterized by degeneration of the dopaminergic system, motor alterations, cognitive impairment, and formation of Lewy bodies (LBs). (McKeith et al., *Clinical and pathological diagnosis of dementia with Lewy bodies (DLB): Report of the CDLB International Workshop, Neurology* (1996) 47:1113-24). Other LBDs include diffuse Lewy body disease (DLBD), Lewy body variant of Alzheimer's disease (LBVAD), combined PD and Alzheimer's disease (AD), and multiple systems atrophy. Dementia with Lewy bodies (DLB) is a term coined to reconcile differences in the terminology of LBDs.

Disorders with LBs continue to be a common cause for movement disorders and cognitive deterioration in the aging population (Galasko et al., *Clinical-neuropathological correlations in Alzheimer's disease and related dementias. Arch. Neurol.* (1994) 51:888-95). Although their incidence continues to increase, creating a serious public health problem, to date these disorders are neither curable nor preventable and understanding the causes and pathogenesis of PD is critical towards developing new treatments (Tanner et al., *Epidemiology of Parkinson's disease and akinetic syndromes, Curr. Opin. Neurol.* (2000) 13:427-30). The cause for PD is controversial and multiple factors have been proposed to play a role, including various neurotoxins and genetic susceptibility factors.

In recent years, new hope for understanding the pathogenesis of PD has emerged. Specifically, several studies have shown that the synaptic protein alpha-SN plays a central role in PD pathogenesis since: (1) this protein accumulates in LBs (Spillantini et al., *Nature* (1997) 388:839-40; Takeda et al., *AM. J. Pathol.* (1998) 152:367-72; Wakabayashi et al., *Neurosci. Lett.* (1997) 239:45-8), (2) mutations in the alpha-SN gene co-segregate with rare familial forms of parkinsonism (Kruger et al., *Nature Gen.* (1998) 18:106-8; Polymeropoulos M H, et al., *Science* (1997) 276:2045-7) and, (3) its overexpression in transgenic mice (Masliah et al., *Science* (2000) 287:1265-9) and *Drosophila* (Feany et al., *Nature* (2000) 404:394-8) mimics several pathological aspects of PD. Thus, the fact that accumulation of alpha-SN in the brain is associated with similar morphological and neurological alterations in species as diverse as humans, mice, and flies suggests that this molecule contributes to the development of PD.

An alpha-SN fragment, previously determined to be a constituent of AD amyloid plaques, was termed the non-amyloid-beta (non-An) component of AD amyloid (NAC) (Iwai A., *Biochim. Biophys. Acta* (2000) 1502:95-109); Masliah et al., *AM. J. Pathol* (1996) 148:201-10; Uéda et al., *Proc. Natl. Acad. Sci. USA* (1993) 90:11282-6). Although the precise function of NAC is not known, it may play a critical role in synaptic events, such as neural plasticity during development, and learning and degeneration of nerve terminals under pathological conditions in LBD, AD, and other disorders (Hasimoto et al., *Alpha-Synuclein in Lewy body disease and Alzheimer's disease, Brain Pathol* (1999) 9:707-20; Masliah, et al., (2000).

AD, PD, and dementia with Lewy bodies (DLB) are the most commonly found neurodegenerative disorders in the elderly. Although their incidence continues to increase, creating a serious public health problem, to date these disorders are neither curable nor preventable. Recent epidemiological studies have demonstrated a close clinical relationship between AD and PD, as about 30% of Alzheimer's patients also have PD. Compared to the rest of the aging population, patients with AD are thus more likely to develop concomitant PD. Furthermore, PD patients that become demented usually have developed classical AD. Although each neurodegenerative disease appears to have a predilection for specific brain regions and cell populations, resulting in distinct pathological features, PD, AD, DLB and LBD also share common pathological hallmarks. Patients with familial AD, Down syndrome, or sporadic AD develop LBs on the amygdala, which are the classical neuropathological hallmarks of PD. Additionally, each disease is associated with the degeneration of neurons, interneuronal synaptic connections and eventually cell death, the depletion of neurotransmitters, and abnormal accumulation of misfolded proteins, the precursors of which participate in normal central nervous system function. Biochemical studies have confirmed the link between AD, PD and DLB.

The neuritic plaques that are the classic pathological hallmark of AD contain beta-amyloid (Aβ) peptide and non-beta amyloid component (NAC) peptide. Aβ is derived from a larger precursor protein termed amyloid precursor protein (APP). NAC is derived from a larger precursor protein termed the non-beta amyloid component of APP, now more commonly referred to as alpha-SN. NAC comprises amino acid residues 60-87 or 61-95 of alpha-SN. Both Aβ and NAC were first identified in amyloid plaques as proteolytic fragments of their respective full-length proteins, for which the full-length cDNAs were identified and cloned.

Alpha-SN is part of a large family of proteins including beta- and gamma-synuclein and synoretin. Alpha-SN is expressed in the normal state associated with synapses and is believed to play a role in neural plasticity, learning and memory. Mutations in human (h) alpha-SN that enhance the aggregation of alpha-SN have been identified (Ala30Pro and Ala53Thr) and are associated with rare forms of autosomal dominant forms of PD. The mechanism by which these mutations increase the propensity of alpha-SN to aggregate are unknown.

Despite the fact that a number of mutations can be found in APP and alpha-SN in the population, most cases of AD and PD are sporadic. The most frequent sporadic forms of these diseases are associated with an abnormal accumulation of Aβ and alpha-SN, respectively. However, the reasons for over accumulation of these proteins is unknown. Aβ is secreted from neurons and accumulates in extracellular amyloid plaques. Additionally Aβ can be detected inside neurons. Alpha-SN accumulates in intraneuronal inclusions called LBs. Although the two proteins are typically found together in extracellular neuritic AD plaques, they are also occasionally found together in intracellular inclusions.

The mechanisms by which alpha-SN accumulation leads to neurodegeneration and the characteristics symptoms of PD are unclear. However, identifying the role of factors promoting and/or blocking alpha-SN aggregation is critical for the understanding of LBD pathogenesis and development of novel treatments for its associated disorders. Research for identifying treatments has been directed toward searching for compounds that reduce alpha-SN aggregation (Hashimoto, et al.) or testing growth factors that will promote the regeneration and/or survival of dopaminergic neurons, which are the cells primarily affected (Djaldetti et al., *New therapies for Parkinson's disease, J. Neurol* (2001) 248:357-62; Kirik et al., *Long-term rAAV-mediated gene transfer of GDNF in the rat Parkinson's model: intrastriatal but not intranigral transduction promotes functional regeneration in the lesioned nigrostriatal system, J. Neurosci* (2000) 20:4686-4700). Recent studies in a transgenic mouse model of AD have shown that antibodies against Aβ 1-42 facilitate and stimulate the removal of amyloid from the brain, improve AD-like pathology and resulting in improve cognitive performance (Schenk et al., *Immunization with amyloid-β attenuates Alzheimer-disease-like pathology in PDAPP mouse, Nature* (1999) 408:173-177; Morgan et al., *A-beta peptide vaccination prevents memory loss in an animal model of Alzheimer's disease, Nature* (2000) 408:982-985; Janus et al., *A-beta peptide immunization reduces behavioral impairment and plaques in a model of Alzheimer's disease, Nature* (2000) 408:979-82). In contrast to the extracellular amyloid plaques found in the brains of Alzheimer's patients, Lewy bodies are intracellular, and antibodies do not typically enter the cell.

Surprisingly, given the intracellular nature of LBs in brain tissue, the inventors have succeeded in reducing the number of inclusions in transgenic mice immunized with synuclein. The present invention is directed inter alia to treatment of PD and other diseases associated with LBs by administration of synuclein, fragments of synuclein, antigens that mimic synuclein or fragments thereof, or antibodies to certain epitopes of synuclein to a patient under conditions that generate a beneficial immune response in the patient. The inventors have also surprisingly succeeded in reducing the number of inclusions in transgenic mice immunized with Aβ. The present invention is directed inter alia to treatment of PD and other diseases associated with LBs by administration of Aβ, fragments of Aβ, antigens that mimic Aβ or fragments thereof, or antibodies to certain epitopes of Aβ to a patient under conditions that generate a beneficial immune response in the patient. The invention thus fulfills a longstanding need for therapeutic regimes for preventing or ameliorating the neuropathology and, in some patients, the cognitive impairment associated with PD and other diseases associated with LBs.

This application is related to U.S. application Ser. No. 11/710,248 filed Feb. 23, 2006, U.S. application Ser. No. 11/660,015 filed Feb. 9, 2006, PCT Publication No. WO/2006/02058 filed Aug. 9, 2005, U.S. patent application Ser. Nos. 11/185,907, filed Jul. 19, 2005, 10/915,214, filed Aug. 9, 2004, U.S. Pat. Nos. 6,787,523 and 6,923,964, U.S. patent application Nos. 60/423,012; 10/699,517; and 10/698,099, and PCT Application No. PCT/US03/34527, each of which is incorporated by reference in its entirety for all purposes.

BRIEF SUMMARY OF THE INVENTION

In one aspect, the invention provides methods of preventing or treating a disease characterized by Lewy bodies or alpha-SN aggregation in the brain. Such methods entail, inducing an immunogenic response against alpha-SN. Such induction may be achieved by active administration of an immunogen or passive by administration of an antibody or a derivative of an antibody to synuclein. In some methods, the patient is asymptomatic. In some methods, the patient has the disease and is asymptomatic. In some methods the patient has a risk factor for the disease and is asymptomatic. In some methods, the disease is Parkinson's disease. In some methods, the disease is Parkinson's disease, and the administering the agent improves motor characteristics of the patient. In some methods, the disease is Parkinson's disease administering the agent prevents deterioration of motor characteristics of the patient. In some methods, the patient is free of Alzheimer's disease.

For treatment of patients suffering from Lewy bodies or alpha-SN aggregation in the brain, one treatment regime entails administering a dose of alpha-SN or an active fragment thereof to the patient to induce the immune response. In some methods the alpha-SN or an active fragment thereof is administered in multiple doses over a period of at least six months. The alpha-SN or an active fragment thereof can be administered, for example, peripherally, intraperitoneally, orally, subcutaneously, intracranially, intramuscularly, topically, intranasally or intravenously. In some methods, the alpha-SN or an active fragment thereof is administered with an adjuvant that enhances the immune response to the alpha-SN or an active fragment thereof. In some methods, the immunogenic response comprises antibodies to alpha-SN or an active fragment thereof.

In some methods, the agent is amino acids 35-65 of alpha-SN. In some methods, the agent comprises amino acids 130-140 of alpha-SN and has fewer than 40 amino acids total, or fewer than 30 amino acids total. In some methods, the agent comprises amino acids 130-136 of alpha-SN and has fewer than 40 amino acids total, or fewer than 30 amino acids total. In some methods, the C-terminal amino acids of the agent are the C-terminal amino acid of alpha-SN. In some of the above methods, the alpha-SN or active fragment is linked to a carrier at the N-terminus of the alpha-SN or active fragment.

In some methods, the agent comprises amino acids 91-99 of alpha-SN and has fewer than 40 amino acids total, or fewer than 30 amino acids total. In some methods, the agent comprises amino acids 118-126 of alpha-SN and has fewer than 40 amino acids total, or fewer than 30 amino acids total. In some methods, the agent comprises amino acids 1-10 of alpha-SN and has fewer than 40 amino acids total, or fewer than 30 amino acids total. In some methods, the N-terminal amino acids of the agent are the N-terminal amino acid of alpha-SN. In some of the above methods, the alpha-SN or active fragment is linked to a carrier at the C-terminus of alpha-SN or active fragment. In some of the above methods, the alpha-SN or active fragment is linked to a carrier molecule to form a conjugate.

In some methods, the agent is administered to a patient by administering a polynucleotide that encodes a polypeptide comprising an alpha-SN fragment.

For treatment of patients suffering from Lewy bodies or alpha-SN aggregation in the brain, one treatment regime entails administering a dose of an antibody to alpha-SN or an active fragment thereof to the patient to induce the immune response. The antibody used can be human, humanized, chimeric, or polyclonal and can be monoclonal or polyclonal. In some methods the isotype of the antibody is a human IgG1. In some methods, the antibody is prepared from a human immunized with alpha-SN peptide and the human can be the patient to be treated with antibody. In some methods, the antibody binds to the outer surface of neuronal cells having Lewy bodies thereby dissipating the Lewy bodies. In some methods, the antibody is internalized within neuronal cells having Lewy bodies thereby dissipating the Lewy bodies.

In some methods, the antibody is administered with a pharmaceutical carrier as a pharmaceutical composition. In some methods, antibody is administered at a dosage of 0.0001 to 100 mg/kg, preferably, at least 1 mg/kg body weight antibody. In some methods the antibody is administered in multiple doses over a prolonged period, for example, at least six months. In some methods antibodies can be administered as a sustained release composition. The antibody can be administered, for example, peripherally, intraperitoneally, orally, subcutaneously, intracranially, intramuscularly, topically, intranasally or intravenously. In some methods, the patient is monitored for level of administered antibody in the blood of the patient.

In some methods, the antibody is administered by administering a polynucleotide encoding at least one antibody chain to the patient. The polynucleotide is expressed to produce the antibody chain in the patient. Optionally, the polynucleotide encodes heavy and light chains of the antibody and the polynucleotide is expressed to produce the heavy and light chains in the patient.

This invention further provides pharmaceutical compositions comprising any of the antibodies to alpha-SN described in this application and a pharmaceutically acceptable carrier.

In another aspect, the invention provides methods of preventing or treating a disease characterized by Lewy bodies or alpha-SN aggregation in the brain comprising administering an agent that induces an immunogenic response against alpha-SN, and further comprising administering of a second agent that induces an immunogenic response against Aβ to the patient. In some methods, the agent is Aβ or an active fragment thereof. In some methods, the agent is an antibody to Aβ.

In another aspect, the invention provides methods of preventing or treating a disease characterized by Lewy bodies or alpha-SN aggregation in the brain comprising administering an agent that induces an immunogenic response against Aβ to a patient. In some methods, the agent is Aβ or an active fragment thereof. In some methods, the agent is an antibody to Aβ. In some methods the disease is Parkinson's disease. In some methods, the patient is free of Alzheimer's disease and has no risk factors thereof. In some methods, further comprise monitoring a sign or symptom of Parkinson's disease in the patient. In some methods, the disease is Parkinson's disease and administering the agent results in improvement in a sign or symptom of Parkinson's disease.

This invention further provides pharmaceutical compositions comprising an agent effective to induce an immunogenic response against a component of a Lewy body in a patient, such as described above, and a pharmaceutically acceptable adjuvant. In some compounds, the agent is alpha-SN or an active fragment, for example, NAC, or any of the fragments described in the application. The invention also provides pharmaceutical compositions comprising an antibody specific for a component of a Lewy body.

This invention also provides pharmaceutical compositions comprising an agent effective to elicit an immune response against a synuclein-NAC component of an amyloid plaque in a patient. In some compounds, the agent is alpha-SN or an active fragment, for example, NAC, or any of the fragments of alpha synuclein described in the application, and, optionally, an adjuvant. In other compounds, the agent is an antibody or fragment thereof that specifically binds alpha-SN or a fragment thereof, and, optionally, a pharmaceutical carrier.

In another aspect, the invention provides for methods of screening an antibody for activity in preventing or treating a disease associated with Lewy bodies. Such methods entail, contacting a neuronal cell expressing synuclein with the antibody. Then one determines whether the contacting reduces synuclein deposits in the cells compared with a control cells not contacted with the antibody.

In another aspect, the invention provides for methods of screening an antibody for activity in treating or preventing a Lewy body disease in the brain of a patient. Such methods entail contacting the antibody with a polypeptide comprising at least five contiguous amino acids of alpha-SN. Then one determines whether the antibody specifically binds to the polypeptide, specific binding providing an indication that the antibody has activity in treating the disease.

The invention further provides methods of effecting prophylaxis or treating a disease characterized by Lewy bodies or alpha-synuclein aggregation in the brain. The method comprises administering to a patient having or at risk of the disease a polypeptide comprising an immunogenic fragment of alpha-synuclein effective to induce an immunogenic response comprising antibodies that specifically bind to an epitope within residues 70-140 of human alpha-synuclein, residues being numbered according to SEQ ID NO:1, thereby effecting prophylaxis or treatment of the disease.

Optionally, the immunogenic fragment of alpha-synuclein is free of residues 1-69 of alpha synuclein, residues being numbered according to SEQ ID NO:1. Optionally, the immunogenic response comprises antibodies that specifically binds to human alpha synuclein within an epitope selected from the group consisting of SN83-101, SN107-125, SN110-128 and SN124-140, residues being numbered according to SEQ ID NO:1. Optionally, the immunogenic response is free of antibodies that specifically bind to residues of human alpha synuclein outside the selected epitope. Optionally, the immunogenic fragment has from 5-20, 5-25 or 5-30 contiguous amino acids from between positions 70-140 of alpha synuclein, residues being numbered according to SEQ ID NO:1. Optionally, the immunogenic fragment has from 5-20 contiguous amino acids from between positions 120-140 of alpha synuclein, residues being numbered according to SEQ ID NO:1. Optionally, the immunogenic fragment comprises a segment of human alpha synuclein selected from the group consisting of SN87-97, SN111-121, SN114-124 and SN128-136, and contains no more than 40, or no more than 30, contiguous residues in total of alpha synuclein, residues being numbered according to SEQ ID NO:1. Optionally, the immunogenic fragment comprises a segment of human alpha synuclein selected from the group consisting of SN 124-134, SN 91-99 and SN 118-126 and contains no more than 40, or no more than 30, contiguous residues in total of alpha synuclein, residues being numbered according to SEQ ID NO:1 Optionally, the immunogenic fragment comprises SN125-140 and contains no more than 40, or no more than 30, contiguous residues in total of alpha synuclein, residues being numbered according to SEQ ID NO:1. Optionally, the immunogenic fragment comprises SN130-140 and contains no more than 40, or no more than 30, contiguous residues in total of alpha synuclein, residues being numbered according to SEQ ID NO:1. Optionally, the immunogenic fragment comprises SN83-140, residues being numbered according to SEQ ID NO:1.

Optionally, the immunogenic fragment is selected from a group consisting of SN124-140, SN125-140, SN126-140, SN127-140, SN128-140, SN 129-140, SN130-140, SN131-140, SN132-140, SN133-140, SN134-140, SN135-140, SN136-140, SN137-140, SN124-139, SN125-139, SN126-139, SN127-139, SN128-139, SN124-139, SN125-139, SN126-139, SN127-139, SN128-139, SN 129-139, SN130-139, SN131-139, SN132-139, SN133-139, SN134-139, SN135-139, SN136-139, SN137-139, SN124-138, SN124-138, SN125-138, SN126-138, SN127-138, SN128-138, SN 129-138, SN130-138, SN131-138, SN132-138, SN133-138, SN134-138, SN135-138, SN136-138, SN124-137, SN125-137, SN126-137, SN127-137, SN128-137, SN 129-137, SN130-137, SN131-137, SN132-137, SN133-137, SN134-137, SN135-137, SN124-136, SN125-136, SN126-136, SN127-136, SN128-136, SN 129-136, SN130-136, SN131-136, SN132-136, SN133-136, and SN134-136, residues being numbered according to SEQ ID NO:1.

Optionally, the immunogenic response comprises antibodies that specifically bind to human alpha synuclein within an epitope selected from the group consisting of SN1-20, SN2-21, SN2-23 and SN1-40, residues being numbered according to SEQ ID NO:1. Optionally, the immunogenic response is free of antibodies that specifically bind to residues of human alpha synuclein within the region SN25-69, SN25-140, SN40-69, SN40-140, or SN70-140. Optionally, the immunogenic fragment has from 5-20, 5-25 or 5-30 contiguous amino acids from between positions 1-40 of alpha synuclein, residues being numbered according to SEQ ID NO:1.

Optionally, the immunogenic fragment has from 5-20 contiguous amino acids from between positions 1 and 20 and from 5-20 contiguous amino acids from between positions 120 and 140 of alpha synuclein, residues being numbered according to SEQ ID NO:1. Optionally the immunogenic fragment contains no more than 40, or no more than 30, contiguous residues in total of alpha synuclein, residues being numbered according to SEQ ID NO:1.

Optionally, the immunogenic response comprises antibodies that specifically bind to human alpha synuclein within an epitope within residues 1-20 of human alpha-synuclein and within an epitope within residues 70-140 of human alpha-synuclein. Optionally, the immunogenic response comprises antibodies that specifically binds to human alpha synuclein within an epitope within residues 1-20 of human alpha-synuclein and within an epitope within residues 120-140 of human alpha-synuclein. Optionally, the immunogenic response does not comprise antibodies that specifically bind to human alpha synuclein within an epitope within residues 41 and 119 of human alpha-synuclein.

Optionally, the immunogenic fragment is linked to a carrier to form a conjugate. Optionally, the polypeptide comprises the immunogenic fragment fused to the carrier. Optionally, the immunogenic fragment is linked to the carrier molecule at the C-terminus of the alpha-synuclein fragment. Optionally, multiple copies of the fragment are interlinked with multiple copies of the carrier. Optionally, the immunogenic fragment is administered with an adjuvant. Optionally, the administering step effects at least partial clearance of Lewy Bodies. Optionally, the administering step disaggregates Lewy Bodies. Optionally, the administering step reduces levels of alpha synuclein oligomers in synapses. Optionally, the administering step clears synuclein by activation of a lysosomal pathway.

Optionally the immunogenic response is induced by administration of a single polypeptide or fusion protein. Optionally the immunogenic response is induced by administration of more than one polypeptide (e.g., two polypeptides). Optionally the immunogenic response is induced by administration of a first polypeptide comprising a first immunogenic fragment of alpha-synuclein effective to induce an immunogenic response comprising antibodies that specifically bind to an epitope within residues 1-20 of human alpha-synuclein, and administering a polypeptide comprising a second immunogenic fragment of alpha-synuclein effective to induce an immunogenic response comprising antibodies that specifically bind to an epitope within residues 70-140, and preferably residues 120-140, of human alpha-synuclein.

Optionally, the immunogenic response is induced by administration of two or more polypeptides in combination. Optionally the two or more polypeptides are co-administered and/or co-formulated.

In another aspect, the invention provides a composition comprising a first polypeptide comprising a first immunogenic fragment of alpha-synuclein and a second polypeptide comprising a second immunogenic fragment of alpha-synuclein, where the first immunogenic fragment is effective to induce an immunogenic response comprising antibodies that specifically bind to an epitope within residues 1-20 of human alpha-synuclein and the second immunogenic fragment of alpha-synuclein is effective to induce an immunogenic response comprising antibodies that specifically bind to an epitope within residues 120-140 of human alpha-synuclein. Optionally the composition is free of an immunogenic fragment of alpha-synuclein comprising residues 25-69 of alpha-synuclein. The first and second immunogenic fragments can be physically linked (e.g., as a conjugate or fusion protein). The first and second immunogenic fragments can be coformulated.

The invention further provides methods of effecting prophylaxis or treating a disease characterized by Lewy bodies or alpha-synuclein aggregation in the brain. In one embodiment the methods comprise administering to a patient having or at risk of the disease an effective regime of an antibody that specifically binds to an epitope within residues 70-140 of human alpha-synuclein, residues being numbered according to SEQ ID NO:1. When the antibody specifically binds to an epitope within residues 70-140 of human alpha-synuclein, residues being numbered according to SEQ ID NO:1, optionally, the antibody specifically binds to an epitope within residues 83-140 of human alpha synuclein, residues being numbered according to SEQ ID NO:1. Optionally, the antibody specifically binds to an epitope within residues 120-140 of human alpha synuclein. Optionally, the antibody specifically binds within an epitope within a segment of human alpha synuclein selected from the group consisting of SN83-101, SN107-125, SN110-128, SN 118-126, SN 91-99, SN 124-134 and SN124-140, residues being numbered according to SEQ ID NO:1.

In another embodiment the methods comprise administering to a patient having or at risk of the disease an effective regime of an antibody that specifically binds to an epitope within residues 1-40 of human alpha-synuclein, residues being numbered according to SEQ ID NO:1. When the antibody specifically binds to an epitope within residues 1-40 of human alpha-synuclein, residues being numbered according to SEQ ID NO:1, optionally the antibody specifically binds to an epitope within residues 1-20, or within residues 1-10, residues being numbered according to SEQ ID NO:1.

In still another embodiment the methods comprise administering to a patient having or at risk of the disease an effective regime of a first antibody that specifically binds to an epitope within residues 1-40 of human alpha-synuclein and a second antibody that specifically binds to an epitope within residues 70-140 of human alpha-synuclein, residues being numbered according to SEQ ID NO:1.

When a first antibody that specifically binds to an epitope within residues 1-40 of human alpha-synuclein and a second antibody that specifically binds to an epitope within residues 70-140 of human alpha-synuclein, residues being numbered according to SEQ ID NO:1, optionally the second antibody specifically binds to an epitope within residues 120-140 of human alpha-synuclein. Optionally the first antibody and second antibody are administered simultaneously. Optionally the first antibody and second antibody are administered in the same course of treatment.

Optionally, the antibody is a monoclonal antibody. Optionally, the antibody is a polyclonal population of antibodies lacking specific binding to residues of alpha synuclein outside the epitope. Optionally, the antibody is a humanized antibody. Optionally, the antibody is human antibody. Optionally, the antibody is an antibody of human IgG1 isotype. Optionally, the antibody is administered with a pharmaceutical carrier as a pharmaceutical composition. Optionally, the antibody is administered at a dosage of 0.0001 to 100 mg/kg, preferably, at least 1 mg/kg body weight antibody. Optionally, the antibody is administered in multiple dosages over at least six months. Optionally, the antibody is administered as a sustained release composition. Optionally, the antibody is administered intraperitoneally, orally, subcutaneously, intracranially, intramuscularly, topically, intranasally or intravenously. Optionally, the antibody is internalized within neuronal cells having Lewy bodies thereby dissipating the Lewy bodies. Optionally, the antibody binds to the outer surface of neuronal cells having Lewy bodies thereby dissipating the Lewy bodies. Optionally, the antibody binds to alpha synuclein on the outer surface of neuronal cells promoting crosslinking of the alpha synuclein. wherein the administering step disaggregates Lewy bodies. Optionally, the administering step reduces levels of human alpha synuclein oligomers in synapses. Optionally, the administering step clears human alpha synuclein by activation of a lysosomal pathway. In some methods, the disease is Parkinson's disease. Optionally, the antibody specifically binds to denatured human alpha-synuclein as determined by immunoblot. Optionally, the antibody specifically binds to denatured human alpha-synuclein with an affinity of at least $10^9$ $M^{-1}$. Optionally, the antibody specifically binds to synapses as determined by immunocytochemistry.

The invention also provides a composition for prophylaxis or treatment of a disease characterized by Lewy bodies or alpha-synuclein aggregation in the brain, comprising a first monoclonal antibody that specifically binds to an epitope within residues 1-20 of human alpha-synuclein and a second monoclonal antibody that specifically binds to an epitope within residues 70-140 (and preferably residues 120-140) of human alpha-synuclein, residues being numbered according to SEQ ID NO:1.

The invention also provides a kit for prophylaxis or treatment of a disease characterized by Lewy bodies or alpha-synuclein aggregation in the brain, comprising a first container comprising an antibody that specifically binds to an epitope within residues 1-20 of human alpha-synuclein and a second container comprising an antibody that that specifically binds to an epitope within residues 70-140 (and preferably residues 120-140) of human alpha-synuclein, residues being numbered according to SEQ ID NO:1.

The invention further provides methods of effecting prophylaxis or treating a disease characterized by Lewy bodies or alpha-synuclein aggregation in the brain. The methods comprise administering to a patient suffering from or at risk of the disease an effective regime of an agent that induces an immunogenic response comprising antibodies that specifically bind to an epitope within residues 70-140 of human alpha synuclein, residues being numbered according to SEQ ID NO:1, thereby effecting prophylaxis or treating the disease. Optionally, the immunogenic response is free of antibodies that specifically bind to an epitope within residues 1-69 of human alpha synuclein, residues being numbered according to SEQ ID NO:1. Optionally, the immunogenic response comprises antibodies that specifically bind within a segment of human alpha synuclein selected from the group consisting of SN83-101, SN107-125, SN110-128, SN 118-126, SN 91-99, SN 124-134 and SN124-140, residues being numbered according to SEQ ID NO:1.

The invention further provides methods of screening for an agent has activity useful in treating a disease characterized by Lewy Bodies. The methods comprise contacting the agent with a transgenic nonhuman animal disposed to develop a characteristic of a Lewy Body disease with the agent; and determining whether the agent affects the extent or rate of development of the characteristic relative to a control transgenic nonhuman animal. The agent is (i) an fragment of alpha synuclein that induces antibodies that specifically bind to at least one epitope within residues 70-140 of human alpha synuclein or (ii) an antibody that specifically binds to an epitope with residues 70-140 of human alpha synuclein, residues being numbered according to SEQ ID NO:1.

Optionally, the transgenic nonhuman animal comprises a transgene expressing human alpha-synuclein. Optionally, the method further comprises screening a plurality of test antibodies for binding to denatured human alpha synuclein, and selecting the highest binding antibody as the agent. Optionally, the method further comprises screening a plurality of test antibodies for binding to deposits of synuclein in a tissue section by immunocytochemistry, and selecting the highest binding antibody as the agent.

The invention further provides a method of humanizing a monoclonal antibody selected from 8A5, 6H7, 9E4, 1H7, and 11A5 comprising: determining the amino acid sequence of CDR regions of the monoclonal antibody; selecting an acceptor antibody; and producing a humanized antibody comprising the CDRs from the monoclonal antibody and variable region frameworks from the acceptor antibody.

The invention further provides a method of producing a chimeric form of a monoclonal antibody selected from 8A5, 6H7, 9E4, 1H7, and 11A5, comprising: determining the amino acid sequence of the light and heavy chain variable regions of the monoclonal antibody; selecting heavy and light chain constant region; producing a chimeric antibody comprising a light chain comprising the light chain variable region fused to the light chain constant region, and a heavy chain comprising the heavy chain variable region fused to the heavy chain constant region.

The invention provides methods of effecting prophylaxis or treating a disease characterized by Lewy bodies or alpha-synuclein aggregation in the brain, the method comprising administering to a patient having or at risk of the disease an effective regime of an antibody that specifically binds to an epitope within residues 110-130 of human alpha-synuclein, residues being numbered according to SEQ ID NO:1. Optionally, the antibody binds to an epitope within residues 118-126 of human alpha-synuclein. Optionally the disease is Parkinson's disease. Optionally, the antibody is a monoclonal antibody. Optionally, the antibody is a chimeric antibody, a human antibody, or a humanized antibody. Optionally, the antibody competes with mouse monoclonal antibody 9E4 (ATCC accession number PTA-8221) for binding to human alpha-synuclein. Optionally, the antibody is monoclonal antibody 9E4 (ATCC accession number PTA-8221) or humanized or chimeric 9E4. Optionally, the antibody is an antibody of human IgG1 isotype. Optionally, the antibody is administered with a pharmaceutical carrier as a pharmaceutical composition. Optionally, the antibody is administered at a dosage of 0.0001 to 100 mg antibody/kg body weight. Optionally, the antibody is administered in multiple dosages over at least six months. Optionally, the antibody is administered intraperitoneally, orally, subcutaneously, intracranially, intramuscularly, topically, intranasally or intravenously. Optionally, the antibody is administered by a peripheral route. Optionally, the antibody is administered at a dose of 1-10 mg/kg.

The invention further provides a monoclonal antibody 9E4 (ATCC accession number PTA-8221) or humanized or chimeric 9E4.

The invention further provides a method of humanizing monoclonal antibody 9E4 (ATCC accession number PTA-8221) comprising: determining the amino acid sequence of CDR regions of the monoclonal antibody; selecting an acceptor antibody; and producing a humanized antibody comprising the CDRs from the monoclonal antibody and variable region frameworks from the acceptor antibody.

The invention further provides a method of producing a chimeric form of monoclonal antibody 9E4 (ATCC accession number PTA-8221), comprising: determining the amino acid sequence of the light and heavy chain variable regions of the monoclonal antibody; selecting heavy and light chain constant region; and producing a chimeric antibody comprising a light chain comprising the light chain variable region fused to the light chain constant region, and a heavy chain comprising the heavy chain variable region fused to the heavy chain constant region.

The invention further provides an anti-synuclein monoclonal antibody produced by hybridoma JH17.9E4.3.37.1.14.2 (ATCC accession number PTA-8221), hybridoma JH17.1H7.4.24.34 (ATCC accession number PTA-8220), or hybridoma JH22.11A5.6.29.70.54.16.14 (ATCC accession number PTA-8222).

The invention further provides a chimeric or humanized antibody of a monoclonal antibody produced by hybridoma JH17.1H7.4.24.34 (ATCC accession number PTA-8220), or hybridoma JH22.11A5.6.29.70.54.16.14 (ATCC accession number PTA-8222).

The invention further provides a method of humanizing a monoclonal antibody produced by hybridoma JH17.1H7.4.24.34 (ATCC accession number PTA-8220), or hybridoma JH22.11A5.6.29.70.54.16.14 (ATCC accession number PTA-8222) comprising: determining the amino acid sequence of CDR regions of the monoclonal antibody; selecting an acceptor antibody; and producing a humanized antibody comprising the CDRs from the monoclonal antibody and variable region frameworks from the acceptor antibody.

The invention further provides a method of producing a chimeric form of a monoclonal antibody produced by hybridoma JH17.1H7.4.24.34 (ATCC accession number PTA-8220), or hybridoma JH22.11A5.6.29.70.54.16.14 (ATCC accession number PTA-8222), comprising: determining the amino acid sequence of the light and heavy chain variable regions of the monoclonal antibody; selecting heavy and light chain constant region; producing a chimeric antibody comprising a light chain comprising the light chain variable region fused to the light chain constant region, and a heavy chain comprising the heavy chain variable region fused to the heavy chain constant region.

The invention further provides a cell of hybridoma JH17.9E4.3.37.1.14.2 (ATCC accession number PTA-8221), hybridoma JH17.1H7.4.24.34 (ATCC accession number PTA-8220), or hybridoma JH22.11A5.6.29.70.54.16.14 (ATCC accession number PTA-8222).

The invention further provides a use of an antibody that specifically binds to an epitope within residues 110-130 of human alpha-synuclein, residues being numbered according to SEQ ID NO:1 in the manufacture of a medicament to treat a disease characterized by Lewy bodies or alpha synuclein aggregation whereby the antibody is administered by a peripheral route, and reduces intracellular Lewy bodies or alpha synuclein aggregation by a lysosomal pathway. Optionally, the antibody enters a cell containing a Lewy body or alpha synuclein aggregation by endocytosis. Optionally, the antibody binds to membrane bound alpha synuclein from the exterior of the cell and a complex of antibody and alpha synuclein are endocytosed into the cell and combine with a lysosome within the cell. Optionally, the antibody and alpha synculein are separately endocytosed and combined with a lysosome within the cell.

The invention further provides a method of effecting prophylaxis or treating a disease characterized by Lewy bodies or alpha-synuclein aggregation in the brain, the method comprising administering to a patient having or at risk of the disease an effective regime of an agent that induces an antibody that specifically binds to an epitope within residues 110-130 of human alpha-synuclein, residues being numbered according to SEQ ID NO:1. Optionally, the agent is a fragment of alpha-synuclein. Optionally, the fragment has no more than 30 contiguous residues total of alpha-synuclein. Optionally, the fragment induces an antibody to an eptiope within residues 118-126 of alpha-synuclein. Optionally, the fragment comprises residues 118-126 of alpha synuclein. Optionally, the fragment is linked to a carrier.

BRIEF DESCRIPTION OF THE DRAWINGS

FIG. 1 shows the amino acid sequence of alpha-SN (SEQ ID: 1) in alignment with two NAC amino acid sequences, SEQ ID NO: 2 and SEQ ID NO: 3, respectively.

FIG. 2 shows immunohistostained brain sections from nontransgenic mice (panels A, E, and I), alpha-SN transgenic mice immunized with adjuvant alone (panels B, F, J), and alpha-SN transgenic mice immunized with alpha-SN which developed low titers (panels C, G, and K) and high titers (panels D, H, and I) of antibodies to alpha-SN. Sections were subjected to staining with an anti-alpha-synulcein antibody to detect synuclein levels (panels A-D), an anti-IgG antibody to determine total IgG levels present in the section (panels E-H), and for Glial Fibrillary Acidic Protein (GFAP), a marker of astroglial cells.

DEFINITIONS

Figure 3:
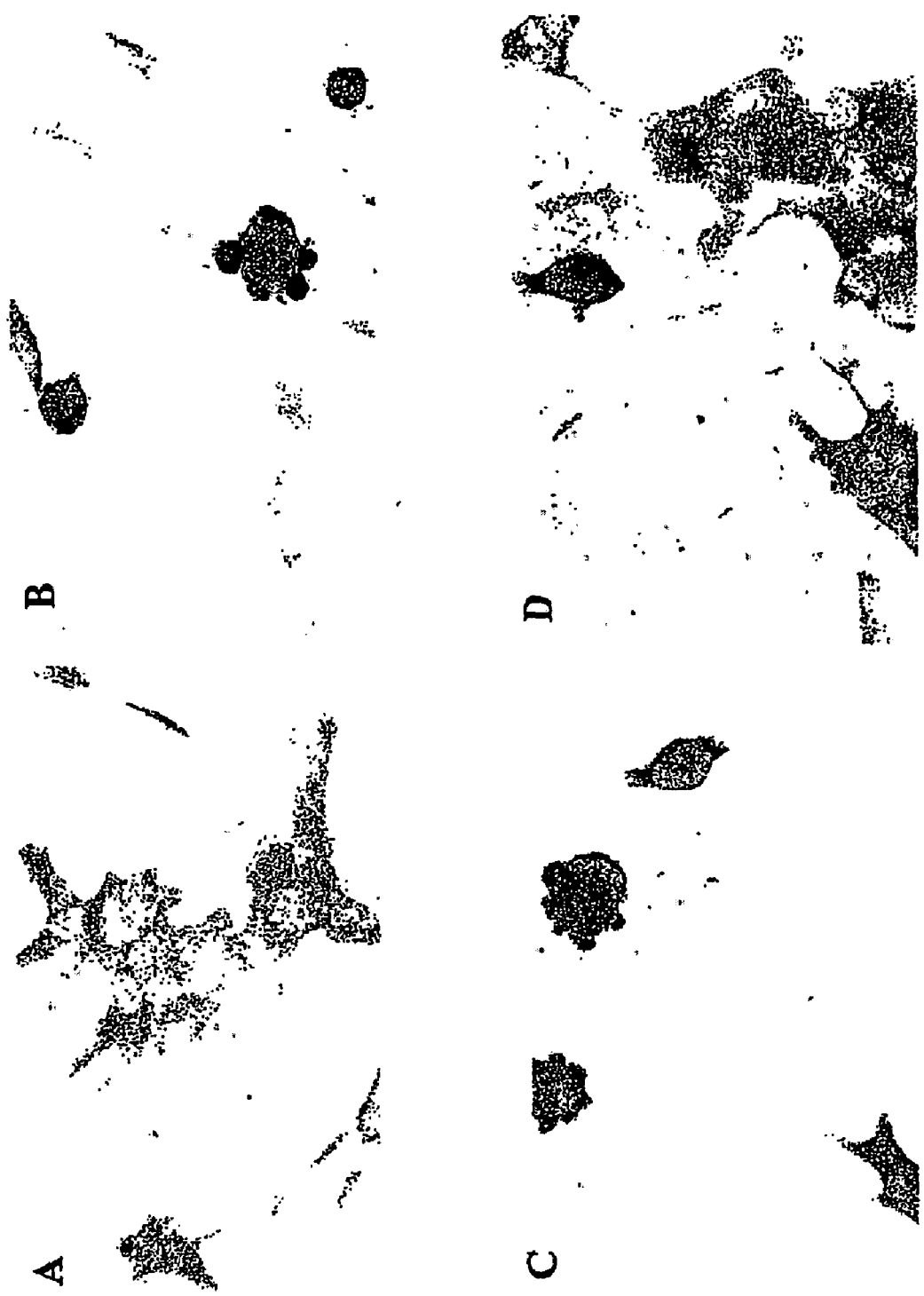
FIGS. 3A-D show the effects of anti-mSYN polyclonal antibody on synuclein aggregation in transfected GT1-7 cells as seen by light microscopy.

The term "substantial identity" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity or higher). Preferably, residue positions which are not identical differ by conservative amino acid substitutions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra). One example of algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (NCBI) website. Typically, default program parameters can be used to perform the sequence comparison, although customized parameters can also be used. For amino acid sequences, the BLASTP program uses as defaults a word length (W) of 3, an expectation (E) of 10, and the BLOSUM62 scoring matrix (see Henikoff & Henikoff, *Proc. Natl. Acad. Sci. USA* 89, 10915 (1989)).

For purposes of classifying amino acids substitutions as conservative or non-conservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Therapeutic agents of the invention are typically substantially pure from undesired contaminant. This means that an agent is typically at least about 50% w/w (weight/weight) purity, as well as being substantially free from interfering proteins and contaminants. Sometimes the agents are at least about 80% w/w and, more preferably at least 90 or about 95% w/w purity. However, using conventional protein purification techniques, homogeneous peptides of at least 99% w/w can be obtained.

The phrase that a molecule "specifically binds" to a target refers to a binding reaction which is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) *Antibodies, A Laboratory Manual*, Cold Spring Harbor Publications, New York, for a description of immunoassay formats and conditions that can be used to determine specific immunoreactivity. Specific binding between two entities means an affinity of at least $10^6$, $10^7$, $10^8$, $10^9$ $M^{-1}$, or $10^{10}$ $M^{-1}$. Affinities greater than $10^8$ $M^{-1}$ are preferred.

The term "antibody" or "immunoglobulin" is used to include intact antibodies and binding fragments thereof. Typically, fragments compete with the intact antibody from which they were derived for specific binding to an antigen. Fragments include separate heavy chains, light chains, Fab, Fab' F(ab')$_2$, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992). The term "antibody" also includes single-chain antibodies in which heavy and light chain variable domains are linked through a spacer.

APP$^{695}$, APP$^{751}$, and APP$^{770}$ refer, respectively, to the 695, 751, and 770 amino acid residue long polypeptides encoded by the human APP gene. See Kang et al., *Nature* 325, 773 (1987); Ponte et al., *Nature* 331, 525 (1988); and Kitaguchi et al., *Nature* 331, 530 (1988). Amino acids within the human amyloid precursor protein (APP) are assigned numbers according to the sequence of the APP770 isoform. Terms such as Aβ39, Aβ40, Aβ41, Aβ42 and Aβ43 refer to an Aβ peptide containing amino acid residues 1-39, 1-40, 1-41, 1-42 and 1-43.

An "antigen" is an entity to which an antibody specifically binds.

The term "epitope" or "antigenic determinant" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., *J. Inf. Dis.* 170, 1110-19 (1994)), by antigen-dependent killing (cytotoxic T lymphocyte assay, Tigges et al., *J. Immunol.* 156, 3901-3910) or by cytokine secretion.

The term "immunological" or "immune" response is the development of a beneficial humoral (antibody mediated) and/or a cellular (mediated by antigen-specific T cells or their secretion products) response directed against an amyloid peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific CD4$^+$T helper cells and/or CD8$^+$ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays (CD4$^+$ T cells) or CTL (cytotoxic T lymphocyte) assays (see Burke, supra; Tigges, supra). The relative contributions of humoral and cellular responses to the protective or therapeutic effect of an immunogen can be distinguished by separately isolating antibodies and T-cells from an immunized syngeneic animal and measuring protective or therapeutic effect in a second subject.

An "immunogenic agent" or "immunogen" is capable of inducing an immunological response against itself on administration to a mammal, optionally in conjunction with an adjuvant.

The term "all-D" refers to peptides having ≧75%, ≧80%, ≧85%, ≧90%, ≧95%, and 100% D-configuration amino acids.

The term "naked polynucleotide" refers to a polynucleotide not complexed with colloidal materials. Naked polynucleotides are sometimes cloned in a plasmid vector.

The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages.

The term "patient" includes human and other mammalian subjects that receive either prophylactic or therapeutic treatment.

Competition between antibodies is determined by an assay in which the immunoglobulin under test inhibits specific binding of a reference antibody to a common antigen, such as alpha-SN. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242-253 (1983)); solid phase direct biotin-avidin EIA (see Kirkland et al., *J. Immunol.* 137:3614-3619 (1986)); solid phase direct labeled assay, solid phase direct labeled sandwich assay (see Harlow and Lane, *Antibodies, A Laboratory Manual*, Cold Spring Harbor Press (1988)); solid phase direct label RIA using 1-125 label (see Morel et al., *Molec. Immunol.* 25(1):7-15 (1988)); solid phase direct biotin-avidin EIA (Cheung et al., *Virology* 176: 546-552 (1990)); and direct labeled RIA (Moldenhauer et al., *Scand. J. Immunol.* 32:77-82 (1990)). Typically, such an assay involves the use of purified antigen bound to a solid surface or cells bearing either of these, an unlabelled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50% or 75%.

The term "symptom" or "clinical symptom" refers to a subjective evidence of a disease, such as altered gait, as perceived by the patient. A "sign" refers to objective evidence of a disease as observed by a physician.

The phrase "in combination," when referring to administration of two or more anti-human alpha-synuclein antibodies (i.e., each recognizing a different epitope) or administration of two or more polypeptides or immunogens that induce an antibody response against human alpha-synuclein, includes simultaneous administration and administration in the same course of treatment. Simultaneous administration of agents encompasses administration of the agents as a fusion protein or conjugate (e.g., physically linked to each other), a co-formulation (e.g., in which the agents are combined or compounded into a dosage form, e.g., a sustained release or depot formulation), administration as separate compositions within a few minutes or two hours of each other (co-administration), or administration as separate compositions on the same day. Administration in the same course of treatment means both agents are administered to a patient for treatment or prophylaxis of the same condition. Each agent can be administered once or multiple times. For example, one agent might be administered first and the second agent administered the following day or following week. Similarly, the two agents might each be administered more than once, e.g., on sequential days, alternate days, alternate weeks, or according to other schedules (for example, such that the benefit to the patient is expected to exceed that of administration of either agent alone).

A fragment designated in the form SNx-y means a fragment of alpha synuclein that begins at amino acid X and ends at amino acid Y. Such a fragment can be linked to a heterologous polypeptide but not to other amino acids of human alpha synuclein such that the fragment begins before X or ends after Y.

Residues in alpha-synuclein or a fragment thereof are numbered according to SEQ ID NO:1 when alpha-synuclein or the fragment is maximally aligned with SEQ ID NO:1 as described above using default parameters.

Compositions or methods "comprising" one or more recited elements may include other elements not specifically recited. For example, a composition that comprises alpha-SN peptide encompasses both an isolated alpha-SN peptide and alpha-SN peptide as a component of a larger polypeptide sequence.

DETAILED DESCRIPTION OF THE INVENTION

I. General

The invention provides methods of preventing or treating several diseases and conditions characterized by presence of deposits of alpha-SN peptide aggregated to an insoluble mass in the brain of a patient, in the form of Lewy bodies. Such diseases are collectively referred to as Lewy Body diseases (LBD) and include Parkinson's disease (PD). Such diseases are characterized by aggregates of alpha-SN that have a β-pleated sheet structure and stain with thioflavin-S and Congo-red (see Hasimoto, Ibid). The invention provides methods of preventing or treating such diseases using an agent that can generate an immunogenic response to alpha-SN. The immunogenic response acts to prevent formation of, or clear, synuclein deposits within cells in the brain. Although an understanding of mechanism is not essential for practice of the invention, the immunogenic response can induce clearing as a result of antibodies to synuclein that are internalized within cells alone or with alpha synuclein. The results presented in the Examples show that antibodies to alpha synuclein administered peripherally cross the blood brain barrier, and are internalized, either alone or with alpha synuclein, within cells containing alpha synuclein deposits. Internalized antibodies can promote degradation of alpha synuclein via activation of lysosomal pathways. Internalized antibodies with affinity for alpha synuclein in denatured form can also stabilize the molecule in unaggregated form. Alternatively or additionally, antibodies can interfere with aggregation of synuclein on the cell exterior surface. For example, antibodies to alpha-synuclein may recognized and crosslink abnormally conformed proteins in the neuronal cells surface. In some methods, the clearing response can be effected at least in part by Fc receptor mediated phagocytosis. Immunization with synuclein can reduce synuclein accumulation at synapses and neuronal cell bodies in the brain. Although an understanding of mechanism is not essential for practice of the invention, this result can be explained by antibodies to synuclein being taken up by neuronal cells (e.g., by synaptic vesicles).

Optionally, agents generating an immunogenic response against alpha-SN can be used in combination with agents that generate an immunogenic response to Aβ. The immunogenic response is useful in clearing deposits of Aβ in individuals having such deposits (e.g., individuals having both Alzheimer's and Parkinson's disease); however, the immunogenic response also has activity in clearing synuclein deposits. Thus, the present invention uses such agents alone, or in combination with agents generating an immunogenic response to alpha-SN in individuals with LBD but who are not suffering or at risk of developing Alzheimer's disease.

The invention further provides pharmaceutical compositions and methods for preventing and treating amyloidogenic disease. It has been shown that alpha- and beta synuclein are involved in nucleation of amyloid deposits in certain amyloid diseases, particularly Alzheimer's disease. (Clayton, D. F., et al., *TINS* 21(6): 249-255, 1998). More specifically, a fragment of the NAC domain of alpha- and beta-synuclein (residues 61-95) has been isolated from amyloid plaques in Alzheimer's patients; in fact this fragment comprises about 10% of the plaque that remains insoluble after solubilization with sodium dodecyl sulfate (SDS). (George, J. M., et al. Neurosci. News 1: 12-17, 1995). Further, both the full length alpha-SN and the NAC fragment thereof have been reported to accelerate the aggregation of β-amyloid peptide into insoluble amyloid in vitro. (Clayton, supra). The NAC component of amyloid plaques serves as a target for immunologically-based treatments of the present invention, as detailed below. According to one aspect, the invention includes pharmaceutical compositions comprising agents effective to elicit an immune response against a synuclein-NAC component of an amyloid plaque in a patient. Such compositions can be effective in preventing, retarding, or reducing plaque deposition in amyloid disease.

II. Agents Generating an Immunogenic Response Against Alpha Synuclein

An immunogenic response can be active, as when an immunogen is administered to induce antibodies reactive with alpha-SN in a patient, or passive, as when an antibody is administered that itself binds to alpha-SN in a patient.

1. Agents Inducing Active Immune Response

Therapeutic agents induce an immunogenic response specifically directed to certain epitopes within the alpha-SN peptide. Preferred agents are the alpha-SN peptide itself and fragments thereof. U.S. patent publication US20060259986A1 and PCT patent publication WO 05/013889, both of which are incorporated herein by reference for all purposes, disclose novel alpha-synuclein fragments useful in methods of prevention and treatment of synucleinopathic and amyloidogenic disease. Optionally, these fragments can be used in combination with an adjuvant.

Alpha synuclein was originally identified in human brains as the precursor protein of the non-β-amyloid component of (NAC) of AD plaques. (Uéda et al., *Proc. Natl. Acad. Sci. U.S.A.* 90 (23):11282-11286 (1993). Alpha-SN, also termed the precursor of the non-Aβ component of AD amyloid (NACP), is a peptide of 140 amino acids. Alpha-SN has the amino acid sequence:

```
                                    (SEQ ID NO: 1)
MDVFMKGLSKAKEGVVAAAEKTKQGVAEAAGKTKEGVLYVGSKTKEGVVH

GVATVAEKTKEQVTNVGGAVVTGVTAVAQKTVEGAGSIAAATGFVKKDQL

GKNEEGAPQEGILEDMPVDPDNEAYEMPSEEGYQDYEPEA
```

(Uéda et al., Ibid.; GenBank accession number: P37840).

The non-Aβ component of AD amyloid (NAC) is derived from alpha-SN. NAC, a highly hydrophobic domain within alpha synuclein, is a peptide consisting of at least 28 amino acids residues (residues 60-87) (SEQ ID NO: 3) and optionally 35 amino acid residues (residues 61-95) (SEQ ID NO: 2). See FIG. 1. NAC displays a tendency to form a beta-sheet structure (Iwai, et al., *Biochemistry*, 34:10139-10145). Jensen et al. have reported NAC has the amino acid sequence:

```
EQVTNVGGAVVTGVTAVAQKTVEGAGSIAAATGFV   (SEQ ID NO: 2)
```

(Jensen et al., Biochem. J. 310 (Pt 1): 91-94 (1995); GenBank accession number S56746).

Uéda et al. have reported NAC has the acid sequence:

```
KEQVTNVGGAVVTGVTAVAQKTVEGAGS          (SEQ ID NO: 3)
```

(Uéda et al., PNAS USA 90:11282-11286 (1993).

Disaggregated alpha-SN or fragments thereof, including NAC, means monomeric peptide units. Disaggregated alpha-SN or fragments thereof are generally soluble, and are capable of self-aggregating to form soluble oligomers. Oligomers of alpha-SN and fragments thereof are usually soluble and exist predominantly as alpha-helices. Monomeric alpha-SN may be prepared in vitro by dissolving lyophilized peptide in neat DMSO with sonication. The resulting solution is centrifuged to remove any insoluble particulates. Aggregated alpha-SN or fragments thereof, including NAC, means oligomers of alpha-SN or fragments thereof which have associate into insoluble beta-sheet assemblies. Aggregated alpha-SN or fragments thereof, including NAC, means also means fibrillar polymers. Fibrils are usually insoluble. Some antibodies bind either soluble alpha-SN or fragments thereof or aggregated alpha-SN or fragments thereof. Some antibodies bind to oligomers of alpha-synuclein more strongly than to monomeric forms or fibrillar forms. Some antibodies bind both soluble and aggregated alpha-SN or fragments thereof, and optionally oligomeric forms as well.

Alpha-SN, the principal component of the Lewy bodies characteristic of PD, and epitopic fragments thereof, such as, for example, NAC, or fragments other than NAC, such as fragments at or near the N-terminus or at or near the C-terminus can be used to induce an immunogenic response. Preferably such fragments comprise four or more amino acids of alpha-SN or analog thereof.

Other components of Lewy bodies, for example, synphilin-1, Parkin, ubiquitin, neurofilament, beta-crystallin, and epitopic fragments thereof can also be used to induce an immunogenic response.

As noted, certain preferred fragments of alpha-synuclein are from the C-terminal region of the molecule. Such fragments lack residues 1-69 of human alpha-synuclein. Immunization with such fragments generates an immunogenic response comprising antibodies to one or more epitopes within residues 70-140 of human alpha-synuclein. Some active fragments include an epitope at or near the C-terminus of alpha-SN (e.g., within amino acids 70-140, 100-140, 120-140, 130-140, or 135-140). Some active fragments include an epitope at or near the region recognized by monoclonal antibody 8A5. Some active fragments include an epitope at or near the region recognized by monoclonal antibody 9E4 (e.g., within amino acids 90-140, 98-140, 108-136, 110-130 or 118-126). Some active fragments include an epitope at or near the region recognized by monoclonal antibody 1H7 (e.g., within amino acids 70-119, 80-109, 88-101, or 91-99). In some active fragments, the C terminal residue of the epitope is the C-terminal residue of alpha-SN.

Figure 8:
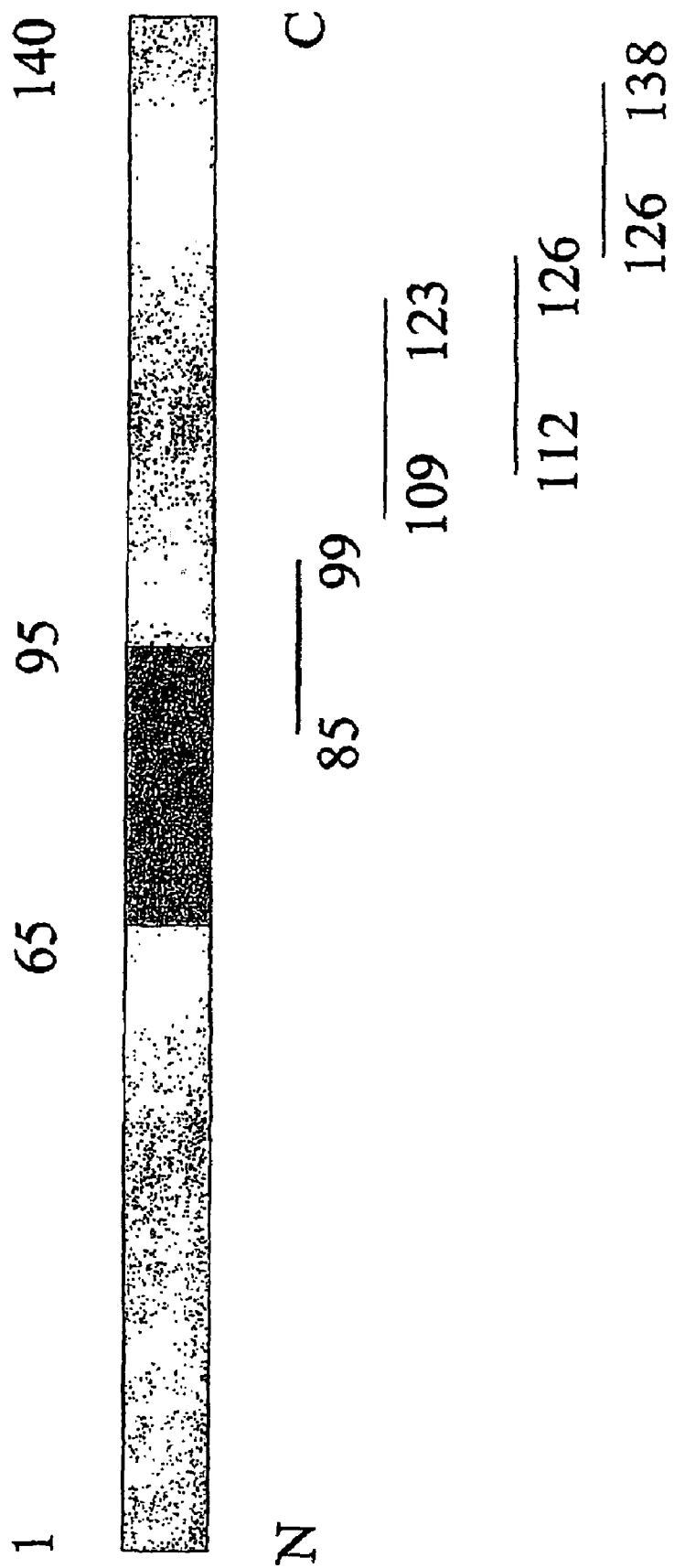
FIG. 8 shows antibody epitope mapping. Antibodies from mice displaying high titers and high affinity anti-human α-synuclein antibodies were mapped using an ELISA technique. In most anti-sera samples from vaccinated mice, epitopes recognized were within the C-terminal region of human α-synuclein. In the sera from CFA treated controls, no epitopes were detected.

Some fragments of alpha synuclein generate antibodies specifically binding to an epitope within one or more of: SN83-101, SN107-125, SN110-128, SN 124-140, SN 110-130, SN 85-105, SN 118-126 and SN 91-99 of human alpha synuclein. Some fragments generate antibodies exclusively specifically binding within one of the above fragments. For example, the fragment SN83-101 begins at residue 83 and ends at residues 101 of alpha-synuclein and generates only antibodies specifically binding to SN83-101. Immunogenic C-terminal region fragments include SN 85-99, SN 109-123, SN 112-126 and SN126-138 (as shown in FIG. 8), SN 110-130, SN 85-105 and other fragments differing from one of these by up to two additional or fewer amino acids at either end. Another preferred fragment SN83-140, which includes all of these epitopes.

Some fragments have no more than 40, or no more than 30, contiguous residues in total from alpha synuclein. Some such fragments comprise SN 125-140, SN130-140, SN 87-97, SN111-121, SN114-124 or SN128-136. Some fragments have a total of 5-20, 5-25 or 5-30 contiguous amino acids from the C-terminal half of alpha synuclein (i.e., residues 70-140). Some fragments have 5-20 contiguous amino acids from between positions 120-140 of alpha synuclein. Particularly preferred fragments include SN124-140, SN125-140, SN126-140, SN127-140, SN128-140, SN 129-140, SN130-140, SN131-140, SN132-140, SN133-140, SN134-140, SN135-140, SN136-140, SN137-140, SN124-139, SN125-139, SN126-139, SN127-139, SN128-139, SN124-139, SN125-139, SN126-139, SN127-139, SN128-139, SN 129-139, SN130-139, SN131-139, SN132-139, SN133-139, SN134-139, SN135-139, SN136-139, SN137-139, SN124-138, SN124-138, SN125-138, SN126-138, SN127-138, SN128-138, SN 129-138, SN130-138, SN131-138, SN132-138, SN133-138, SN134-138, SN135-138, SN136-138, S SN124-137, SN125-137, SN126-137, SN127-137, SN128-137, SN 129-137, SN130-137, SN131-137, SN132-137, SN133-137, SN134-137, SN135-137, SN124-136, SN125-136, SN126-136, SN127-136, SN128-136, SN 129-136, SN130-136, SN131-136, SN132-136, SN133-136, and SN134-136.

Some fragments have 5-20 contiguous amino acids from between positions 118-126, 108-136, and 98-140 of alpha synuclein. Some fragments have 5-20 contiguous amino acids from between positions 70-99, 91-131, 136, or 91-99 of alpha synuclein.

As shown in Examples 1X and X, administration of 6H7, an antibody that recognizes the amino terminus of alpha-synuclein, or of 8A5, an antibody that recognizes the carboxy-terminus of alpha-synuclein, or 9E4, an antibody that recognizes an epitope in the C-terminal region of synuclein, reduced alpha-synuclein aggregation in the brain of transgenic mice over-expressing human alpha-synuclein. It is expected that immunization with alpha-synuclein fragments comprising sequences at or near the alpha-synuclein terminal regions will similarly result in such clearing of aggregates and/or prevent the formation of aggregates.

Other fragments of alpha-synuclein useful for effecting prophylaxis or treating a disease characterized by Lewy bodies or alpha-synuclein aggregation in the brain (e.g., Parkinson's Disease) are from the N-terminal region of the molecule. Immunization with the fragments generates an immunogenic response comprising antibodies to one or more epitopes within residues 1-20 or, in some cases, one or more epitopes within residues 1-10. As shown in Example IX, administration of 6H7, an antibody that recognizes the amino terminus of alpha-synuclein, reduced alpha-synuclein aggregation in the brain of transgenic mice over-expressing human alpha-synuclein. It is expected that immunization with alpha-synuclein fragments comprising the alpha-synuclein amino terminal region will similarly result in such clearing of aggregates and/or prevent the formation of aggregates.

Thus, in an aspect the invention provides a method of effecting prophylaxis or treating a disease characterized by Lewy bodies or alpha-synuclein aggregation in the brain by administering to a patient having or at risk of the disease a polypeptide comprising an immunogenic fragment of alpha-synuclein effective to induce an immunogenic response comprising antibodies that specifically bind to an epitope within residues 1-40, residues 1-20, or residues 1-10 of human alpha-synuclein, residues being numbered according to SEQ ID NO:1. In one embodiment the immunogenic fragment of alpha-synuclein is free of residues 70-140 of alpha synuclein. In one embodiment the immunogenic fragment is free of residues 41-140 of alpha-synuclein. In one embodiment the immunogenic fragment is free of residues 25-140 of alpha-synuclein.

Suitable immunogens for effecting prophylaxis or treating a disease characterized by Lewy bodies or alpha-synuclein aggregation in the brain include, but are not limited to, fragments comprising from 5 to 20 contiguous amino acid residues from the amino terminus of alpha synuclein. In a preferred embodiment the fragment comprises the first (amino-terminal) residue of alpha synuclein. Thus, exemplary fragments include the sequence of residues 1 to $N_a$ of SEQ ID NO.: 1, where $N_a$ is 5 to 20 (e.g., MDVFMKGLSKAKE GVVAAAE (Residues 1-20 of SEQ ID NO: 1); MDVFMKG LSKAKEGVVAAA (Residues 1-19 of SEQ ID NO: 1); MDVFMKGLSKAKEGVVAA (Residues 1-18 of SEQ ID NO: 1); MDVFMKGLSKAKE GVVA (Residues 1-17 of SEQ ID NO: 1); MDVFMKGLSKAKEGVV (Residues 1-16 of SEQ ID NO 1); MDVFMKGLSKAKEGV (Residues 1-15 of SEQ ID NO: 1); MDVFMKGLSKAKEG (Residues 1-14 of SEQ ID NO: 1); MDVFMKGLSKAK (Residues 1-12 of SEQ ID NO: 1); MDVFMKGLSKA (Residues 1-11 of SEQ ID NO: 1); MDVFMKGLSK (Residues 1-10 of SEQ ID NO: 1); MDVFMKGLS (Residues 1-9 of SEQ ID NO: 1); MDVFMKGL (Residues 1-8 of SEQ ID NO: 1); MDVFMKG (Residues 1-7 of SEQ ID NO: 1); MDVFMK (Residues 1-6 of SEQ ID NO: 1); and MDVFM (Residues 1-5 of SEQ ID NO: 1). In other preferred embodiments, the fragment does not comprises the amino-terminal residue of alpha synuclein but comprises at the second and/or third residue of alpha synuclein. Thus, exemplary fragments have the sequence of residues 2 to $N_b$, and 3 to $N_c$ of SEQ ID NO.: 1, where $N_b$ is 6 to 21 and $N_c$ is 7 to 22 (e.g., DVFMKGL-SKAKEGVVAAAEK (Residues 2-21 of SEQ ID NO: 1); DVFM KGLSKAKEGVVAAAE (Residues 2-20 of SEQ ID NO: 1); DVFMKGLSKAKEGVVAAA (Residues 2-19 of SEQ ID NO: 1); DVFMKGLSKAKEGVVAA (Residues 2-18 of SEQ ID NO: 1); DVFMKGLSKAKEGVVA (Residues 2-17 of SEQ ID NO: 1; DVFMKGLSKAKEGVV (Residues 2-16 of SEQ ID NO: 1); DVFMKGLSKAKEGV (Residues 2-15 of SEQ ID NO: 1); DVFMKGLSKAKEG (Residues 2-14 of SEQ ID NO: 1); DVFMKGLSKAK (Residues 3-12 of SEQ ID NO: 1); DVFMKGLSKA (Residues 2-11 of SEQ ID NO: 1); DVFMKGLSK (Residues 2-10 of SEQ ID NO: 1); DVFMKGLS (Residues 2-9 of SEQ ID NO: 1); DVFMKGL (Residues 2-8 of SEQ ID NO: 1); DVFMKG (Residues 2-7 of SEQ ID NO: 1); DVFMK (Residues 2-6 of SEQ ID NO: 1), VFMKGLSKAKEGVVAAAEKT (Residues 3-22 of SEQ ID NO: 1); VFMKGLSKAKEGV-VAAAEK (Residues 3-21 of SEQ ID NO: 1); VFMKGL-SKAKEGVVAAAE (Residues 3-20 of SEQ ID NO: 1); VFMKGL SKAKEGVVAAA (Residues 3-19 of SEQ ID NO: 1); VFMKGLSKAKEGVVAA (Residues 3-18 of SEQ ID NO: 1); VFMKGLSKAKEGVVA (Residues 3-17 of SEQ ID NO: 1); VFMKGLSKAKEGVV (Residues 3-16 of SEQ ID NO: 1); VFMKGLSKAKEGV (Residues 3-15 of SEQ ID NO: 1); VFMKGLSKAKEG (Residues 3-14 of SEQ ID NO: 1); VFMKGLSKAK (Residues 3-12 of SEQ ID NO: 1); VFMKGLSKA (Residues 3-11 of SEQ ID NO: 1); VFMKGLSK (Residues 3-10 of SEQ ID NO: 1); VFMKGLS (Residues 3-9 of SEQ ID NO: 1); VFMKGL (Residues 3-8 of SEQ ID NO: 1); and VFMKG (Residues 3-7 of SEQ ID NO: 1)). As discussed below, the aforementioned fragments may be linked to a carrier molecule (e.g., a conjugate or fusion protein, see Sec. II(3)). Alternatively, as discussed below, an aforementioned fragment may be administered by vaccinating the subject with a nucleic acid encoding the fragment (see Sec. II(4)).

Other fragments of alpha-synuclein useful for effecting prophylaxis or treating a disease characterized by Lewy bodies or alpha-synuclein aggregation in the brain (e.g., Parkinson's Disease) are from the region near serine 129 of alpha-SN. Immunization with fragments including this residue, in its phosphorylated form (e.g., SN 124-134 with Ser129 phosphorylated generates an immunogenic response comprising antibodies to one or more epitopes including phosphoSer129. Some active fragments induce antibodies that recognize an epitope at or near the region recognized by monoclonal antibody 11A5.

For ease of reference, alpha-SN fragments and epitopes can be referred to based on their position in the molecule, for example and without limitation, fragments containing the alpha-SN N-terminal amino acid, fragments containing the C-terminal amino acid, NAC fragments as described above, fragments containing neither the N-terminal amino acid or the C-terminal amino acid, fragments from the C-terminal half of alpha-SN, fragments from the N-terminal half of alpha-SN, fragments within the N-terminal 40 residues of alpha-SN. In certain embodiments fragments can contain from 5 to 100 contiguous residues of alpha-SN, for example in the range bounded by an lower limit of 5, 6, 7, 8, 9, 10, 11, 12, 15, 20, 25, 30 or 40 contiguous residues and an upper limit of 10, 12, 15, 20, 25, 30, 35, 40, 50, or 100 contiguous residues, where the upper limit is higher than the lower limit. Preferably the fragment contains at least 5, at least 8, at least 10, or at least 15 or at least 20 contiguous residues of alpha-SN.

Reference to alpha-SN includes the natural human amino acid sequences indicated above as well as analogs including allelic, species and induced variants, full-length forms and immunogenic fragments thereof. Human alpha synuclein, meaning a protein having the same sequence of amino acids as SEQ ID NO:1 or allelic variants thereof, is preferred in all embodiments. Analogs typically differ from naturally occurring peptides at one, two or a few positions, often by virtue of conservative substitutions. Analogs typically exhibit at least 80 or 90% sequence identity with natural peptides. Positions of amino acids in analogs of natural alpha synuclein are assigned the numbers of corresponding amino acids in natural alpha synuclein when the analog and natural alpha synuclein are maximally aligned. Some analogs also include unnatural amino acids or modifications of N or C terminal amino acids at one, two or a few positions. For example, the natural glutamic acid residue at position 139 of alpha-SN can be replaced with iso-aspartic acid. Examples of unnatural amino acids are D, alpha, alpha-disubstituted amino acids, N-alkyl amino acids, lactic acid, 4-hydroxyproline, gamma-carboxyglutamate, epsilon-N,N,N-trimethyllysine, epsilon-N-acetyllysine, O-phosphoserine, N-acetylserine, N-formylmethionine, 3-methylhistidine, 5-hydroxylysine, omega-N-methylarginine, beta-alanine, ornithine, norleucine, norvaline, hydroxyproline, thyroxine, gamma-amino butyric acid, homoserine, citrulline, and isoaspartic acid. Therapeutic agents also include analogs of alpha-SN fragments. Some therapeutic agents of the invention are all-D peptides, e.g., all-D alpha-SN or all-D NAC, and of all-D peptide analogs. Analogs specifically bind to a polyclonal population of antibodies to natural human alpha synuclein. Fragments and analogs can be screened for prophylactic or therapeutic efficacy in transgenic animal models in comparison with untreated or placebo controls as described below.

Alpha-SN, its fragments, and analogs can be synthesized by solid phase peptide synthesis or recombinant expression, or can be obtained from natural sources. Automatic peptide synthesizers are commercially available from numerous suppliers, such as Applied Biosystems, Foster City, Calif. Recombinant expression can be in bacteria, such as *E. coli*, yeast, insect cells or mammalian cells. Procedures for recombinant expression are described by Sambrook et al., *Molecular Cloning: A Laboratory Manual* (C.S.H.P. Press, NY 2d ed., 1989). Some forms of alpha-SN peptide are also available commercially, for example, at BACHEM and American Peptide Company, Inc.

Therapeutic agents also include longer polypeptides that include, for example, an active fragment of alpha-SN peptide, together with other amino acids. For example, preferred agents include fusion proteins comprising a segment of alpha-SN fused to a heterologous amino acid sequence that induces a helper T-cell response against the heterologous amino acid sequence and thereby a B-cell response against the alpha-SN segment. Such polypeptides can be screened for prophylactic or therapeutic efficacy in animal models in comparison with untreated or placebo controls as described below. The alpha-SN peptide, analog, active fragment or other polypeptide can be administered in associated or multimeric form or in dissociated form therapeutic agents also include multimers of monomeric immunogenic agents. The therapeutic agents of the invention may include polylysine sequences.

In a further variation, an immunogenic peptide, such as a fragment of alpha-SN, can be presented by a virus or bacteria as part of an immunogenic composition. A nucleic acid encoding the immunogenic peptide is incorporated into a genome or episome of the virus or bacteria. Optionally, the nucleic acid is incorporated in such a manner that the immunogenic peptide is expressed as a secreted protein or as a fusion protein with an outer surface protein of a virus or a transmembrane protein of bacteria so that the peptide is displayed. Viruses or bacteria used in such methods should be nonpathogenic or attenuated. Suitable viruses include adenovirus, HSV, Venezuelan equine encephalitis virus and other alpha viruses, vesicular stomatitis virus, and other rhabdo viruses, vaccinia and fowl pox. Suitable bacteria include *Salmonella* and *Shigella*. Fusion of an immunogenic peptide to HBsAg of HBV is particularly suitable.

Therapeutic agents also include peptides and other compounds that do not necessarily have a significant amino acid sequence similarity with alpha-SN but nevertheless serve as mimetics of alpha-SN and induce a similar immune response. For example, any peptides and proteins forming beta-pleated sheets can be screened for suitability. Anti-idiotypic antibodies against monoclonal antibodies to alpha-SN or other Lewy body components can also be used. Such anti-Id antibodies mimic the antigen and generate an immune response to it (see *Essential Immunology*, Roit ed., Blackwell Scientific Publications, Palo Alto, Calif. 6th ed., p. 181). Agents other than alpha-SN should induce an immunogenic response against one or more of the preferred segments of alpha-SN listed above (e.g., NAC). Preferably, such agents induce an immunogenic response that is specifically directed to one of these segments without being directed to other segments of alpha-SN.

Random libraries of peptides or other compounds can also be screened for suitability. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated herein by reference for all purposes). Peptide libraries can also be generated by phage display methods. See, e.g., Devlin, WO 91/18980.

Combinatorial libraries and other compounds are initially screened for suitability by determining their capacity to bind to antibodies or lymphocytes (B or T) known to be specific for alpha-SN or other Lewy body components. For example, initial screens can be performed with any polyclonal sera or monoclonal antibody to alpha-SN or a fragment thereof. The libraries are preferably screened for capacity to bind to antibodies that specifically bind to an epitope within residues 1-20 or 70-140 of human alpha synuclein. Compounds can then be screened for specific binding to a specific epitope within alpha-SN (e.g., SN 1-20, SN 83-101, SN107-125, SN110-128, SN124-140, SN 118-126 and SN 91-99 of alpha synuclein). Compounds can be tested by the same procedures described for mapping antibody epitope specificities. Compounds identified by such screens are then further analyzed for capacity to induce antibodies or reactive lymphocytes to alpha-SN or fragments thereof. For example, multiple dilutions of sera can be tested on microtiter plates that have been precoated with alpha-SN or a fragment thereof and a standard ELISA can be performed to test for reactive antibodies to alpha-SN or the fragment. Compounds can then be tested for prophylactic and therapeutic efficacy in transgenic animals predisposed to a disease associated with the presence of Lewy body, as described in the Examples. Such animals include, for example, transgenic mice over expressing alpha-SN or mutant thereof (e.g., alanine to threonine substitution at position 53) as described, e.g., in WO 98/59050, Masliah, et al., *Science* 287: 1265-1269 (2000), and van der Putter, et al., *J. Neuroscience* 20: 6025-6029 (2000), or such transgenic mice that also over express APP or a mutant thereof. Particularly preferred are such synuclein transgenic mice bearing a 717 mutation of APP described by Games et al., *Nature* 373, 523 (1995) and mice bearing a 670/671 Swedish mutation of APP such as described by McConlogue et al., U.S. Pat. No. 5,612,486 and Hsiao et al., *Science* 274, 99 (1996); Staufenbiel et al., *Proc. Natl. Acad. Sci. USA* 94, 13287-13292 (1997); Sturchler-Pierrat et al., *Proc. Natl. Acad. Sci. USA* 94, 13287-13292 (1997); Borchelt et al, *Neuron* 19, 939-945 (1997)). Examples of such synuclein/APP transgenic animals are provided in WO 01/60794. Additional animal models of PD include 6-hydroxydopamine, rotenone, and 1-methyl-4-phenyl-1,2,3,6-tetrahydropyridine (MPTP) animal models (M. Flint Beal, *Nature Reviews Neuroscience* 2:325-334 (2001)). The same screening approach can be used on other potential analogs of alpha-SN and longer peptides including fragments of alpha-SN, described above and other Lewy body components and analog or fragments thereof.

As described herein, administration of antibodies recognizing epitopes in the amino terminal and carboxy terminal regions of alpha-synuclein (i.e., 8A5 and 6H7) reduced alpha-synuclein aggregates in the brains of transgenic mice over-expressing human alpha-synuclein (see, e.g., Example IX). Based in part on this discovery, it is contemplated that inducing an immune response against epitopes at both termini of alpha-synuclein will have advantages in prophylaxis and therapy. Thus, in one aspect, the invention provides a method for prophylaxis or treatment of a disease characterized by Lewy bodies or alpha-synuclein aggregation in the brain by inducing an immunogenic response comprising antibodies that specifically bind to an epitope within residues 1-20, or alternatively residues 1-10, of human alpha-synuclein and an epitope within residues 70-140 of human alpha-synuclein. In a preferred embodiment the immunogenic response comprises antibodies that specifically bind to an epitope within residues 1-20 of human alpha-synuclein and residues 120-140 of human alpha-synuclein. An immune response that comprises antibodies against epitopes at both terminal regions of the protein can be referred to as a "dual" immune response. A dual immune response can be induced in a number of ways and the present invention is not limited to any particular method of initiating such a response.

A dual immune response can be induced by vaccination with a single polypeptide that is effective to induce an immunogenic response including antibodies that specifically bind to an epitope within residues 1-20 of human alpha-synuclein and antibodies that specifically bind to an epitope within residues 70-140 of human alpha-synuclein. In preferred embodiments the antibodies specifically bind to an epitope within residues 1-10 and/or within residues 120-140 of human alpha-synuclein. A polypeptide lacking at least residues 25-69 of human alpha-synuclein, at least residues 30-110 of human alpha-synuclein, or at least residues 21-119 of human alpha-synuclein can be used. When such polypeptides are used the immunogenic response does not include antibodies that specifically bind to an epitope within residues 25-69 of human alpha-synuclein.

A dual immune response can also be induced by vaccination in combination of two (or more) polypeptides where one polypeptide induces an immunogenic response including antibodies that specifically bind to an epitope within residues 1-20 of human alpha-synuclein and antibodies that specifically bind to an epitope within residues 70-140 of human alpha-synuclein. In preferred embodiments the antibodies specifically bind to an epitope within residues 1-10 and/or within residues 120-140 of human alpha-synuclein. Thus, treatment or prophylaxis can be effected by administering a first immunogenic fragment of alpha-synuclein that induces an immunogenic response comprising antibodies that specifically bind to an epitope within residues 1-20 of human alpha-synuclein and a second immunogenic fragment that induces an immunogenic response comprising antibodies that specifically bind to an epitope within residues 70-140 (or 120-140) of human alpha-synuclein. Fragments of human alpha-synuclein can be administered in combination, as discussed above (e.g., administering as a fusion protein or conjugate, in a co-formulation, or in the same course of therapy).

The invention provides compositions useful for initiating an immune response against epitopes at either or both termini of alpha-synuclein. Compositions include dosage forms and formulations containing two or more polypeptides, such as described above, where one polypeptide induces an immunogenic response including antibodies that specifically bind to an epitope within residues 1-20 of human alpha-synuclein and antibodies that specifically bind to an epitope within residues 70-140 of human alpha-synuclein. In preferred embodiments the polypeptides induce antibodies that specifically bind to an epitope within residues 1-10 and/or within residues 120-140 of human alpha-synuclein. Exemplary formulations (suitable for co-formulating polypeptides) are known in the art and include those described below in Section VII ("Treatment Regimes").

The invention also provides kits for initiating an immune response against epitopes at both termini of alpha-synuclein. The kits include two or more agents that induce an immunogenic response including antibodies that specifically bind to an epitope within residues 1-20 of human alpha-synuclein and antibodies that specifically bind to an epitope within residues 70-140 of human alpha-synuclein. The agents can be combined in a single preparation for simultaneous use. The agents can occupy separate containers (e.g., vials, syringes, tubes, or the like) each containing a different polypeptide for simultaneous, sequential or separate use. These agents of the invention can optionally be administered in combination with other agents that are at least partly effective in treatment of Lewy Body Disease. Kits can also include agents that increase passage of the agents of the invention across the blood-brain barrier, other adjuvants and materials for administration to the patient.

2. Agents for Passive Immune Response

Therapeutic agents of the invention also include antibodies that specifically bind to alpha-SN or other components of Lewy bodies. This invention also provides antibodies that specifically bind to a synuclein-NAC component of an amyloid plaque. Antibodies immunoreactive for alpha-SN are known (see, for example, Arima, et al., Brian Res. 808: 93-100 (1998); Crowther et al., Neuroscience Lett. 292: 128-130 (2000); Spillantini, et al. Nature 388: 839-840 (1997). Such antibodies can be monoclonal or polyclonal. Some such antibodies bind specifically to insoluble aggregates of alpha-SN without specifically binding to the soluble monomeric form. Some specifically bind specifically to the soluble monomeric form without binding to the insoluble aggregated form. Some specifically bind to both aggregated and soluble monomeric forms. Some such antibodies specifically bind to a naturally occurring short form of alpha-SN (e.g., NAC) without binding to a naturally occurring full length alpha-SN. Some antibodies specifically bind to a long form without binding to a short form. Some antibodies specifically bind to alpha-SN without binding to other components of LBs. Some antibodies specifically bind to alpha-SN without specifically binding to other components of amyloid plaques. See U.S. patent publication US20060259986A1 and PCT patent publication WO 05/013889, which are incorporated herein by reference for all purposes, provides end-specific antibodies that specifically bind to fragments of alpha-synuclein without specifically binding to intact alpha-synuclein per se. These antibodies are useful in methods of prevention and treatment of synucleinopathic and amyloidogenic disease.

In experiments carried out in support of the invention, a predictive ex vivo assay (Example VII) was used to test clearing of an antibody that specifically binds to a synuclein-NAC. An antibody to NAC was contacted with a brain tissue sample containing amyloid plaques and microglial cells. Rabbit serum was used as a control. Subsequent monitoring showed a marked reduction in the number and size of plaques indicative of clearing activity of the antibody.

From these data, it is apparent that amyloid plaque load associated with Alzheimer's disease and other amyloid diseases can be greatly diminished by administration of immune reagents directed against epitopes of NAC, which are effective to reduce amyloid plaque load. It is further understood that a wide variety of antibodies can be used in such compositions. As discussed above, U.S. patent publication US20060259986A1 and PCT patent publication WO 05/013889, provides end-specific antibodies that specifically bind to fragments of alpha-synuclein without specifically binding to intact alpha-synuclein per se.

Antibodies used in therapeutic methods usually have an intact constant region or at least sufficient of the constant region to interact with an Fc receptor. Human isotype IgG1 is preferred because of it having highest affinity of human isotypes for the FcRI receptor on phagocytic cells. Bispecific Fab fragments can also be used, in which one arm of the antibody has specificity for alpha-SN, and the other for an Fc receptor. Some antibodies bind to alpha-SN, optionally in a denatured form, such as when treated with SDS, with a binding affinity greater than or equal to about $10^6$, $10^7$, $10^8$, $10^9$, or $10^{10}$ $M^{-1}$. Some antibodies of the invention specifically bind to human alpha synuclein in synapses or neuronal cell bodies as determined by immunocytochemistry.

Polyclonal sera typically contain mixed populations of antibodies binding to several epitopes along the length of alpha-SN. However, polyclonal sera can be specific to a particular segment of alpha-SN, such as NAC. Polyclonal sera that is specific for a particular segment contains antibodies that specifically bind to that segment and lacks antibodies that specifically bind to other segments of alpha-SN. Monoclonal antibodies bind to a specific epitope within alpha-SN that can be a conformational or nonconformational epitope. Nonconformational epitopes remain present when alpha-SN is denatured with SDS. Prophylactic and therapeutic efficacy of antibodies can be tested using the transgenic animal model procedures described in the Examples. some monoclonal antibodies bind to an epitope within NAC. In some methods, multiple monoclonal antibodies having binding specificities to different epitopes are used. Such antibodies can be administered sequentially or simultaneously. Antibodies to Lewy body components other than alpha-SN can also be used. For example, antibodies can be directed to neurofilament, ubiquitin, or synphilin. Therapeutic agents also include antibodies raised against analogs of alpha-SN and fragments thereof. Some therapeutic agents of the invention are all-D peptides, e.g., all-D alpha-SN or all-D NAC.

When an antibody is said to bind to an epitope within specified residues, such as alpha-SN 1-5, for example, what is meant is that the antibody specifically binds to a polypeptide containing the specified residues (i.e., alpha-SN 1-5 in this an example). Such an antibody does not necessarily contact every residue within alpha-SN 1-5. Nor does every single amino acid substitution or deletion with in alpha-SN1-5 necessarily significantly affect binding affinity. Epitope specificity of an antibody can be determined, for example, by forming a phage display library in which different members display different subsequences of alpha-SN. The phage display library is then selected for members specifically binding to an antibody under test. A family of sequences is isolated. Typically, such a family contains a common core sequence, and varying lengths of flanking sequences in different members. The shortest core sequence showing specific binding to the antibody defines the epitope bound by the antibody. Antibodies can also be tested for epitope specificity in a competition assay with an antibody whose epitope specificity has already been determined.

Some antibodies of the invention specifically binds to an epitope within NAC. Some antibodies specifically bind to an epitope within a 22-kilodalton glycosylated form of synuclein, e.g., P22-synuclein (H. Shimura et al., Science 2001 Jul. 13:293(5528):224-5).

Some antibodies of the invention bind to an epitope at the N-terminus of alpha-SN (for example, an epitope within amino acids 1-20 or amino acids 1-10 of alpha-synuclein as numbered according to SEQ ID NO:1). Some antibodies bind to an epitope in which the N-terminal residue of the epitope is the N-terminal residue of full-length alpha-SN. Such antibodies do not bind to deletion mutants of alpha synuclein in which residue 1 is missing. Some such antibodies do not bind to full-length alpha synuclein in which the N-terminal amino acid is joined to a heterologous polypeptide. Some antibodies of the invention specifically bind to an epitope within residues 1-69 or residues 1-20 of human alpha-synuclein. Some antibodies specifically bind to an epitope within residues 1-20 of human alpha-synuclein. Some antibodies specifically bind to an epitope with a segment of human alpha-synuclein selected from residues 1 to $N_a$ of SEQ ID NO.: 1, where $N_a$ is 5 to 20; residues 2 to $N_b$ of SEQ ID NO.: 1, where $N_b$ is 6 to 21; or residues 3-$N_c$ of SEQ ID NO.: 1 where $N_c$ is 7 to 22. Some antibodies bind to an epitope within a segment of human alpha synuclein selected from the group consisting of consisting of SN1-5, SN1-6, SN1-7, SN1-8, SN1-9, SN1-10, SN1-11, SN1-12, SN1-13, SN1-14 SN1-15, SN1-16, SN1-17, SN1-18, SN1-19, and SN1-20.

Some antibodies binds to an epitope at or near the C-terminus of alpha-SN (e.g., within amino acids 70-140, 100-140, 120-140, 130-140 or 135-140). Some antibodies bind to an epitope in which the C-terminal residue of the epitope is the C-terminal residue of (full-length) alpha-SN. Such antibodies do not bind to deletion mutants of alpha synuclein in which residue 140 is missing. Some such antibodies do not bind to full-length alpha synuclein in which the C-terminal amino acid is joined to a heterologous polypeptide. In some methods, the antibody specifically binds to NAC without binding to full length alpha-SN.

Some antibodies of the invention specifically bind to an epitope within residues 70-140 or 83-140 of human alpha synuclein. Some antibodies specifically bind to an epitope within residues 120-140 of human alpha-synuclein. Some antibodies specifically bind to an epitope with a segment of human alpha-synuclein selected from 83-101, 107-125, 110-128 and 124-140. Some antibodies bind to an epitope within a segment of human alpha synuclein selected from the group consisting of SN124-140, SN125-140, SN126-140, SN127-140, SN128-140, SN 129-140, SN130-140, SN131-140, SN132-140, SN133-140, SN134-140, SN135-140, SN136-140, SN137-140, SN124-139, SN125-139, SN126-139, SN127-139, SN128-139, SN124-139, SN125-139, SN126-139, SN127-139, SN128-139, SN 129-139, SN130-139, SN131-139, SN132-139, SN133-139, SN134-139, SN135-139, SN136-139, SN137-139, SN124-138, SN124-138, SN125-138, SN126-138, SN127-138, SN128-138, SN 129-138, SN130-138, SN131-138, SN132-138, SN133-138, SN134-138, SN135-138, SN136-138, SN124-137, SN125-137, SN126-137, SN127-137, SN128-137, SN 129-137, SN130-137, SN131-137, SN132-137, SN133-137, SN134-137, SN135-137, SN124-136, SN125-136, SN126-136, SN127-136, SN128-136, SN 129-136, SN130-136, SN131-136, SN132-136, SN133-136, and SN134-136.

Some antibodies bind to an epitope within a segment of human alpha-synuclein selected from amino acids 90-140, 98-140, 108-136, 110-130 or 118-126 of alpha synuclein.

Some antibodies bind to an epitope with a segment of human alpha-synuclein selected from SN 70-119, 80-109, 88-101, or 91-99 or 70-99.

Monoclonal antibodies binding to C-terminal region epitopes preferably bind with high affinity e.g., at least $10^8$, $10^9$ or $10^{10}$ $M^{-1}$ to human alpha synuclein.

Some antibodies of the invention specifically recognize alpha-SN phosphorylated at position 129 (serine) and do not specifically bind unphosphorylated alpha-SN. Some antibodies bind to an epitope within the segment SN 120-130 of human alpha-synuclein selected from, such as SN 124-134.

Monoclonal or polyclonal antibodies that specifically bind to a preferred segment of alpha-SN without specifically binding to other regions of alpha-SN have a number of advantages relative to monoclonal antibodies binding to other regions or polyclonal sera to intact alpha-SN. First, for equal mass dosages, dosages of antibodies that specifically bind to preferred segments contain a higher molar dosage of antibodies effective in clearing amyloid plaques. Second, antibodies specifically binding to preferred segments can induce a clearing response against LBs without inducing a clearing response against intact alpha-SN, thereby reducing the potential for side effects.

Optionally, antibodies can be screened for prophylactic or therapeutic activity in transgenic animals of LB disease as described above. Optionally, a collection of antibodies is prescreened for relative binding to denatured human alpha synuclein or a fragment thereof. The relative binding affinities can be estimated from relative intensities of signal in an immunoblot. An antibody having relative binding affinity above the mean, or preferably the antibody having the highest binding affinity tested is selected for further screening in transgenic animals. Similar prescreening can be performed to test antibodies for binding to aggregates of alpha-synuclein in tissue sections by immunocytochemistry. Tissue sections can be obtained from the brain of a diseased patient or a transgenic animal model.

In one embodiment the antibody designated 6H7, or an antibody that competes with 6H7 for specific binding to alpha synuclein is used for passive immunization. In one embodiment the antibody designated 8A5, or an antibody that competes with 8A5 for specific binding to alpha synuclein is used for passive immunization. In one embodiment the antibody designated 9E4, or an antibody that competes with 9E4 for specific binding to alpha synuclein is used for passive immunization. In one embodiment the antibody designated 1H7, or an antibody that competes with 1H7 for specific binding to alpha synuclein is used for passive immunization. In one embodiment the antibody designated 11A5, or an antibody that competes with 11A5 for specific binding to alpha synuclein is used for passive immunization. In some embodiments an aforementioned antibody is used in combination with each other or with other anti-alpha synuclein antibodies.

As described herein, administration of antibodies recognizing epitopes in the amino terminal and carboxy terminal regions of alpha-synuclein (i.e., 8A5 and 6H7) reduced alpha-synuclein aggregates in the brains of transgenic mice overexpressing human alpha-synuclein (see, e.g., Example IX). Based in part on this discovery, it is contemplated that administration in combination of antibodies that recognize a N-terminal epitope (e.g., as described above) and antibodies that recognize a C-terminal epitope (e.g., as described above) will be particularly effective in prophylaxis and therapy. Thus, in one aspect, the invention provides a method for prophylaxis or treatment of a disease characterized by Lewy bodies or alpha-synuclein aggregation in the brain by administering in combination to a patient having or at risk of the disease an effective regime of a first antibody that specifically binds to an epitope within residues 1-20 of human alpha-synuclein, residues being numbered according to SEQ ID NO:1 and administering a second antibody that that specifically binds to an epitope within residues 70-140 of human alpha-synuclein. Preferably the first antibody binds to an epitope of alpha-synuclein within the sequence of residues 1 to $N_a$ of SEQ ID NO.: 1, where $N_a$ is 5 to 20; within the sequence of residues 2 to $N_b$ of SEQ ID NO.: 1, where $N_b$ is 6 to 21; and/or within the sequence of residues 3 to $N_c$ of SEQ ID NO.: 1, and $N_c$ is 7 to 22. Preferably the second antibody specifically binds to an epitope within residues 120-140 of human alpha-synuclein. The first and second antibodies can be administered simultaneously (e.g., coformulated), the same day, the same month and/or as part of the same course of therapy.

The invention provides compositions for prophylaxis or treatment of a disease characterized by Lewy bodies or alpha-synuclein aggregation in the brain comprising one or more antibodies that binds at a terminal region of alpha-synuclein, e.g., having a specificity described above. Compositions include dosage forms and formulations containing two or more antibodies. Exemplary formulations (suitable for co-formulating antibodies) are known in the art and include those described below in Section VII ("Treatment Regimes").

The invention also provides kits for prophylaxis or treatment of a disease characterized by Lewy bodies or alpha-synuclein aggregation in the brain. The kits include two (or more) antibodies where a first antibody binds an epitope at the N-terminus of human alpha-synuclein and the second antibody binds an epitope at the C-terminus of human alpha-synuclein. The antibodies can be combined in a single preparation or kit for simultaneous use. Alternatively, the antibodies can occupy separate containers (e.g., vials, syringes, tubes, or the like) in a kit for simultaneous, sequential or separate use. These antibodies can optionally be administered in combination with other agents that are at least partly effective in treatment of Lewy Bidy disease. Kits can also include agents that increase passage of the antibodies of the invention across the blood-brain barrier, other adjuvants and materials for administration to the patient.

i. General Characteristics of Immunoglobulins

The basic antibody structural unit is known to comprise a tetramer of subunits. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology*, Paul, W., ed., 2nd ed. Raven Press, N.Y., 1989, Ch. 7 (incorporated by reference in its entirety for all purposes).

The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md., 1987 and 1991); Chothia & Lesk, *J. Mol. Biol.* 196:901-917 (1987); or Chothia et al., *Nature* 342:878-883 (1989).

ii. Production of Nonhuman Antibodies

Chimeric and humanized antibodies have the same or similar binding specificity and affinity as a mouse or other non-human antibody that provides the starting material for construction of a chimeric or humanized antibody. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). See, Gonzales et al., *Minimizing the immunogenicity of antibodies for clinical application, Tumour Biol.* 26(1):31-43 (2005). Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as IgG1 and IgG4. Human isotype IgG1 is preferred. In some methods, the isotype of the antibody is human IgG1. IgM antibodies can also be used in some methods. A typical chimeric antibody is thus a hybrid protein consisting of the V or antigen-binding domain from a mouse antibody and the C or effector domain from a human antibody.

Humanized antibodies have variable region framework residues substantially from a human antibody (termed an acceptor antibody) and complementarity determining regions substantially from a mouse-antibody, (referred to as the donor immunoglobulin). See, Queen et al., *Proc. Natl. Acad. Sci. USA* 86:10029-10033 (1989), WO 90/07861, U.S. Pat. Nos. 5,693,762, 5,693,761, 5,585,089, 5,530,101, and Winter, U.S. Pat. No. 5,225,539 (each of which is incorporated by reference in its entirety for all purposes). The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See Carter et al., WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid should usually be substituted by the equivalent framework amino acid from the mouse antibody when it is reasonably expected that the amino acid:

(1) noncovalently binds antigen directly,
(2) is adjacent to a CDR region,
(3) otherwise interacts with a CDR region (e.g. is within about 6 Å of a CDR region), or
(4) participates in the VL-VH interface.

Other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins. Other candidates for substitution are acceptor human framework amino acids that are unusual for a human immunoglobulin at that position. The variable region frameworks of humanized immunoglobulins usually show at least 85% sequence identity to a human variable region framework sequence or consensus of such sequences.

Some humanized antibodies comprise complementarity determining regions (CDRs) sequences derived from mouse monoclonal antibody mAb 6H7. The cell line designated JH17.6H7.1.54.28 producing the antibody 6H7 has the ATCC accession number PTA-6910 having been deposited under the provisions of the Budapest Treaty with the American Type Culture Collection (ATCC, P.O. Box 1549, Manassas, Va. 20108) on Aug. 4, 2005.

Some humanized antibodies comprise complementarity determining regions (CDRs) sequences derived from mouse monoclonal antibody mAb 8A5. The cell line designated JH4.8A5.25.7.36 producing the antibody 8A5 has the ATCC accession number PTA-6909 having been deposited on Aug. 4, 2005.

Some humanized antibodies comprise complementarity determining regions (CDRs) sequences derived from mouse monoclonal antibody mAb 9E4. The cell line designated JH17.9E4.3.37.1.14.2 producing the antibody 9E4 has the ATCC accession number PTA-8221 having been deposited under the provisions of the Budapest Treaty with the American Type Culture Collection (ATCC, P.O. Box 1549, Manassas, Va. 20108) on Feb. 26, 2007.

Some humanized antibodies comprise complementarity determining regions (CDRs) sequences derived from mouse monoclonal antibody mAb 11A5. The cell line designated JH22.11A5.6.29.70.54.16.14 producing the antibody 11A5 has the ATCC accession number PTA-8222 having been deposited under the provisions of the Budapest Treaty with the American Type Culture Collection (ATCC, P.O. Box 1549, Manassas, Va. 20108) on Feb. 26, 2007.

Some humanized antibodies comprise complementarity determining regions (CDRs) sequences derived from mouse monoclonal antibody mAb 1H7. The cell line designated JH17.1H7.4.24.34 producing the antibody 1H7 has the ATCC accession number PTA-8220 having been deposited under the provisions of the Budapest Treaty with the American Type Culture Collection (ATCC, P.O. Box 1549, Manassas, Va. 20108) on Feb. 26, 2007.

As noted above, a number of methods are known for producing chimeric and humanized antibodies using an antibody-expressing cell line (e.g., hybridoma). For example, the immunoglobulin variable regions of the mouse 8A5 and/or 6H7 and/or 9E4 antibodies can be cloned and sequenced using well known methods. Likewise, the immunoglobulin variable regions of the mouse 1H7 or 11A5 antibodies can be cloned and sequenced using well known methods. In one method, for illustration and not limitation, the heavy chain variable VH region is cloned by RT-PCR using mRNA prepared from hybridoma cells. Consensus primers are employed to VH region leader peptide encompassing the translation initiation codon as the 5' primer and a g2b constant regions specific 3' primer. Exemplary primers are described in U.S. patent publication US 2005/0009150 by Schenk et al. (hereinafter, "Schenk"). The sequences from multiple, independently-derived clones, can be compared to ensure no changes are introduced during amplification. The sequence of the VH region can also be determined or confirmed by sequencing a VH fragment obtained by 5' RACE RT-PCR methodology and the 3' g2b specific primer.

The light chain variable VL region of 8A5, 6H7, 9E4, 1H7 or 11A5 can be cloned in an analogous manner as the VH region. In one approach, a consensus primer set designed for amplification of murine VL regions is designed to hybridize to the VL region encompassing the translation initiation codon, and a 3' primer specific for the murine Ck region downstream of the V-J joining region. In a second approach, 5'RACE RT-PCR methodology is employed to clone a VL encoding cDNA. Exemplary primers are described in Schenk. The cloned sequences are then combined with sequences encoding human constant regions.

In one approach, the heavy and light chain variable regions are re-engineered to encode splice donor sequences downstream of the respective VDJ or VJ junctions, and cloned into the mammalian expression vector, such as pCMV-hγ1 for the heavy chain, and pCMV-hκ1 for the light chain. These vectors encode human γ1 and Ck constant regions as exonic fragments downstream of the inserted variable region cassette. Following sequence verification, the heavy chain and light chain expression vectors can be co-transfected into COS cells to produce chimeric antibodies. Conditioned media is collected 48 hrs post transfection and assayed by western blot analysis for antibody production or ELISA for antigen binding. The chimeric antibodies are humanized as described above.

iii. Human Antibodies

Human antibodies against alpha-SN are provided by a variety of techniques described below. Some human antibodies are selected by competitive binding experiments, or otherwise, to have the same epitope specificity as a particular mouse antibody, such as one of the mouse monoclonal antibodies described in Examples IX and X. Human antibodies can also be screened for a particular epitope specificity by using only a fragment of alpha-SN as the immunogen, and/or by screening antibodies against a collection of deletion mutants of alpha-SN. Human antibodies preferably have isotype specificity human IgG1.

(1) Trioma Methodology

The basic approach and an exemplary cell fusion partner, SPAZ-4, for use in this approach have been described by Oestberg et al., *Hybridoma* 2:361-367 (1983); Oestberg, U.S. Pat. No. 4,634,664; and Engleman et al., U.S. Pat. No. 4,634,666 (each of which is incorporated by reference in its entirety for all purposes). The antibody-producing cell lines obtained by this method are called triomas, because they are descended from three cells-two human and one mouse. Initially, a mouse myeloma line is fused with a human B-lymphocyte to obtain a non-antibody-producing xenogeneic hybrid cell, such as the SPAZ-4 cell line described by Oestberg, supra. The xenogeneic cell is then fused with an immunized human B-lymphocyte to obtain an antibody-producing trioma cell line. Triomas have been found to produce antibody more stably than ordinary hybridomas made from human cells.

The immunized B-lymphocytes are obtained from the blood, spleen, lymph nodes or bone marrow of a human donor. If antibodies against a specific antigen or epitope are desired, it is preferable to use that antigen or epitope thereof for immunization. Immunization can be either in vivo or in vitro. For in vivo immunization, B cells are typically isolated from a human immunized with alpha-SN, a fragment thereof, larger polypeptide containing alpha-SN or fragment, or an anti-idiotypic antibody to an antibody to alpha-SN. In some methods, B cells are isolated from the same patient who is ultimately to be administered antibody therapy. For in vitro immunization, B-lymphocytes are typically exposed to antigen for a period of 7-14 days in a media such as RPMI-1640 (see Engleman, supra) supplemented with 10% human plasma.

The immunized B-lymphocytes are fused to a xenogeneic hybrid cell such as SPAZ-4 by well known methods. For example, the cells are treated with 40-50% polyethylene glycol of MW 1000-4000, at about 37 degrees C., for about 5-10 min. Cells are separated from the fusion mixture and propagated in media selective for the desired hybrids (e.g., HAT or AH). Clones secreting antibodies having the required binding specificity are identified by assaying the trioma culture medium for the ability to bind to alpha-SN or a fragment thereof. Triomas producing human antibodies having the desired specificity are subcloned by the limiting dilution technique and grown in vitro in culture medium. The trioma cell lines obtained are then tested for the ability to bind alpha-SN or a fragment thereof.

Although triomas are genetically stable they do not produce antibodies at very high levels. Expression levels can be increased by cloning antibody genes from the trioma into one or more expression vectors, and transforming the vector into standard mammalian, bacterial or yeast cell lines.

(2) Transgenic Non-Human Mammals

Human antibodies against alpha-SN can also be produced from non-human transgenic mammals having transgenes encoding at least a segment of the human immunoglobulin locus. Usually, the endogenous immunoglobulin locus of such transgenic mammals is functionally inactivated. Preferably, the segment of the human immunoglobulin locus includes unrearranged sequences of heavy and light chain components. Both inactivation of endogenous immunoglobulin genes and introduction of exogenous immunoglobulin genes can be achieved by targeted homologous recombination, or by introduction of YAC chromosomes. The transgenic mammals resulting from this process are capable of functionally rearranging the immunoglobulin component sequences, and expressing a repertoire of antibodies of various isotypes encoded by human immunoglobulin genes, without expressing endogenous immunoglobulin genes. The production and properties of mammals having these properties are described in detail by, e.g., Lonberg et al., WO93/1222, U.S. Pat. Nos. 5,877,397, 5,874,299, 5,814,318, 5,789,650, 5,770,429, 5,661,016, 5,633,425, 5,625,126, 5,569,825, 5,545,806, Nature 148, 1547-1553 (1994), Nature Biotechnology 14, 826 (1996), Kucherlapati, WO 91/10741 (each of which is incorporated by reference in its entirety for all purposes). Transgenic mice are particularly suitable. Anti-alpha-SN antibodies are obtained by immunizing a transgenic nonhuman mammal, such as described by Lonberg or Kucherlapati, supra, with alpha-SN or a fragment thereof. Monoclonal antibodies are prepared by, e.g., fusing B-cells from such mammals to suitable myeloma cell lines using conventional Kohler-Milstein technology. Human polyclonal antibodies can also be provided in the form of serum from humans immunized with an immunogenic agent. Optionally, such polyclonal antibodies can be concentrated by affinity purification using alpha-SN or other amyloid peptide as an affinity reagent.

(3) Phage Display Methods

A further approach for obtaining human anti-alpha-SN antibodies is to screen a DNA library from human B cells according to the general protocol outlined by Huse et al., Science 246:1275-1281 (1989). As described for trioma methodology, such B cells can be obtained from a human immunized with alpha-SN, fragments, longer polypeptides containing alpha-SN or fragments or anti-idiotypic antibodies. Optionally, such B cells are obtained from a patient who is ultimately to receive antibody treatment. Antibodies binding to alpha-SN or a fragment thereof are selected. Sequences encoding such antibodies (or binding fragments) are then cloned and amplified. The protocol described by Huse is rendered more efficient in combination with phage-display technology. See, e.g., Dower et al., WO 91/17271 and McCafferty et al., WO 92/01047, U.S. Pat. Nos. 5,877,218, 5,871,907, 5,858,657, 5,837,242, 5,733,743 and 5,565,332 (each of which is incorporated by reference in its entirety for all purposes). In these methods, libraries of phage are produced in which members display different antibodies on their outer surfaces. Antibodies are usually displayed as Fv or Fab fragments. Phage displaying antibodies with a desired specificity are selected by affinity enrichment to an alpha-SN peptide or fragment thereof.

In a variation of the phage-display method, human antibodies having the binding specificity of a selected murine antibody can be produced. See Winter, WO 92/20791. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions are obtained from a library of rearranged human heavy chain variable regions. A phage showing strong specific binding for alpha-SN (e.g., at least $10^8$ and preferably at least $10^9$ $M^{-1}$) is selected. The human heavy chain variable region from this phage then serves as a starting material for constructing a further phage library. In this library, each phage displays the same heavy chain variable region (i.e., the region identified from the first display library) and a different light chain variable region. The light chain variable regions are obtained from a library of rearranged human variable light chain regions. Again, phage showing strong specific binding for alpha-SN are selected. These phage display the variable regions of completely human anti-alpha-SN antibodies. These antibodies usually have the same or similar epitope specificity as the murine starting material.

iv. Selection of Constant Region

The heavy and light chain variable regions of chimeric, humanized, or human antibodies can be linked to at least a portion of a human constant region. The choice of constant region depends, in part, whether antibody-dependent complement and/or cellular mediated toxicity is desired. For example, isotopes IgG1 and IgG3 have complement activity and isotypes IgG2 and IgG4 do not. Choice of isotype can also affect passage of antibody into the brain. Human isotype IgG1 is preferred. Light chain constant regions can be lambda or kappa. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

v. Expression of Recombinant Antibodies

Chimeric, humanized and human antibodies are typically produced by recombinant expression. Recombinant polynucleotide constructs typically include an expression control sequence operably linked to the coding sequences of antibody chains, including naturally associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences.

*E. coli* is one prokaryotic host particularly useful for cloning the DNA sequences of the present invention. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells are a preferred host for expressing nucleotide segments encoding immunoglobulins or fragments thereof. See Winnacker, *From Genes to Clones*, (VCH Publishers, NY, 1987). A number of suitable host cell lines capable of secreting intact heterologous proteins have been developed in the art, and include CHO cell lines, various COS cell lines, HeLa cells, L cells, human embryonic kidney cell, and myeloma cell lines. Preferably, the cells are nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., *J. Immunol.* 148:1149 (1992).

Alternatively, antibody coding sequences can be incorporated in transgenes for introduction into the genome of a transgenic animal and subsequent expression in the milk of the transgenic animal (see, e.g., U.S. Pat. Nos. 5,741,957, 5,304,489, 5,849,992). Suitable transgenes include coding sequences for light and/or heavy chains in operable linkage with a promoter and enhancer from a mammary gland specific gene, such as casein or beta lactoglobulin.

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

Once expressed, antibodies can be purified according to standard procedures of the art, including HPLC purification, column chromatography, gel electrophoresis and the like (see generally, Scopes, *Protein Purification* (Springer-Verlag, NY, 1982)).

3. Conjugates

Some agents for inducing an immune response contain the appropriate epitope for inducing an immune response against LBs but are too small to be immunogenic. In this situation, a peptide immunogen can be linked to a suitable carrier molecule to form a conjugate which helps elicit an immune response. Suitable carriers include serum albumins, keyhole limpet hemocyanin, immunoglobulin molecules, thyroglobulin, ovalbumin, tetanus toxoid, or a toxoid from other pathogenic bacteria, such as diphtheria, *E. coli*, cholera, or *H. pylori*, or an attenuated toxin derivative. T cell epitopes are also suitable carrier molecules. Some conjugates can be formed by linking agents of the invention to an immunostimulatory polymer molecule (e.g., tripalmitoyl-5-glycerine cysteine ($Pam_3Cys$), mannan (a manose polymer), or glucan (a beta 1→2 polymer)), cytokines (e.g., IL-1, IL-1 alpha and beta peptides, IL-2, gamma-INF, IL-10, GM-CSF), and chemokines (e.g., MIP1 alpha and beta, and RANTES). Immunogenic agents can also be linked to peptides that enhance transport across tissues, as described in O'Mahony, WO 97/17613 and WO 97/17614. Immunogens may be linked to the carries with or without spacers amino acids (e.g., gly-gly).

Some conjugates can be formed by linking agents of the invention to at least one T cell epitope. Some T cell epitopes are promiscuous while other T cell epitopes are universal. Promiscuous T cell epitopes are capable of enhancing the induction of T cell immunity in a wide variety of subjects displaying various HLA types. In contrast to promiscuous T cell epitopes, universal T cell epitopes are capable of enhancing the induction of T cell immunity in a large percentage, e.g., at least 75%, of subjects displaying various HLA molecules encoded by different HLA-DR alleles.

A large number of naturally occurring T-cell epitopes exist, such as, tetanus toxoid (e.g., the P2 and P30 epitopes), Hepatitis B surface antigen, pertussis, toxoid, measles virus F protein, *Chlamydia trachomitis* major outer membrane protein, diphtheria toxoid, *Plasmodium falciparum* circumsporozite T, *Plasmodium falciparum* CS antigen, *Schistosoma mansoni* triose phosphate isomersae, *Escherichia coli* TraT, and Influenza virus hemagluttinin (HA). The immunogenic peptides of the invention can also be conjugated to the T-cell epitopes described in Sinigaglia F. et al., *Nature*, 336: 778-780 (1988); Chicz R. M. et al., *J. Exp. Med.*, 178:27-47 (1993); Hammer J. et al., *Cell* 74:197-203 (1993); Falk K. et al., *Immunogenetics*, 39:230-242 (1994); WO 98/23635; and, Southwood S. et al. *J. Immunology*, 160:3363-3373 (1998) (each of which is incorporated herein by reference for all purposes). Further examples include:

```
Influenza Hemagluttinin:
HA307-319 PKYVKQNTLKLAT            (SEQ ID NO: 4)

Malaria CS:
T3 epitope EKKIAKMEKASSVFNV        (SEQ ID NO: 5)

Hepatitis B surface antigen:
HBsAg19-28 FFLLTRILTI               (SEQ ID NO: 6)

Heat Shock Protein 65:
hsp65153-171 DQSIGDLIAEAMDKVGNEG    (SEQ ID NO: 7)

bacille Calmette-Guerin
QVHFQPLPPAVVKL                     (SEQ ID NO: 8)

Tetanus toxoid:
TT830-844 QYIKANSKFIGITEL           (SEQ ID NO: 9)

Tetanus toxoid:
TT947-967 FNNFTVSFWLRVPKVSASHLE     (SEQ ID NO: 10)

HIV gp120 T1:
KQIINMWQEVGKAMYA                   (SEQ ID NO: 11)
```

Alternatively, the conjugates can be formed by linking agents of the invention to at least one artificial T-cell epitope capable of binding a large proportion of MHC Class II molecules, such as the pan DR epitope ("PADRE"). PADRE is described in U.S. Pat. No. 5,736,142, WO 95/07707, and Alexander J et al., *Immunity*, 1:751-761 (1994) (each of which is incorporated herein by reference for all purposes). A preferred PADRE peptide is AKXVAAWTLKAAA (SEQ ID NO: 12), (common residues bolded) wherein X is preferably cyclohexylalanine, tyrosine or phenylalanine, with cyclohexylalanine being most preferred.

Immunogenic agents can be linked to carriers by chemical crosslinking. Techniques for linking an immunogen to a carrier include the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the epsilon-amino on a lysine, or other free amino group in other amino acids. A variety of such disulfide/amide-forming agents are described by *Immun. Rev.* 62, 185 (1982). Other bifunctional coupling agents form a thioether rather than a disulfide linkage. Many of these thio-ether-forming agents are commercially available and include reactive esters of 6-maleimidocaproic acid, 2-bromoacetic acid, and 2-iodoacetic acid, 4-(N-maleimido-methyl)cyclohexane-1-carboxylic acid. The carboxyl groups can be activated by combining them with succinimide or 1-hydroxyl-2-nitro-4-sulfonic acid, sodium salt.

Immunogenicity can be improved through the addition of spacer residues (e.g., Gly-Gly) between the $T_h$ epitope and the peptide immunogen of the invention. In addition to physically separating the $T_h$ epitope from the B cell epitope (i.e., the peptide immunogen), the glycine residues can disrupt any artificial secondary structures created by the joining of the $T_h$ epitope with the peptide immunogen, and thereby eliminate interference between the T and/or B cell responses. The conformational separation between the helper epitope and the antibody eliciting domain thus permits more efficient interactions between the presented immunogen and the appropriate $T_h$ and B cells.

To enhance the induction of T cell immunity in a large percentage of subjects displaying various HLA types to an agent of the present invention, a mixture of conjugates with different $T_h$ cell epitopes can be prepared. The mixture may contain a mixture of at least two conjugates with different $T_h$ cell epitopes, a mixture of at least three conjugates with different $T_h$ cell epitopes, or a mixture of at least four conjugates with different $T_h$ cell epitopes. The mixture may be administered with an adjuvant.

Immunogenic peptides can also be expressed as fusion proteins with carriers (i.e., heterologous peptides). The immunogenic peptide can be linked at its amino terminus, its carboxyl terminus, or both to a carrier. Optionally, multiple repeats of the immunogenic peptide can be present in the fusion protein. Optionally, an immunogenic peptide can be linked to multiple copies of a heterologous peptide, for example, at both the N and C termini of the peptide. Some carrier peptides serve to induce a helper T-cell response against the carrier peptide. The induced helper T-cells in turn induce a B-cell response against the immunogenic peptide linked to the carrier peptide.

Some agents of the invention comprise a fusion protein in which an N-terminal fragment of alpha-SN is linked at its C-terminus to a carrier peptide. In such agents, the N-terminal residue of the fragment of alpha-SN constitutes the N-terminal residue of the fusion protein. Accordingly, such fusion proteins are effective in inducing antibodies that bind to an epitope that requires the N-terminal residue of alpha-SN to be in free form. Some agents of the invention comprise a plurality of repeats of NAC linked at the C-terminus to one or more copy of a carrier peptide. Some fusion proteins comprise different segments of alpha-SN in tandem.

Some agents of the invention comprise a fusion protein in which a C-terminal fragment of alpha-SN is linked at its N-terminus to a carrier peptide. In such agents, the C-terminal residue of the fragment of alpha-SN constitutes the C-terminal residue of the fusion protein. Accordingly, such fusion proteins are effective in inducing antibodies that bind to an epitope that requires the C-terminal residue of alpha-SN to be in free form. Some agents of the invention comprise a plurality of repeats of a C-terminal peptide, such as SN125-140 linked at the N-terminus to one or more copy of a carrier peptide. Some fusion proteins comprise different segments of alpha-SN in tandem.

In some fusion proteins, NAC is fused at its N-terminal end to a heterologous carrier peptide. In some fusion proteins, NAC is fused at its C-terminal end to a heterologous carrier peptide. Some fusion proteins comprise a heterologous peptide linked to the N-terminus or C-terminus of NAC, which is in turn linked to one or more additional NAC segments of alpha-SN in tandem. Some fusion proteins comprise multiple copies of a C-terminal alpha synuclein peptide, as described above, and multiple copies of a heterologous peptide interlinked to one another.

In some fusion proteins, a fragment of alpha-SN not including either the C-terminus or N-terminus (e.g., SN110-130, SN 85-105) is fused at its N-terminal end to a heterologous carrier peptide. In some fusion proteins, the fragment is fused at its C-terminal end to a heterologous carrier peptide. Some fusion proteins comprise a heterologous peptide linked to the N-terminus or C-terminus of the fragment, which is in turn linked to one or more additional fragments of alpha-SN in tandem. Some fusion proteins comprise multiple copies of a alpha synuclein peptide, as described above, and multiple copies of a heterologous peptide interlinked to one another.

Some examples of fusion proteins suitable for use in the invention are shown below. Some of these fusion proteins comprise segments of alpha-SN (including any of the fragments described above) linked to tetanus toxoid epitopes such as described in U.S. Pat. No. 5,196,512, EP 378,881 and EP 427,347. Some fusion proteins comprise segments of alpha-SN linked to at least one PADRE. Some heterologous peptides are promiscuous T-cell epitopes, while other heterologous peptides are universal T-cell epitopes. In some methods, the agent for administration is simply a single fusion protein with an alpha-SN segment linked to a heterologous segment in linear configuration. The therapeutic agents of the invention may be represented using a formula. For example, in some methods, the agent is multimer of fusion proteins represented by the formula $2^x$, in which x is an integer from 1-5. Preferably x is 1, 2, or 3, with 2 being most preferred. When x is two, such a multimer has four fusion proteins linked in a preferred configuration referred to as MAP4 (see U.S. Pat. No. 5,229,490).

The MAP4 configuration is shown below, where branched structures are produced by initiating peptide synthesis at both the N terminal and side chain amines of lysine. Depending upon the number of times lysine is incorporated into the sequence and allowed to branch, the resulting structure will present multiple N termini. In this example, four identical N termini have been produced on the branched lysine-containing core. Such multiplicity greatly enhances the responsiveness of cognate B cells.

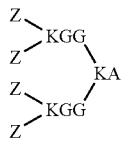

Z refers to the NAC peptide, a fragment of the NAC peptide, or other active fragment of alpha-SN as described in section I. 2 above. Z may represent more than one active fragment, for example:

```
                                              (SEQ ID NO: 13)
Z = alpha-SN 60-72 (NAC region) peptide = NH2-

KEQVTNVCGGAVVT-COOH (SEQ ID NO: 14)
Z = alpha-SN 73-84 (NAC region) peptide = NH2-

GVTAVAQKTVECG-COOH (SEQ ID NO: 15)
Z = alpha-SN 102-112 peptide = NH2-C-aminoheptanoic acid-KNEEGAPCQEG-COOH
``` alpha-SN 128-140 peptide
Other examples of fusion proteins include:
Z-Tetanus toxoid 830-844 in a MAP4 configuration:

```
    Z-QYIKANSKFIGITEL            (SEQ ID NO: 16)
```

Z-Tetanus toxoid 947-967 in a MAP4 configuration:

```
    Z-FNNFTVSFWLRVPKVSASHLE      (SEQ ID NO: 17)
```

Z-Tetanus toxoid$_{830-844}$ in a MAP4 configuration:

```
    Z-QYIKANSKFIGITEL            (SEQ ID NO: 18)
```

Z-Tetanus toxoid$_{830-844}$+Tetanus toxoid$_{947-967}$ in a linear configuration:

```
                                              (SEQ ID NO: 19)
Z-QYIKANSKFIGITELFNNFTVSFWLRVPKVSASHLE
```

PADRE peptide (all in linear configurations), wherein X is preferably cyclohexylalanine, tyrosine or phenylalanine, with cyclohexylalanine being most preferred-Z:

```
    AKXVAAWTLKAAA-Z              (SEQ ID NO: 20)
```

3Z-PADRE peptide:

```
    Z-Z-Z-AKXVAAWTLKAAA          (SEQ ID NO: 21)
```

Further examples of fusion proteins include:

```
                                              (SEQ ID NO: 22)
AKXVAAWTLKAAA-Z-Z-Z-Z
```

```
                                              (SEQ ID NO: 23)
Z-AKXVAAWTLKAAA (SEQ ID NO: 24)
Z-ISQAVHAAHAEINEAGR (SEQ ID NO: 25)
PKYVKQNTLKLAT-Z-Z-Z (SEQ ID NO: 26)
Z-PKYVKQNTLKLAT-Z (SEQ ID NO: 27)
Z-Z-Z-PKYVKQNTLKLAT (SEQ ID NO: 28)
Z-Z-PKYVKQNTLKLAT (SEQ ID NO: 29)
Z-PKYVKQNTLKLAT-EKKIAKMEKASSVFNV-QYIKANSKFIGITEL-
FNNFTVSFWLRVPKVSASHLE-Z-Z-Z-Z-QYIKANSKFIGITEL-
FNNFTVSFWLRVPKVSASHLE (SEQ ID NO: 30)
Z-QYIKANSKFIGITELCFNNFTVSFWLRVPKVSASHLE-Z-
QYIKANSKFIGITELCFNNFTVSFWLRVPKVSASHLE-Z (SEQ ID NO: 31)
Z-QYIKANSKFIGITEL
``` on a 2 branched resin:

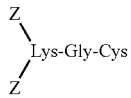

```
    EQVTNVGGAISQAVHAAHAEINEAGR    (SEQ ID NO: 32)
```

(Synuclein Fragment Fusion Protein in Map-4 Configuration)

The same or similar carrier proteins and methods of linkage can be used for generating immunogens to be used in generation of antibodies against alpha-SN for use in passive immunization. For example, alpha-SN or a fragment linked to a carrier can be administered to a laboratory animal in the production of monoclonal antibodies to alpha-SN.

4. Nucleic Acid Encoding Therapeutic Agents

Immune responses against Lewy bodies can also be induced by administration of nucleic acids encoding segments of alpha-SN peptide, and fragments thereof, other peptide immunogens, or antibodies and their component chains used for passive immunization. Such nucleic acids can be DNA or RNA. A nucleic acid segment encoding an immunogen is typically linked to regulatory elements, such as a promoter and enhancer that allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector. For administration of double-chain antibodies, the two chains can be cloned in the same or separate vectors. The nucleic acid encoding therapeutic agents of the invention may also encode at least one T cell epitope. The disclosures herein which relates to the use of adjuvants and the use of apply mutatis mutandis to their use with the nucleic acid encoding therapeutic agents of the present invention.

A number of viral vector systems are available including retroviral systems (see, e.g., Lawrie and Tumin, *Cur. Opin. Genet. Develop.* 3, 102-109 (1993)); adenoviral vectors (see, e.g., Bett et al., *J. Virol.* 67, 5911 (1993)); adeno-associated virus vectors (see, e.g., Zhou et al., *J. Exp. Med.* 179, 1867 (1994)), viral vectors from the pox family including vaccinia virus and the avian pox viruses, viral vectors from the alpha virus genus such as those derived from Sindbis and Semliki Forest Viruses (see, e.g., Dubensky et al., *J. Virol.* 70, 508-519 (1996)), Venezuelan equine encephalitis virus (see U.S. Pat. No. 5,643,576) and rhabdoviruses, such as vesicular stomatitis virus (see WO 96/34625) and papillomaviruses (Ohe et al., *Human Gene Therapy* 6, 325-333 (1995); Woo et al., WO 94/12629 and Xiao & Brandsma, *Nucleic Acids. Res.* 24, 2630-2622 (1996)).

DNA encoding an immunogen, or a vector containing the same, can be packaged into liposomes. Suitable lipids and related analogs are described by U.S. Pat. Nos. 5,208,036, 5,264,618, 5,279,833, and 5,283,185. Vectors and DNA encoding an immunogen can also be adsorbed to or associated with particulate carriers, examples of which include polymethyl methacrylate polymers and polylactides and poly (lactide-co-glycolides), (see, e.g., McGee et al., *J. Micro Encap.* 1996).

Gene therapy vectors or naked DNA can be delivered in vivo by administration to an individual patient, typically by systemic administration (e.g., intravenous, intraperitoneal, nasal, gastric, intradermal, intramuscular, subdermal, or intracranial infusion) or topical application (see e.g., U.S. Pat. No. 5,399,346). Such vectors can further include facilitating agents such as bupivacine (see e.g., U.S. Pat. No. 5,593,970). DNA can also be administered using a gene gun. See Xiao & Brandsma, supra. The DNA encoding an immunogen is precipitated onto the surface of microscopic metal beads. The microprojectiles are accelerated with a shock wave or expanding helium gas, and penetrate tissues to a depth of several cell layers. For example, The Accel™ Gene Delivery Device manufactured by Agacetus, Inc. Middleton, Wis. is suitable. Alternatively, naked DNA can pass through skin into the blood stream simply by spotting the DNA onto skin with chemical or mechanical irritation (see WO 95/05853).

In a further variation, vectors encoding immunogens can be delivered to cells ex vivo, such as cells explanted from an individual patient (e.g., lymphocytes, bone marrow aspirates, and tissue biopsy) or universal donor hematopoietic stem cells, followed by reimplantation of the cells into a patient, usually after selection for cells which have incorporated the vector.

III. Agents for Inducing Immunogenic Response Against Aβ

Aβ, also known as β-amyloid peptide, or A4 peptide (see U.S. Pat. No. 4,666,829; Glenner & Wong, Biochem. Biophys. Res. Commun. 120, 1131 (1984)), is a peptide of 39-43 amino acids, which is the principal component of characteristic plaques of Alzheimer's disease. Aβ is generated by processing of a larger protein APP by two enzymes, termed β and γ secretases (see Hardy, TINS 20, 154 (1997)). Known mutations in APP associated with Alzheimer's disease occur proximate to the site of β or γ secretase, or within Aβ. For example, position 717 is proximate to the site of γ-secretase cleavage of APP in its processing to Aβ, and positions 670/671 are proximate to the site of β-secretase cleavage. It is believed that the mutations cause AD by interacting with the cleavage reactions by which Aβ is formed so as to increase the amount of the 42/43 amino acid form of Aβ generated.

Aβ has the unusual property that it can fix and activate both classical and alternate complement cascades. In particular, it binds to C1q and ultimately to C3bi. This association facilitates binding to macrophages leading to activation of B cells. In addition, C3bi breaks down further and then binds to CR2 on B cells in a T cell dependent manner leading to a 10,000 increase in activation of these cells. This mechanism causes Aβ to generate an immune response in excess of that of other antigens.

Aβ has several natural occurring forms. The human forms of Aβ are referred to as Aβ39, Aβ40, Aβ41, Aβ42 and Aβ43. The sequences of these peptides and their relationship to the APP precursor are illustrated by FIG. 1 of Hardy et al., TINS 20, 155-158 (1997). For example, Aβ42 has the sequence:

(SEQ ID NO: 33)
DAEFRHDSGYEVHHQKLVFFAEDVGSNKGAIIGLMVGGVVIAT

Aβ41, Aβ40 and Aβ39 differ from Aβ42 by the omission of Ala, Ala-Ile, and Ala-Ile-Val respectively from the C-terminal end. Aβ43 differs from Aβ42 by the presence of a Thr residue at the C-terminus.

Analogous agents to those described above for alpha-SN have previously been described for Aβ (see WO 98/25386 and WO 00/72880, both of which are incorporated herein for all purposes). These agents include Aβ and active fragments thereof, conjugates of Aβ, and conjugates of Aβ active fragments, antibodies to Aβ and active fragments thereof (e.g., mouse, humanized, human, and chimeric antibodies), and nucleic acids encoding antibody chains. Active fragments from the N-terminal half of Aβ are preferred. Preferred immunogenic fragments include Aβ1-5, 1-6, 1-7, 1-10, 3-7, 1-3, and 1-4. The designation Aβ1-5 for example, indicates a fragment including residues 1-5 of Aβ and lacking other residues of Aβ. Fragments beginning at residues 1-3 of Aβ and ending at residues 7-11 of Aβ are particularly preferred.

The disclosures herein which relates to agents inducing an active immune response, agents for inducing a passive immune response, conjugates, and nucleic acids encoding therapeutic agents (see Sections II. 1, 2, 3, and 4, above) apply mutatis mutandis to the use of Aβ and fragments thereof. The disclosures herein which relate to agents inducing an active immune response, agents for inducing a passive immune response, conjugates, and nucleic acids encoding therapeutic agents (see Sections II. 1, 2, 3, and 4, above) apply mutatis mutandis to the use of Aβ and fragments thereof. The disclosures herein which relate to patients amendable to treatment, and treatment regimes (see Sections IV and V, below) apply mutatis mutandis to the use of Aγ and fragments thereof.

Disaggregated Aβ or fragments thereof means monomeric peptide units. Disaggregated Aβ or fragments thereof are generally soluble, and are capable of self-aggregating to form soluble oligomers. Oligomers of Aβ and fragments thereof are usually soluble and exist predominantly as alpha-helices or random coils. Aggregated Aβ or fragments thereof, means oligomers of alpha-SN or fragments thereof that have associate into insoluble beta-sheet assemblies. Aggregated Aβ or fragments thereof, means also means fibrillar polymers. Fibrils are usually insoluble. Some antibodies bind either soluble Aβ or fragments thereof or aggregated Aβ or fragments thereof. Some antibodies bind both soluble Aβ or fragments thereof and aggregated Aβ or fragments thereof.

Some examples of conjugates include:

AN90549 (Aβ1-7-Tetanus toxoid 830-844 in a MAP4 configuration):

DAEFRHD-QYIKANSKFIGITEL (SEQ ID NO: 34)

AN90550 (Aβ1-7-Tetanus toxoid 947-967 in a MAP4 configuration):

DAEFRHD-FNNFTVSFWLRVPKVSASHLE (SEQ ID NO: 35)

AN90542 (Aβ1-7-Tetanus toxoid 830-844+947-967 in a linear configuration):

(SEQ ID NO: 36)
DAEFRHD-QYIKANSKFIGITELFNNFTVSFWLRVPKVSASHLE

AN90576: (Aβ3-9)-Tetanus toxoid 830-844 in a MAP4 configuration):

EFRHDSG-QYIKANSKFIGITEL (SEQ ID NO: 37)

PADRE peptide (all in linear configurations), wherein X is preferably cyclohexylalanine, tyrosine or phenylalanine, with cyclohexylalanine being most preferred:

AN90562 (PADRE-Aβ1-7):

AKXVAAWTLAAA-DAEFRHD (SEQ ID NO: 38)

AN90543 (3 PADRE-Aβ1-7):

(SEQ ID NO: 39)
DAEFRHD-DAEFRHD-DAEFRHD-AKXVAAWTLKAAA

Other examples of fusion proteins (immunogenic epitope of Aβ bolded) include:

(SEQ ID NO: 40)
AKXVAAWTLKAAA-DAEFRHD-DAEFRHD-DAEFRHD

(SEQ ID NO: 41)
DAEFRHD-AKXVAAWTLKAAA (SEQ ID NO: 42)
DAEFRHD-ISQAVHAAHAEINEAGR (SEQ ID NO: 43)
FRHDSGY-ISQAVHAAHAEINEAGR (SEQ ID NO: 44)
EFRHDSG-ISQAVHAAHAEINEAGR (SEQ ID NO: 45)
PKYVKQNTLKLAT-DAEFRHD-DAEFRHD-DAEFRHD

(SEQ ID NO: 46)
DAEFRHD-PKYVKQNTLKLAT-DAEFRHD

(SEQ ID NO: 47)
DAEFRHD-DAEFRHD-DAEFRHD-PKYVKQNTLKLAT (SEQ ID NO: 48)
DAEFRHD-DAEFRHD-PKYVKQNTLKLAT (SEQ ID NO: 49)
DAEFRHD-PKYVKQNTLKLAT-EKKIAKMEKASSVFNVQYIKANSKFIGITEL-FNNFTVSFWLRVPKVSASHLE-DAEFRHD

(SEQ ID NO: 50)
DAEFRHD-DAEFRHD-DAEFRHD-QYIKANSKFIGITELNNFTVSFWLRVPKVSASHLE (SEQ ID NO: 51)
DAEFRHD-QYIKANSKFIGITELCFNNFTVSFWLRVPKVSASHLE (SEQ ID NO: 52)
DAEFRHD-QYIKANSKFIGITELCFNNFTVSFWLRVPKVSASHLE-DAEFRHD

(SEQ ID NO: 53)
DAEFRHD-QYIKANSKFIGITEL on a 2 branched resin.

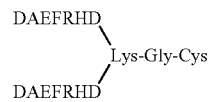

Preferred monoclonal antibodies bind to an epitope within residues 1-10 of Aβ (with the first N terminal residue of natural Aβ designated 1). Some preferred monoclonal antibodies bind to an epitope within amino acids 1-5, and some to an epitope within 5-10. Some preferred antibodies bind to epitopes within amino acids 1-3, 1-4, 1-5, 1-6, 1-7 or 3-7. Some preferred antibodies bind to an epitope starting at resides 1-3 and ending at residues 7-11 of Aβ. Other antibodies include those binding to epitopes with residues 13-280 (e.g., monoclonal antibody 266). Preferred antibodies have human IgG1 isotype.

IV. Screening Antibodies for Clearing Activity

The invention provides methods of screening an antibody for activity in clearing a Lewy body or any other antigen, or associated biological entity, for which clearing activity is desired. To screen for activity against a Lewy body, a tissue sample from a brain of a patient with PD or an animal model having characteristic Parkinson's pathology is contacted with phagocytic cells bearing an Fc receptor, such as microglial cells, and the antibody under test in a medium in vitro. The phagocytic cells can be a primary culture or a cell line, such as BV-2, C8-B4, or THP-1. In some methods, the components are combined on a microscope slide to facilitate microscopic monitoring. In some methods, multiple reactions are performed in parallel in the wells of a microtiter dish. In such a format, a separate miniature microscope slide can be mounted in the separate wells, or a nonmicroscopic detection format, such as ELISA detection of alpha-SN can be used. Preferably, a series of measurements is made of the amount of Lewy body in the in vitro reaction mixture, starting from a baseline value before the reaction has proceeded, and one or more test values during the reaction. The antigen can be detected by staining, for example, with a fluorescently labeled antibody to alpha-SN or other components of LBs. The antibody used for staining may or may not be the same as the antibody being tested for clearing activity. A reduction relative to baseline during the reaction of the LBs indicates that the antibody under test has clearing activity. Such antibodies are likely to be useful in preventing or treating PD and other LBD.

Analogous methods can be used to screen antibodies for activity in clearing other types of biological entities. The assay can be used to detect clearing activity against virtually any kind of biological entity. Typically, the biological entity has some role in human or animal disease. The biological entity can be provided as a tissue sample or in isolated form. If provided as a tissue sample, the tissue sample is preferably unfixed to allow ready access to components of the tissue sample and to avoid perturbing the conformation of the components incidental to fixing. Examples of tissue samples that can be tested in this assay include cancerous tissue, precancerous tissue, tissue containing benign growths such as warts or moles, tissue infected with pathogenic microorganisms, tissue infiltrated with inflammatory cells, tissue bearing pathological matrices between cells (e.g., fibrinous pericarditis), tissue bearing aberrant antigens, and scar tissue. Examples of isolated biological entities that can be used include alpha-SN, viral antigens or viruses, proteoglycans, antigens of other pathogenic microorganisms, tumor antigens, and adhesion molecules. Such antigens can be obtained from natural sources, recombinant expression or chemical synthesis, among other means. The tissue sample or isolated biological entity is contacted with phagocytic cells bearing Fc receptors, such as monocytes or microglial cells, and an antibody to be tested in a medium. The antibody can be directed to the biological entity under test or to an antigen associated with the entity. In the latter situation, the object is to test whether the biological entity is vicariously phagocytosed with the antigen. Usually, although not necessarily, the antibody and biological entity (sometimes with an associated antigen) are contacted with each other before adding the phagocytic cells. The concentration of the biological entity and/or the associated antigen, if present, remaining in the medium is then monitored. A reduction in the amount or concentration of antigen or the associated biological entity in the medium indicates the antibody has a clearing response against the antigen and/or associated biological entity in conjunction with the phagocytic cells.

Antibodies or other agents can also be screened for activity in clearing Lewy bodies using the in vitro assay described in Example II. Neuronal cells transfected with an expression vector expressing synuclein form synuclein inclusions that can be visualized microscopically. The activity of an antibody or other agent in clearing such inclusions can be determined comparing appearance or level of synuclein in transfected cells treated with agent with appearance or level of synuclein in control cells not treated with the agent. A reduction in size or intensity of synuclein inclusions or a reduction in level of synuclein signals activity in clearing synuclein. The activity can be monitored either by visualizing synuclein inclusions microscopically or by running cell extracts on a gel and visualizing a synuclein band. As noted in Example 1, section 2, the change in level of synuclein is most marked if the extracts are fractionated into cytosolic and membrane fractions, and the membrane fraction is analyzed.

Antibodies or other agents can also be screened for activity in clearing Lewy bodies using the in vivo assay described in Example IX. Briefly, a test antibody is injected into the neocortex of transgenic mice that overexpress human α-synuclein and have intraneuronal α-synuclein aggregates. In one approach, the animals used are 4 to 8 month-old heterozygous transgenic mice overexpressing human wildtype α-synuclein in the brain under the transcriptional control of the PDGF promoter (see Masliah, 2000, *Science* 287:1265-69). The test antibody and controls (e.g., irrelevant, isotype-matched control antibodies) are dissolved in a suitable solution (e.g., sterile phosphate-buffered-saline solution) for injection into mice. For each mouse, 2 μl of a 2 mg/ml antibody solution is injected stereotactically under anesthesia into the deep layers of the parietal neocortex of the right brain hemisphere (ipsilateral side). The left hemispheres (contralateral side) serve as a baseline control for each mouse. Injection sites are sutured and mice monitored until they recovered from anesthesia. Two weeks after injection, mice are euthanized, their brains removed and fixed in 4% paraformaldehyde for 48 h, and cut coronally at 40 μm thickness. Sections around the injection site are stained with an α-synuclein antibody (e.g., ELADW-47, recognizing α-synuclein amino acids 115-122). For each section, intraneuronal α-synuclein aggregates are counted in 4 microscopic fields (20× objective) around the injection site in the ipsilateral hemisphere, and in 4 fields corresponding fields in the contralateral control hemisphere. For each animal the α-synuclein aggregate counts for two sections are added and the difference between the total α-synuclein aggregate count between the two hemisphere is to determine the effect of the test antibody on aggregate clearance for each individual mouse. A reduction in total α-synuclein aggregate count in the treated hemisphere is indicative that the antibodies or other agent has activity in clearing Lewy bodies. Preferably a reduction of at least 10% is observed. More preferably a reduction of at least 20%, at least 40%, at least 60% or at least 80% is observed.

V. Patients Amenable to Anti-Lewy Body Component Treatment Regimes

Patients amenable to treatment include individuals at risk of a synucleinopathic disease but not showing symptoms, as well as patients presently showing symptoms. Patients amenable to treatment also include individuals at risk of disease of a LBD but not showing symptoms, as well as patients presently showing symptoms. Such diseases include Parkinson's disease (including idiopathic Parkinson's disease), DLB, DLBD, LBVAD, pure autonomic failure, Lewy body dysphagia, incidental LBD, inherited LBD (e.g., mutations of the alpha-SN gene, PARK3 and PARK4) and multiple system atrophy (e.g., olivopontocerebellar atrophy, striatonigral degeneration and Shy-Drager syndrome). Therefore, the present methods can be administered prophylactically to individuals who have a known genetic risk of a LBD. Such individuals include those having relatives who have experienced this disease, and those whose risk is determined by analysis of genetic or biochemical markers. Genetic markers of risk toward PD include mutations in the synuclein or Parkin, UCHL1, and CYP2D6 genes; particularly mutations at position 53 of the synuclein gene. Individuals presently suffering from Parkinson's disease can be recognized from its clinical manifestations including resting tremor, muscular rigidity, bradykinesia and postural instability.

In some methods, is free of clinical symptoms, signs and/or risk factors of any amyloidogenic disease and suffers from at least one synucleinopathic disease. In some methods, the patient is free of clinical symptoms, signs and/or risk factors of any disease characterized by extracellular amyloid deposits. In some methods, the patient is free of diseases characterized by amyloid deposits of Aβ peptide. In some methods, the patient is free of clinical symptoms, signs and/or risk factors of Alzheimer's disease. In some methods, the patient is free of clinical symptoms, signs and/or risk factors of Alzheimer's disease, cognitive impairment, mild cognitive impairment and Down's syndrome. In some methods, the patient has concurrent Alzheimer's disease and a disease characterized by Lewy bodies. In some methods, the patient has concurrent Alzheimer's disease and a disease characterized synuclein accumulation. In some methods, the patient has concurrent Alzheimer's and Parkinson's disease.

In asymptomatic patients, treatment can begin at any age (e.g., 10, 20, or 30). Usually, however, it is not necessary to begin treatment until a patient reaches 40, 50, 60, or 70. Treatment typically entails multiple dosages over a period of time. Treatment can be monitored by assaying antibody, or activated T-cell or B-cell responses to the therapeutic agent (e.g., alpha-SN peptide or Aβ, or both) over time. If the response falls, a booster dosage is indicated.

Optionally, presence of absence of symptoms, signs or risk factors of a disease is determined before beginning treatment.

VI. Patients Amenable to Anti-Amyloid Component Treatment Regimes

Patients amenable to treatment include individuals at risk of disease but not showing symptoms, as well as patients presently showing symptoms of amyloidosis. In the case of Alzheimer's disease, virtually anyone is at risk of suffering from Alzheimer's disease if he or she lives long enough. Therefore, the present methods can be administered prophylactically to the general population without the need for any assessment of the risk of the subject patient. The present methods are especially useful for individuals who do have a known genetic risk of Alzheimer's disease or any of the other hereditary amyloid diseases. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and Swedish mutations respectively (see Hardy, TINS, supra). Other markers of risk are mutations in the presenilin genes, PS1 and PS2, and ApoE4, family history of AD, hypercholesterolemia or atherosclerosis. Individuals presently suffering from Alzheimer's disease can be recognized from characteristic dementia, as well as the presence of risk factors described above. In addition, a number of diagnostic tests are available for identifying individuals who have AD. These include measurement of CSF tau and Aβ42 levels. Elevated tau and decreased Aβ42 levels signify the presence of AD. Individuals suffering from Alzheimer's disease can also be diagnosed by MMSE or ADRDA criteria as discussed in the Examples section. In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. Treatment can be monitored by assaying antibody, or activated T-cell or B-cell responses to the therapeutic agent (e.g., NAC) over time, along the lines described in VII Methods of Monitoring and Diagnosis, below. If the response falls, a booster dosage is indicated.

VII. Treatment Regimes

In general treatment regimes involve administering an agent effective to induce an immunogenic response to alpha-SN and/or an agent effective to induce an immunogenic response to Aβ to a patient. In prophylactic applications, pharmaceutical compositions or medicaments are administered to a patient susceptible to, or otherwise at risk of a LBD or another synucleopathic disease in a regime comprising an amount and frequency of administration of the composition or medicament sufficient to eliminate or reduce the risk, lessen the severity, or delay the outset of the disease, including physiological, biochemical, histologic and/or behavioral symptoms of the disease, its complications and intermediate pathological phenotypes presenting during development of the disease. In therapeutic applications, compositions or medicates are administered to a patient suspected of, or already suffering from such a disease in a regime comprising an amount and frequency of administration of the composition sufficient to cure, or at least partially arrest, the symptoms of the disease (physiological, biochemical, histologic and/or behavioral), including its complications and intermediate pathological phenotypes in development of the disease. For example, in some methods treatment effects at least partial clearance of Lewy bodies, at least partial disaggregation of Lewy bodies and/or reduces levels of alpha-synuclein oligomers in synapses. An amount adequate to accomplish therapeutic or prophylactic treatment is defined as a therapeutically- or prophylactically-effective dose. A combination of amount and dosage frequency adequate to accomplish therapeutic or prophylactic treatment is defined as a therapeutically or prophylactically-effective regime. In both prophylactic and therapeutic regimes, agents are usually administered in several dosages until a sufficient immune response has been achieved. Typically, the immune response is monitored and repeated dosages are given if the immune response starts to wane.

In some methods, administration of an agent results in reduction of intracellular levels of aggregated synuclein. In some methods, administration of an agent results in improvement in a clinical symptom of a LBD, such as motor function in the case of Parkinson's disease. In some methods, reduction in intracellular levels of aggregated synuclein or improvement in a clinical symptom of disease is monitored at intervals after administration of an agent.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy. The amount of immunogen depends on whether adjuvant is also administered, with higher dosages being required in the absence of adjuvant. The amount of an immunogen for administration sometimes varies from 1-500 μg per patient and more usually from 5-500 μg per injection for human administration. Occasionally, a higher dose of 1-2 mg per injection is used. Typically about 10, 20, 50 or 100 μg is used for each human injection. The mass of immunogen also depends on the mass ratio of immunogenic epitope within the immunogen to the mass of immunogen as a whole. Typically, $10^{-3}$ to $10^{-5}$ micromoles of immunogenic epitope are used for microgram of immunogen. The timing of injections can vary significantly from once a day, to once a year, to once a decade. On any given day that a dosage of immunogen is given, the dosage is greater than 1 μg/patient and usually greater than 10 μg/patient if adjuvant is also administered, and greater than 10 μg/patient and usually greater than 100 μg/patient in the absence of adjuvant. A typical regimen consists of an immunization followed by booster injections at time intervals, such as 6 week intervals. Another regimen consists of an immunization followed by booster injections 1, 2 and 12 months later. Another regimen entails an injection every two months for life. Alternatively, booster injections can be on an irregular basis as indicated by monitoring of immune response.

For passive immunization with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg or, in other words, 70 mgs or 700 mgs or within the range of 70-700 mgs, respectively, for a 70 kg patient. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to alpha-SN in the patient. In some methods, dosage is adjusted to achieve a plasma antibody concentration of 1-1000 ug/ml and in some methods 25-300 ug/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding immunogens range from about 10 ng to 1 g, 100 ng to 100 mg, 1 µg to 10 mg, or 30-300 µg DNA per patient. Doses for infectious viral vectors vary from 10-100, or more, virions per dose.

Agents for inducing an immune response can be administered by parenteral, topical, intravenous, oral, subcutaneous, intraarterial, intracranial, intrathecal, intraperitoneal, intranasal or intramuscular means for prophylactic and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection or intravenous infusion are preferred for administration of antibody. In some methods, particular therapeutic antibodies are injected directly into the cranium. In some methods, antibodies are administered as a sustained release composition or device, such as a Medipad™ device.

As noted above, agents inducing an immunogenic response against alpha-SN and Aβ respectively can be administered in combination. The agents can be combined in a single preparation or kit for simultaneous, sequential or separate use. The agents can occupy separate vials in the preparation or kit or can be combined in a single vial. These agents of the invention can optionally be administered in combination with other agents that are at least partly effective in treatment of LBD. In the case of Parkinson's Disease and Down's syndrome, in which LBs occur in the brain, agents of the invention can also be administered in conjunction with other agents that increase passage of the agents of the invention across the blood-brain barrier.

Immunogenic agents of the invention, such as peptides, are sometimes administered in combination with an adjuvant. A variety of adjuvants can be used in combination with a peptide, such as alpha-SN, to elicit an immune response. Preferred adjuvants augment the intrinsic response to an immunogen without causing conformational changes in the immunogen that affect the qualitative form of the response. Preferred adjuvants include aluminum hydroxide and aluminum phosphate, 3 De-O-acylated monophosphoryl lipid A (MPL™) (see GB 2220211 (RIBI ImmunoChem Research Inc., Hamilton, Mont., now part of Corixa). Stimulon™ QS-21 is a triterpene glycoside or saponin isolated from the bark of the Quillaja Saponaria Molina tree found in South America (see Kensil et al., in *Vaccine Design: The Subunit and Adjuvant Approach* (eds. Powell & Newman, Plenum Press, NY, 1995); U.S. Pat. No. 5,057,540), (Aquila BioPharmaceuticals, Framingham, Mass.). Other adjuvants are oil in water emulsions (such as squalene or peanut oil), optionally in combination with immune stimulants, such as monophosphoryl lipid A (see Stoute et al., *N. Engl. J. Med.* 336, 86-91 (1997)), pluronic polymers, and killed mycobacteria. Another adjuvant is CpG (WO 98/40100). Alternatively, alpha-SN or Aβ can be coupled to an adjuvant. However, such coupling should not substantially change the conformation of alpha-SN so as to affect the nature of the immune response thereto. Adjuvants can be administered as a component of a therapeutic composition with an active agent or can be administered separately, before, concurrently with, or after administration of the therapeutic agent.

A preferred class of adjuvants is aluminum salts (alum), such as alum hydroxide, alum phosphate, alum sulfate. Such adjuvants can be used with or without other specific immunostimulating agents such as MPL or 3-DMP, QS-21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2' dipalmitoyl-sn-glycero-3-hydroxyphosphoryloxy)-ethylamine (MTP-PE), N-acetylglucosaminyl-N-acetylmuramyl-L-A1-D-isoglu-L-Ala-dipalmitoxy propylamide (DTP-DPP) Theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi ImmunoChem, Hamilton, Mont.) containing 2% squalene, 0.2% Tween 80, and one or more bacterial cell wall components from the group consisting of monophosphoryllipid A (MPL), trehalose dimycolate (TDM), and cell wall skeleton (CWS), preferably MPL+CWS (Detox™).

Another class of preferred adjuvants is saponin adjuvants, such as Stimulon™ (QS-21, Aquila, Framingham, Mass.) or particles generated therefrom such as ISCOMs (immunostimulating complexes) and ISCOMATRIX. Other adjuvants include RC-529, GM-CSF and Complete Freund's Adjuvant (CFA) and Incomplete Freund's Adjuvant (IFA). Other adjuvants include cytokines, such as interleukins (e.g., IL-1, IL-2, IL-4, IL-6, IL-12, IL13, and IL-15), macrophage colony stimulating factor (M-CSF), granulocyte-macrophage colony stimulating factor (GM-CSF), and tumor necrosis factor (TNF). Another class of adjuvants is glycolipid analogues including N-glycosyl amides, N-glycosylureas and N-glycosylcarbamates, each of which is substituted in the sugar residue by an amino acid, as immuno-modulators or adjuvants (see U.S. Pat. No. 4,855,283). Heat shock proteins, e.g., HSP70 and HSP90, may also be used as adjuvants.

An adjuvant can be administered with an immunogen as a single composition, or can be administered before, concurrent with or after administration of the immunogen. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS-21 are preferred. Optionally, two or more different adjuvants can be used simultaneously. Preferred combinations include alum with MPL, alum with QS-21, MPL with QS-21, MPL or RC-529 with GM-CSF, and alum, QS-21 and MPL together. Also, Incomplete Freund's adjuvant can be used (Chang et al., *Advanced Drug Delivery Reviews* 32, 173-186 (1998)), optionally in combination with any of alum, QS-21, and MPL and all combinations thereof.

Agents of the invention are often administered as pharmaceutical compositions comprising an active therapeutic agent, i.e., and a variety of other pharmaceutically acceptable components. See *Remington's Pharmaceutical Science* (15th ed., Mack Publishing Company, Easton, Pa., 1980). Thus, any agent (e.g., fragment of alpha synuclein or antibody specifically binding to alpha synuclein) can be used in the manufacture of a medicament for treatment of synucleinopathic disease. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl. Compositions for parenteral administration are typically substantially sterile, substantially isotonic and manufactured under GMP conditions of the FDA or similar body. For example, compositions containing biologics are typically sterilized by filter sterilization. Compositions can be formulated for single dose administration.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, *Science* 249, 1527 (1990) and Hanes, *Advanced Drug Delivery Reviews* 28, 97-119 (1997). The agents of this invention can be administered in the form of a depot injection or implant preparation which can be formulated in such a manner as to permit a sustained or pulsatile release of the active ingredient. Compositions can be formulated in unit dosage form (i.e., the formulation contains sufficient of the active ingredient for one dosage to one patient).

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins (See Glenn et al., *Nature* 391, 851 (1998)). Co-administration can be achieved by using the components as a mixture or as linked molecules obtained by chemical crosslinking or expression as a fusion protein.

Alternatively, transdermal delivery can be achieved using a skin path or using transferosomes (Paul et al., *Eur. J. Immunol.* 25, 3521-24 (1995); Cevc et al., *Biochem. Biophys. Acta* 1368, 201-15 (1998)).

VIII. Methods of Monitoring and Methods of Diagnosis

The invention provides methods of detecting an immune response against alpha-SN peptide and/or Aβ peptide in a patient suffering from or susceptible to a LBD. The methods are particularly useful for monitoring a course of treatment being administered to a patient. The methods can be used to monitor both therapeutic treatment on symptomatic patients and prophylactic treatment on asymptomatic patients. The methods are useful for monitoring both active immunization (e.g., antibody produced in response to administration of immunogen) and passive immunization (e.g., measuring level of administered antibody).

1. Active Immunization

Some methods entail determining a baseline value of an immune response in a patient before administering a dosage of agent, and comparing this with a value for the immune response after treatment. A significant increase (i.e., greater than the typical margin of experimental error in repeat measurements of the same sample, expressed as one standard deviation from the mean of such measurements) in value of the immune response signals a positive treatment outcome (i.e., that administration of the agent has achieved or augmented an immune response). If the value for immune response does not change significantly, or decreases, a negative treatment outcome is indicated. In general, patients undergoing an initial course of treatment with an immunogenic agent are expected to show an increase in immune response with successive dosages, which eventually reaches a plateau. Administration of agent is generally continued while the immune response is increasing. Attainment of the plateau is an indicator that the administered of treatment can be discontinued or reduced in dosage or frequency.

In other methods, a control value (i.e., a mean and standard deviation) of immune response is determined for a control population. Typically the individuals in the control population have not received prior treatment. Measured values of immune response in a patient after administering a therapeutic agent are then compared with the control value. A significant increase relative to the control value (e.g., greater than one standard deviation from the mean) signals a positive treatment outcome. A lack of significant increase or a decrease signals a negative treatment outcome. Administration of agent is generally continued while the immune response is increasing relative to the control value. As before, attainment of a plateau relative to control values in an indicator that the administration of treatment can be discontinued or reduced in dosage or frequency.

In other methods, a control value of immune response (e.g., a mean and standard deviation) is determined from a control population of individuals who have undergone treatment with a therapeutic agent and whose immune responses have reached a plateau in response to treatment. Measured values of immune response in a patient are compared with the control value. If the measured level in a patient is not significantly different (e.g., more than one standard deviation) from the control value, treatment can be discontinued. If the level in a patient is significantly below the control value, continued administration of agent is warranted. If the level in the patient persists below the control value, then a change in treatment regime, for example, use of a different adjuvant may be indicated.

In other methods, a patient who is not presently receiving treatment but has undergone a previous course of treatment is monitored for immune response to determine whether a resumption of treatment is required. The measured value of immune response in the patient can be compared with a value of immune response previously achieved in the patient after a previous course of treatment. A significant decrease relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant decrease relative to the control level (i.e., more than a standard deviation) is an indicator that treatment should be resumed in a patient.

The tissue sample for analysis is typically blood, plasma, serum, mucous or cerebrospinal fluid from the patient. The sample is analyzed for indication of an immune response to any form of alpha-SN, typically NAC, or A$\beta$. The immune response can be determined from the presence of, e.g., antibodies or T-cells that specifically bind to alpha-SN or AB. ELISA methods of detecting antibodies specific to alpha-SN are described in the Examples section. Methods of detecting reactive T-cells have been described above (see Definitions). In some methods, the immune response is determined using a clearing assay, such as described in Section III above. In such methods, a tissue or blood sample from a patient being tested is contacted with LBs (e.g., from a synuclein/hAPP transgenic mouse) and phagocytic cells bearing Fc receptors. Subsequent clearing of the LBs is then monitored. The existence and extent of clearing response provides an indication of the existence and level of antibodies effective to clear alpha-SN in the tissue sample of the patient under test.

2. Passive Immunization

In general, the procedures for monitoring passive immunization are similar to those for monitoring active immunization described above. However, the antibody profile following passive immunization typically shows an immediate peak in antibody concentration followed by an exponential decay. Without a further dosage, the decay approaches pretreatment levels within a period of days to months depending on the half-life of the antibody administered. For example the half-life of some human antibodies is of the order of 20 days.

In some methods, a baseline measurement of antibody to alpha-SN in the patient is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dosage of antibody is administered. In some methods, peak or subsequent measured levels less background are compared with reference levels previously determined to constitute a beneficial prophylactic or therapeutic treatment regime in other patients. If the measured antibody level is significantly less than a reference level (e.g., less than the mean minus one standard deviation of the reference value in population of patients benefiting from treatment) administration of an additional dosage of antibody is indicated.

3. Diagnostic Kits

The invention further provides diagnostic kits for performing the diagnostic methods described above. Typically, such kits contain an agent that specifically binds to antibodies to alpha-SN. The kit can also include a label. For detection of antibodies to alpha-SN, the label is typically in the form of labeled anti-idiotypic antibodies. For detection of antibodies, the agent can be supplied prebound to a solid phase, such as to the wells of a microtiter dish. Kits also typically contain labeling providing directions for use of the kit. The labeling may also include a chart or other correspondence regime correlating levels of measured label with levels of antibodies to alpha-SN. The term labeling refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

The invention also provides diagnostic kits for performing in vivo imaging. Such kits typically contain an antibody binding to an epitope of alpha-SN, e.g., within NAC. Preferably, the antibody is labeled or a secondary labeling reagent is included in the kit. Preferably, the kit is labeled with instructions for performing an in vivo imaging assay.

In one embodiment the antibody is selected from mAb 6H7, mAb 8A5, mAb 9E4, mAb 1H7, or mAb 11A5 or a binding fragment thereof. The aforementioned anti-alpha synuclein antibodies also may be used in assays as described in U.S. patent publication No. 2005196818, the entire content of which is incorporated herein by reference.

IX. In Vivo Imaging

The invention provides methods of in vivo imaging LBs in a patient. Such methods are useful to diagnose or confirm diagnosis of PD, or other disease associated with the presence of LBs in the brain, or susceptibility thereto. For example, the methods can be used on a patient presenting with symptoms of dementia. If the patient has LBs, then the patient is likely suffering from, e.g. PD. The methods can also be used on asymptomatic patients. Presence of abnormal deposits of amyloid indicates susceptibility to future symptomatic disease. The methods are also useful for monitoring disease progression and/or response to treatment in patients who have been previously diagnosed with Parkinson's disease.

The methods work by administering a reagent, such as antibody that binds to alpha-SN in the patient and then detecting the agent after it has bound. Preferred antibodies bind to alpha-SN deposits in a patient without binding to full length NACP polypeptide. Antibodies binding to an epitope of alpha-SN within NAC are particularly preferred. If desired, the clearing response can be avoided by using antibody fragments lacking a full length constant region, such as Fabs. In some methods, the same antibody can serve as both a treatment and diagnostic reagent. In general, antibodies binding to epitopes N-terminal of alpha-SN do not show as strong signal as antibodies binding to epitopes C-terminal, presumably because the N-terminal epitopes are inaccessible in LBs (Spillantini et al PNAS, 1998). Accordingly, such antibodies are less preferred.

Diagnostic reagents can be administered by intravenous injection into the body of the patient, or directly into the brain by intracranial injection or by drilling a hole through the skull. The dosage of reagent should be within the same ranges as for treatment methods. Typically, the reagent is labeled, although in some methods, the primary reagent with affinity for alpha-SN is unlabelled and a secondary labeling agent is used to bind to the primary reagent. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size and/or intensity of labeled loci to corresponding base line values. The base line values can represent the mean levels in a population of undiseased individuals. Base line values can also represent previous levels determined in the same patient. For example, base line values can be determined in a patient before beginning treatment, and measured values thereafter compared with the base line values. A decrease in values relative to base line signals a positive response to treatment.

EXAMPLES

Example I

Immunization of Human Alpha-Synuclein Transgenic Mice with Human Alpha-Synuclein Results in the Production of High Titer Anti-Alpha-Synuclein Antibodies That Cross the Blood-Brain Barrier Full-length recombinant human alpha-SN was resuspended at a concentration of 1 mg/ml in 1× phosphate buffered saline (PBS). For each injection, 50 µl of alpha-SN was used; giving a final concentration of 50 µg per injection to which 150 µl of 1×PBS was added. Complete Freund's adjuvant (CFA) was then added 1:1 to either alpha-SN or PBS alone (control), vortexed and sonicated to completely resuspend the emulsion. For the initial injections, eight D line human alpha-SN transgenic (tg) single transgenic 4-7 months old mice (Masliah, et al. Science 287:1265-1269 (2000) received injections of human alpha-SN in CFA and, as control, four D line human alpha-SN tg mice received injections of PBS in CFA. Mice received a total of 6 injections. Three injections were performed at two weeks intervals and then 3 injections at one month intervals. Animals were sacrificed using NIH Guidelines for the humane treatment of animals 5 months after initiation of the experiment. After blood samples were collected for determination of antibody titers, brains were immersion-fixed for 4 days in 4% paraformaldehyde in PBS. Levels of antibodies against human alpha-SN by ELISA are shown in Table 1. The treated mice are divided into two groups by titer. The first group developed a moderate titer of 2-8,000. The second group developed a high titer of 12000-30000. No titer was found in control mice. Neuropathological analysis showed that mice producing high titers had a marked decrease in the size of synuclein incusions. Mice producing moderate titers showed a smaller decrease. FIG. 2 (panels a-d) show synuclein inclusions in (a) a nontransgenic mouse, (b) a transgenic mouse treated with CFA only, (c) a transgenic mouse immunized with alpha synuclein and CFA that developed a moderate titer and (d) a transgenic mouse immunized with alpha synuclein and CFA that developed a higher titer. Samples were visualized by immunostaining with an anti-human alpha-SN antibody. FIG. 2 shows synuclein inclusions in panel (b) but not panel (a). In panel (c), treated mouse, moderate titers, the inclusions are somewhat reduced in intensity. In panel (d) the inclusions are markedly reduced in intensity. Panels (e)-(h) show levels of anti-IgG in the brains same four mice as panels (a) to (d) respectively. It can be seen that IgG is present in panels (g) and to a greater extent in panel (h). The data shows that peripherally administered antibodies to alpha-SN cross the blood brain barrier and reach the brain. Panels (i) to (l) showing staining for GAP, a marker of astroglial cells, again for the same four mice as in the first two rows of the figure. It can be seen that panels (k) and (l) show moderately increased staining compared with (i) and (j). These data show that clearing of synuclein deposits is accompanied by a mild astroglial and microglial reaction.

TABLE 1

| Group | Genotype | n = | Age at Sac | Treatment/Length | Titers | Syn (+) inclusions/mm2 |
|---|---|---|---|---|---|---|
| I | Syn Tg | 4 | 10-13 mo | a-syn + CFA 50 ug/inj for 3 mo sac'd 3 mo later | 2,000-8,000 | 15-29 |
| II | Syn Tg | 4 | 10-13 mo | a-syn + CFA 50 ug/inj for 3 mo sac'd 3 mo later | 12,000-30,000 | 10-22 |
| III | Syn Tg | 4 | 10-13 mo | PBS + CFA for 3 mo sac'd 3 mo later | 0 | 18-29 |

Example II

In Vitro Screen for Antibodies Clearing Synuclein Inclusions

Figure 4:
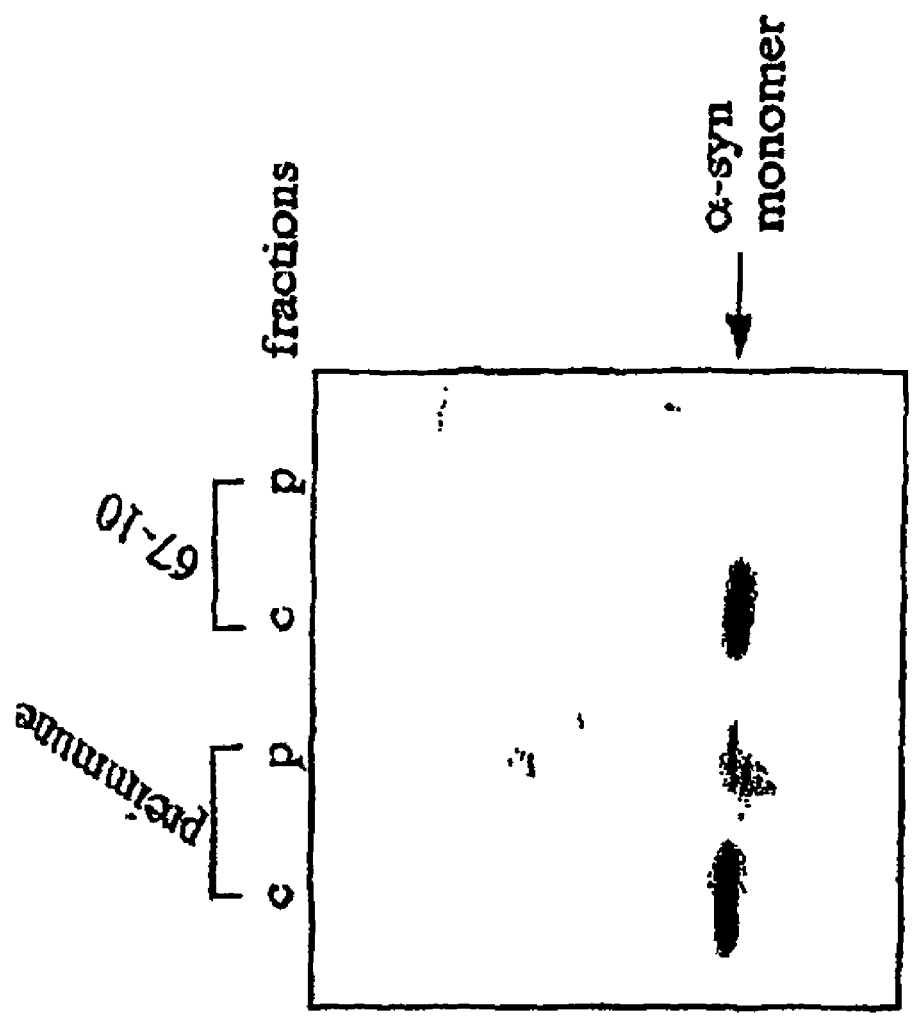
FIG. 4 is a Western blot of synuclein levels in the cytoplasm (C) and membranes (P) of GT1-7 α-syn cells treated with preimmune sera and with 67-10 antibody at a concentration of (1:50) for 48 hours prior to analysis.

GT1-7 neuronal cell (Hsue et al. Am. J. Pathol. 157:401-410 (2000)) were transfected with a pCR3.1-T expression vector (Invitrogen, Carlsbad, Calif.) expressing murine alpha-SN and compared with cells transfected with expression vector alone (FIGS. 3, B and A respectively). Cells transfected with vector alone (A) have a fibroblastic appearance while cells transfected with alpha-SN are rounded, with inclusion bodies at the cell surface visible via both light and confocal scanning microscopy. Transfected cells were then treated with rabbit preimmune serum (FIG. 3 C) or 67-10, an affinity purified rabbit polyclonal antibody against a murine alpha-SN C terminal residues 131-140 (Iwai, et al., Neuron 14:467 (1995) (FIG. 3D). It can be seen that the inclusion bodies stain less strongly in panel D than in panel C indicating that the antibody against alpha synuclein was effective in clearing or preventing the development of inclusions. FIG. 4 shows a gel analysis of particulate and cytosolic fractions of GT1-7 transfected cells treated with the rabbit preimmune serum and 67-10 polyclonal antibody. It can be seen that the synuclein levels in the cytosolic fraction is largely unchanged by treatment with preimmune serum or antibody to alpha-SN. However, the alpha-SN band disappears in the membrane fraction of GT1-7 cells treated with antibody to alpha-SN. These data indicates that the alpha synuclein antibody activity results in the clearance of synuclein associated with the cellular membrane.

Transfected GT1-7 cells can be used to screen antibodies for activity in clearing synuclein incusions with detection either by immunohistochemical analysis, light microscopy as in FIG. 3 or by gel analysis as in FIG. 4.

Example III

Prophylactic and Therapeutic Efficacy of Immunization with Alpha-Synuclein i. Immunization of Human Alpha-synuclein tg Mice For this study, heterozygous human alpha-SN transgenic (tg) mice (Line D) (Masliah et al., 2000, Science 286:1265-69) and nontransgenic (nontg) controls are used. Experimental animals are divided into 3 groups. For group I, the preventive effects of early immunization by immunizing mice for 8 months beginning at 2 months of age are tested. For group II, young adult mice are vaccinated for 8 months beginning at the age of 6 months to determine whether immunization can reduce disease progression once moderate pathology had been established. For group III, older mice are immunized for 4 months beginning at the age of 12 months to determine whether immunization can reduce the severity of symptoms once robust pathology has been established. For all groups, mice are immunized with either recombinant human alpha-SN plus CFA or CFA alone, and for each experiment 20 tg and 10 nontg mice are used. Of them, 10 tg mice are immunized with human alpha-SN+CFA and other 10 tg with CFA alone. Similarly, 5 nontg mice are immunized with human alpha-SN+CFA and the other 5 with CFA alone. Briefly, the immunization protocol consists of an initial injection with purified recombinant human alpha-SN (2 mg/ml) in CFA, followed by a reinjection 1 month later with human alpha-SN in combination with IFA. Mice are then re-injected with this mixture once a month. In a small subset of human alpha-SN tg (n=3/each; 6-months-old) and nontg (n=3/each; 6-month-old) mice, additional experiments consisting of immunization with murine (m) alpha-SN, human beta synuclein or mutant (A53T) human alpha-SN are performed.

Levels of alpha-SN antibody are determined using 96-well microtiter plates coated with 0.4 µg per well of purified full-length alpha-SN by overnight incubation at 4° C. in sodium carbonate buffer, pH 9.6. Wells are washed 4× with 200 µL each PBS containing 0.1% Tween and blocked for 1 hour in PBS-1% BSA at 37° C. Serum samples are serially diluted "in-well", 1:3, starting in row A, ranging from a 1:150 to 1:328,050 dilution. For control experiments, a sample of mouse monoclonal antibody is run against alpha-SN, no protein, and buffer-only blanks. The samples are incubated overnight at 4° C. followed by a 2-hour incubation with goat anti-mouse IgG alkaline phosphatase-conjugated antibody (1:7500, Promega, Madison, Wis.). Atto-phos® alkaline phosphatase fluorescent substrate is then added for 30 minutes at room temperature. The plate is read at an excitation wavelength of 450 nm and an emission wavelength of 550 nm. Results are plotted on a semi-log graph with relative fluorescence units on the ordinate and serum dilution on the abscissa. Antibody titer is defined as the dilution at which there was a 50% reduction from maximal antibody binding.

For each group, at the end of the treatment, mice undergo motor assessment in the rotarod, as described (Masliah, et al., (2000)). After analysis, mice are euthanized and brains are removed for detailed neurochemical and neuropathological analysis as described below. Briefly, the right hemibrain is frozen and homogenized for determinations of aggregated and non-aggregated human alpha-SN immunoreactivity by Western blot (Masliah, et al. (2000)). The left hemibrain is fixed in 4% paraformaldehyde, serially sectioned in the vibratome for immunocytochemistry and ultrastructural analysis.

ii. Immunocytochemical and Neuropathological Analysis.

In order to determine if immunization decreases, human alpha-SN aggregation sections are immunostained with a rabbit polyclonal antibody against human alpha-SN (1:500). After an overnight incubation at 4° C., sections are incubated with biotinylated anti-rabbit secondary antibody followed by Avidin D-Horseradish peroxidase (HRP) complex (1:200, ABC Elite, Vector). Sections are also immunostained with biotinylated anti-rabbit, mouse or human secondary alone. The experiments with the anti-mouse secondary determine whether the antibodies against human alpha-SN cross into the brain. The reaction is visualized with 0.1% 3,3-diaminobenzidine tetrahydrochloride (DAB) in 50 mM Tris-HCl (pH 7.4) with 0.001% $H_2O_2$ and sections are then mounted on slided under Entellan. Levels of immunoreactivity are semiquantitatively assessed by optical densitometry using the Quantimet 570C. These sections are also studied by image analysis to determine the numbers of alpha-SN immunoreactive inclusions and this reliable measure of alpha-SN aggregation acts as a valuable index of the anti-aggregation effects of vaccination (Masliah, et al. (2000)).

Analysis of patterns of neurodegeneration is achieved by analyzing synaptic and dendritic densities in the hippocampus, frontal cortex, temporal cortex and basal ganglia utilizing vibratome sections double-immunolabeled for synaptophysin and microtubule-associated protein 2 (MAP2) and visualized with LSCM. Additional analysis of neurodegeneration is achieved by determining tyrosine hydroxylase (TH) immunoreactivity in the caudoputamen and substantia nigra (SN) as previously described (Masliah, et al. (2000)). Sections will be imaged with the LSCM and each individual image is interactively thresholded such that the TH-immunoreactive terminals displaying pixel intensity within a linear range are included. A scale is set to determine the pixel to μm ratio. Then, this information is used to calculate the % area of the neuropil covered by TH-immunoreactive terminals. These same sections are also utilized to evaluate the numbers of TH neurons in the SN.

To assess the patterns of immune response to immunization, immunocytochemical and ultrastructural analysis with antibodies against human GFAP, MCH class II, Mac 1, TNF-alpha, IL1beta and IL6 are performed in the brain sections of nontg and alpha-SN tg mice immunized with recombinant human alpha-SN and control immunogens.

iii. Behavioral Analysis.

For locomotor activity mice are analyzed for 2 days in the rotarod (San Diego) Instruments, San Diego, Calif.), as previously described (Masliah, et al. (2000)). On the first day mice are trained for 5 trials: the first one at 10 rpm, the second at 20 rpm and the third to fifth at 40 rpm. On the second day, mice are tested for 7 trials at 40 rpm each. Mice are placed individually on the cylinder and the speed of rotation is increased from 0 to 40 rpm over a period of 240 sec. The length of time mice remain on the rod (fall Latency) is recorded and used as a measure of motor function.

Example IV

Immunization with Alpha-Synuclein Fragments

Human alpha-SN transgenic mice 10-13 months of age are immunized with 9 different regions of alpha-SN to determine which epitopes convey the efficacious response. The 9 different immunogens and one control are injected i.p. as described above. The immunogens include four human alpha-SN peptide conjugates, all coupled to sheep anti-mouse IgG via a cystine link. Alpha-SN and PBS are used as positive and negative controls, respectively. Titers are monitored as above and mice are euthanized at the end of 3-12 months of injections. Histochemistry, alpha-SN levels, and toxicology analysis is determined post mortem.

i. Preparation of Immunogens

Preparation of coupled alpha-SN peptides: H alpha-SN peptide conjugates are prepared by coupling through an artificial cysteine added to the alpha-SN peptide using the crosslinking reagent sulfo-EMCS. The alpha-SN peptide derivatives are synthesized with the following final amino acid sequences. In each case, the location of the inserted cysteine residue is indicated by underlining.

alpha-synuclein 60-72 (NAC region) peptide:

NH2-KEQVTNVCGGAVVT-COOH    (SEQ ID NO: 54)

alpha-synuclein 73-84 (NAC region) peptide:

NH2-GVTAVAQKTVECG-COOH    (SEQ ID NO: 55)

alpha-synuclein 102-112 peptide:

(SEQ ID NO: 56)
NH2-C-amino-heptanoic acid- KNEEGAPCQEG-COOH alpha-synuclein 128-140 peptide:

Ac-NH-PSEEGYQDYEPECA-COOH    (SEQ ID NO: 57)

To prepare for the coupling reaction, ten mg of sheep anti-mouse IgG (Jackson ImmunoResearch Laboratories) is dialyzed overnight against 10 mM sodium borate buffer, pH 8.5. The dialyzed antibody is then concentrated to a volume of 2 mL using an Amicon Centriprep tube. Ten mg sulfo-EMCS [N(ε-maleimidocuproyloxy)succinimide] (Molecular Sciences Co.) is dissolved in one mL deionized water. A 40-fold molar excess of sulfo-EMCS is added drop wise with stirring to the sheep anti-mouse IgG and then the solution is stirred for an additional ten min. The activated sheep anti-mouse IgG is purified and buffer exchanged by passage over a 10 mL gel filtration column (Pierce Presto Column, obtained from Pierce Chemicals) equilibrated with 0.1 M NaPO4, 5 mM EDTA, pH 6.5. Antibody containing fractions, identified by absorbance at 280 nm, are pooled and diluted to a concentration of approximately 1 mg/mL, using 1.4 mg per OD as the extinction coefficient. A 40-fold molar excess of alpha-SN peptide is dissolved in 20 mL of 10 mM NaPO4, pH 8.0, with the exception of the alpha-SN peptide for which 10 mg is first dissolved in 0.5 mL of DMSO and then diluted to 20 mL with the 10 mM NaPO4 buffer. The peptide solutions are each added to 10 mL of activated sheep anti-mouse IgG and rocked at room temperature for 4 hr. The resulting conjugates are concentrated to a final volume of less than 10 mL using an Amicon Centriprep tube and then dialyzed against PBS to buffer exchange the buffer and remove free peptide. The conjugates are passed through 0.22 μm-pore size filters for sterilization and then aliquoted into fractions of 1 mg and stored frozen at −20° C. The concentrations of the conjugates are determined using the BCA protein assay (Pierce Chemicals) with horse IgG for the standard curve. Conjugation is documented by the molecular weight increase of the conjugated peptides relative to that of the activated sheep anti-mouse IgG.

Example V

Passive Immunization with Antibodies to Alpha-Synuclein

Human alpha-SN mice each are injected with 0.5 mg in PBS of anti-alpha-SN monoclonals as shown below. All antibody preparations are purified to have low endotoxin levels. Monoclonals can be prepared against a fragment by injecting the fragment or longer form of alpha-SN into a mouse, preparing hybridomas and screening the hybridomas for antibody that specifically binds to a desired fragment of alpha-SN without binding to other nonoverlapping fragments of alpha-SN.

Mice are injected ip as needed over a 4 month period to maintain a circulating antibody concentration measured by ELISA titer of greater than 1:1000 defined by ELISA to alpha-SN or other immunogen. Titers are monitored as above and mice are euthanized at the end of 6 months of injections. Histochemistry, alpha-SN levels and toxicology are performed post mortem.

Example VI

Aβ Immunization of Syn/APP Transgenic Mice

Figure 5:
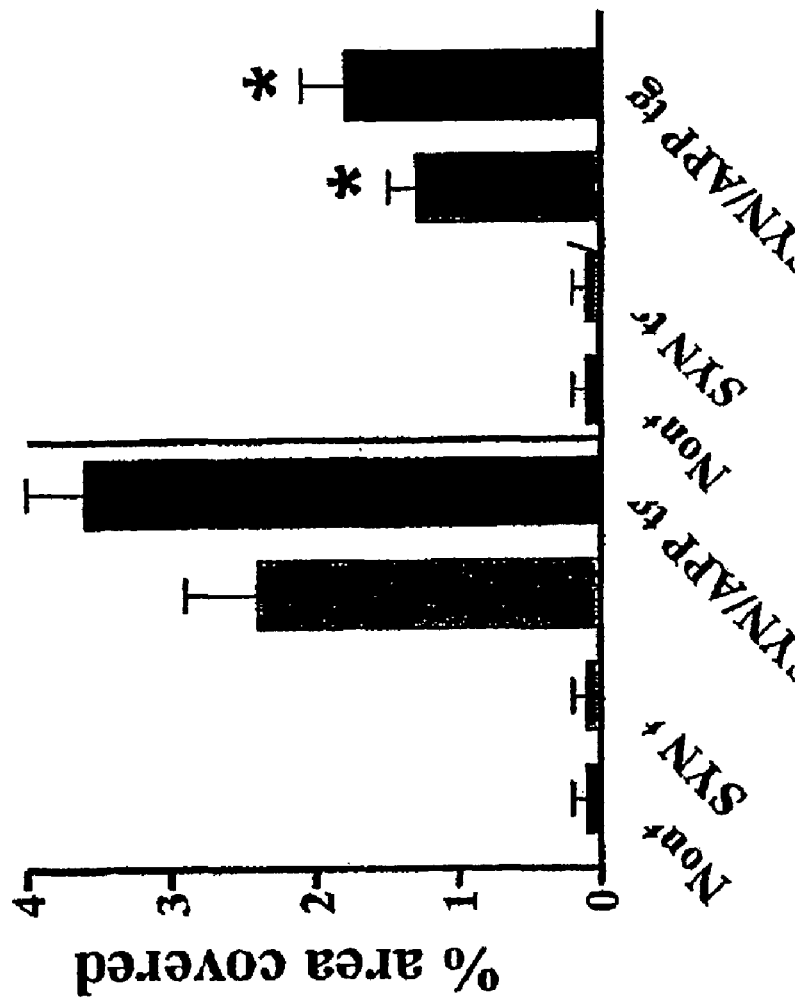
FIG. 5 shows the results of studies of the effect of Aβ1-42 immunization amyloid deposition in the brains of nontransgenic, SYN, APP and SYN/APP transgenic mice. The detectable amyloid levels seen in APP and SYN/APP mice are reduced by Aβ1-42 immunization.
Figure 6:
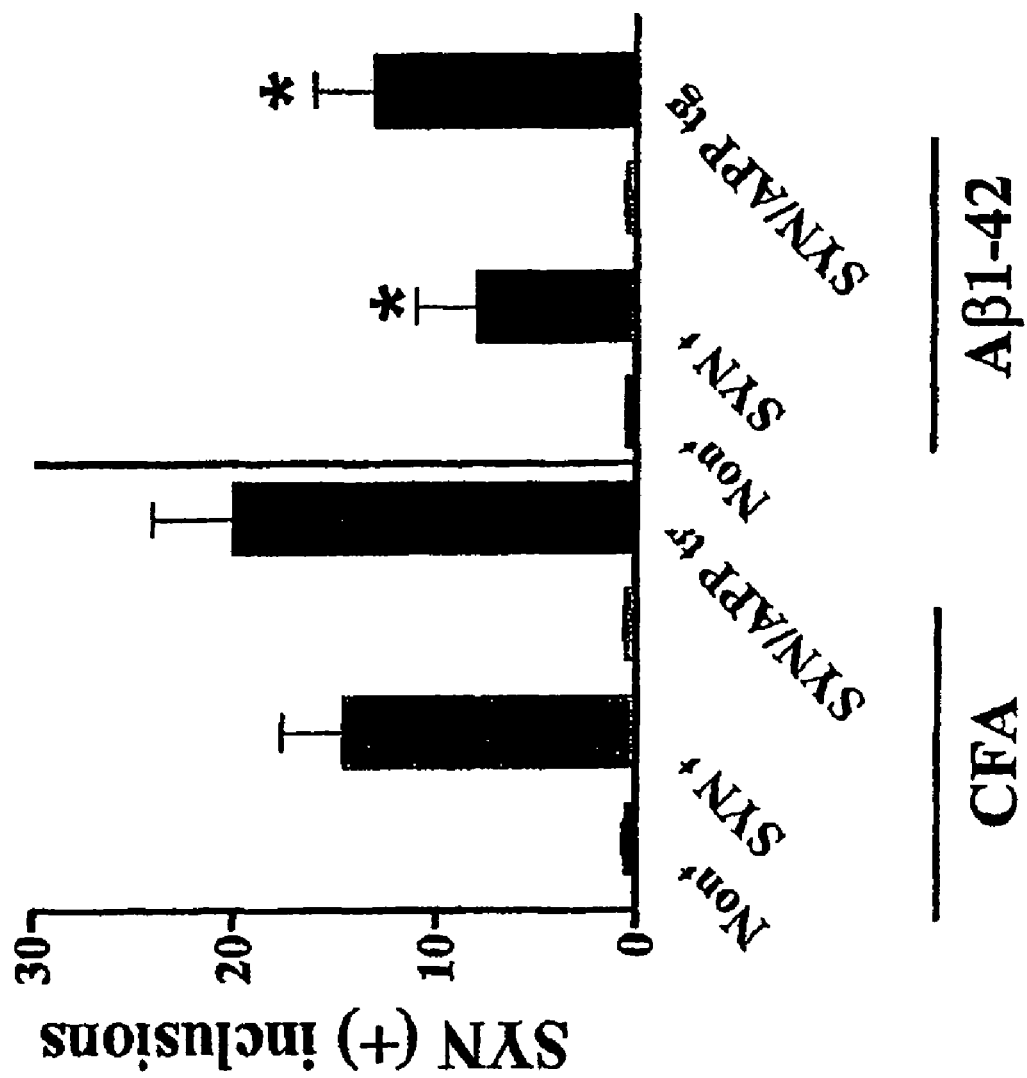
FIG. 6 shows the results of studies of the effect of Aβ1-42 immunization upon synuclein inclusion formation in the brains of nontransgenic, SYN, APP and SYN/APP transgenic mice. Synulcein inclusions detected in SYN and SYN/APP mice are reduced by Aβ1-42 immunization.
Figure 7:
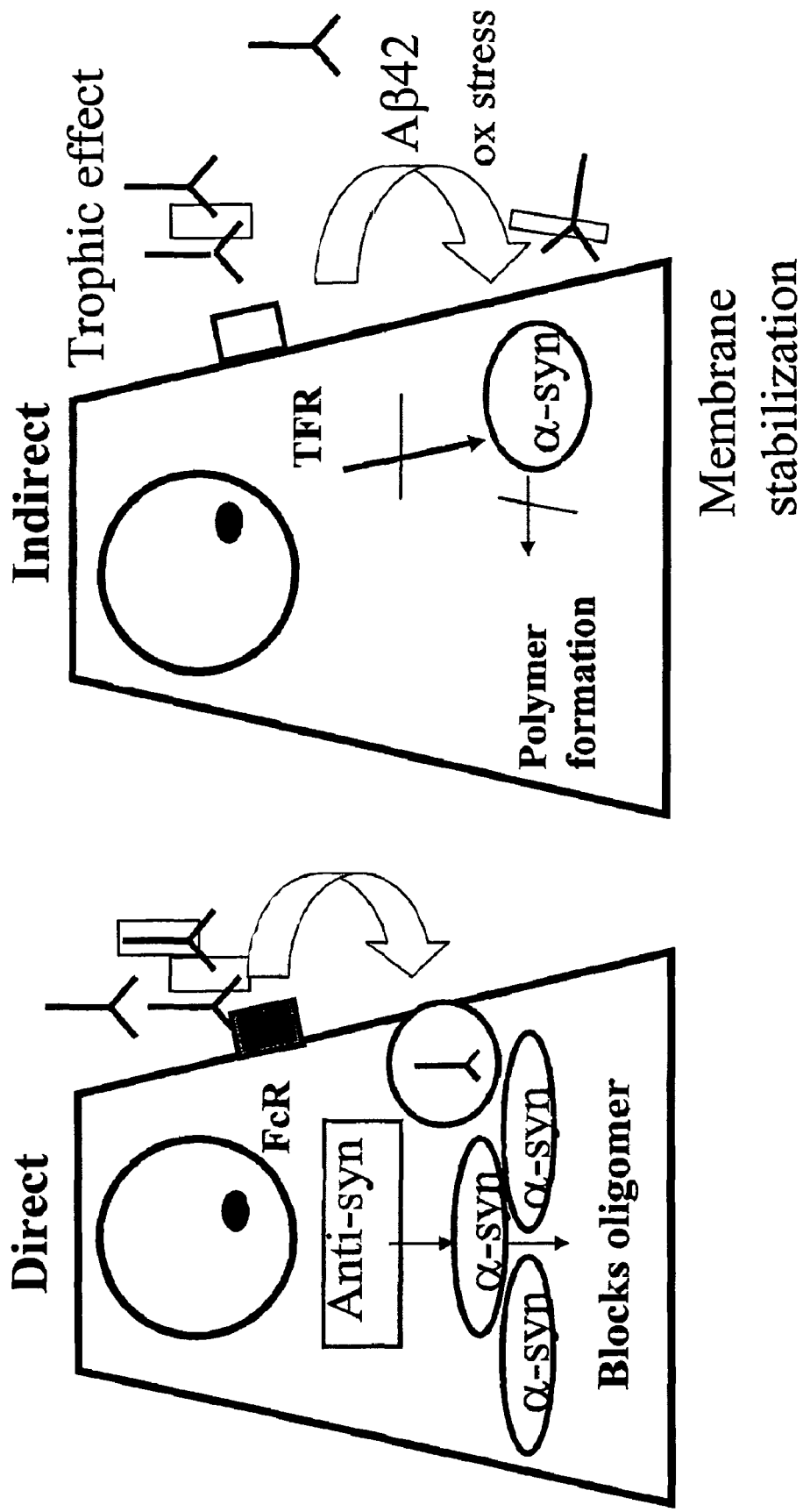
FIG. 7 shows direct and indirect mechanisms by which antibodies block alpha-SN aggregation.

This experiment compares the effects of Aβ immunization on three types of transgenic mice: transgenic mice with an alpha synuclein transgene (SYN), APP mice with an APP transgene (Games et al.) and double transgenic SYN/APP mice produced by crossing the single transgenic. The double transgenic mice are described in Masliah et al., PNAS USA 98:12245-12250 (2001). These mice represent a model of individuals having both Alzheimer's and Parkinson's disease. Table 2 shows the different groups, the age of the mice used in the study, the treatment procedure and the titer of antibodies to Aβ. It can be seen that a significant titer was generated in all three types of mice. FIG. 5 shows the % area covered by amyloid plaques of Aβ in the brain determined by examination of brain sections from treated subjects by microscopy. Substantial deposits accumulate in the APP and SYN/APP mice but not in the SYN mice or nontransgenic controls. The deposits are greater in the SYN/APP double transgenic mice. Immunization with Aβ1-42 reduces the deposits in both APP and SYN/APP mice. FIG. 6 shows synuclein deposits in the various groups of mice as detected by confocal laser scanning and light microscopy. Synuclein deposits accumulate in the SYN and SYN/APP mice treated with CFA only. However, in the same types of mice treated with Aβ1-42 and CFA there is a marked reduction in the level of synuclein deposit. These data indicate that treatment with Aβ is effective not only in clearing Aβ deposits but also in clearing deposits of synuclein. Therefore, treatment with Aβ or antibodies thereto is useful in treating not only Alzheimer's disease but combined Alzheimer's and Parkinson's disease, and Parkinson's disease in patients free of Alzheimer's disease. The titer of antiAβ antibodies in SYN/APP mice correlated with decreased formation of synuclein inclusions (r=−0.71, p<0.01).

TABLE 2

| Group | n = | Age | Treatment/Length | Ab Titers |
| --- | --- | --- | --- | --- |
| SYN | 4 | 12-20 mo | Ab inj. 50 ug/inj for 6 mo | 10,000-58,000 |
| SYN | 2 | 12-20 mo | Sal inj. for 6 mo | 0 |
| APP | 2 | 12-20 mo | Ab inj. 50 ug/inj for 6 mo | 25,000 |
| APP | 2 | 12-20 mo | Sal inj. for 6 mo | 0 |
| SYN/APP | 4 | 12-20 mo | Ab inj. 50 ug/inj for 6 mo | 1,000-50,000 |
| SYN/APP | 2 | 12-20 mo | Sal inj. for 6 mo | 0 |

Example VII

Ex Vivo Screening Assay for Activity of an Antibody Against Amyloid Deposits To examine the effect of antibodies on plaque clearance, we established an ex vivo assay in which primary microglial cells were cultured with unfixed cryostat sections of either PDAPP mouse or human AD brains. Microglial cells were obtained from the cerebral cortices of neonate DBA/2N mice (1-3 days). The cortices were mechanically dissociated in HBSS⁻ (Hanks' Balanced Salt Solution, Sigma) with 50 μg/ml DNase I (Sigma). The dissociated cells were filtered with a 100 μm cell strainer (Falcon), and centrifuged at 1000 rpm for 5 minutes. The pellet was resuspended in growth medium (high glucose DMEM, 10% FBS, 25 ng/ml rmGM-CSF), and the cells were plated at a density of 2 brains per T-75 plastic culture flask. After 7-9 days, the flasks were rotated on an orbital shaker at 200 rpm for 2 h at 37° C. The cell suspension was centrifuged at 1000 rpm and resuspended in the assay medium.

10-μm cryostat sections of PDAPP mouse or human AD brains (post-mortem interval<3 hr) were thaw mounted onto poly-lysine coated round glass coverslips and placed in wells of 24-well tissue culture plates. The coverslips were washed twice with assay medium consisting of H-SFM (Hybridoma-serum free medium, Gibco BRL) with 1% FBS, glutamine, penicillin/streptomycin, and 5 ng/ml rmGM-CSF (R&D). Control or anti-Aβ antibodies were added at a 2× concentration (5 μg/ml final) for 1 hour. The microglial cells were then seeded at a density of $0.8 \times 10^6$ cells/ml assay medium. The cultures were maintained in a humidified incubator (37° C., 5% $CO_2$) for 24 hr or more. At the end of the incubation, the cultures were fixed with 4% paraformaldehyde and permeabilized with 0.1% Triton-X100. The sections were stained with biotinylated 3D6 followed by a streptavidin/Cy3 conjugate (Jackson ImmunoResearch). The exogenous microglial cells were visualized by a nuclear stain (DAN). The cultures were observed with an inverted fluorescent microscope (Nikon, TE300) and photomicrographs were taken with a SPOT digital camera using SPOT software (Diagnostic instruments). For Western blot analysis, the cultures were extracted in 8M urea, diluted 1:1 in reducing tricine sample buffer and loaded onto a 16% tricine gel (Novex). After transfer onto immobilon, blots were exposed to 5 μg/ml of the pabAβ42 followed by an HRP-conjugated anti-mouse antibody, and developed with ECL (Amersham)

When the assay was performed with PDAPP brain sections in the presence of an antibody against a NAC marked reduction in the number and size of plaques indicative of clearing activity of the antibody was observed. An antibody to NAC was contacted with a brain tissue sample containing amyloid plaques and microglial cells, as discussed above. Rabbit serum was used as a control.

The same assay was performed with PDAPP brain sections in the presence several antibodies against Aβ. The ability of the antibodies to induce phagocytosis in the ex vivo assay and to reduce in vivo plaque burden in passive transfer studies was compared. These results show that efficacy in vivo is due to direct antibody mediated clearance of the plaques within the CNS, and that the ex vivo assay is predictive of in vivo efficacy. (See Tables 16 and 17 of Example XIV of WO 00/72880; and, Example XIV, Table 16, of WO 0072876, both of which are incorporated by reference herein for all purposes.)

Example VIII

Active Immunization with Alpha-Synuclein

A. Materials and Methods

Vaccination of hα-synuclein tg mice. For this study, heterozygous tg mice (Line D) expressing hα-synuclein under the regulatory control of the platelet-derived growth factor-β (PDGFβ) promoter (Masliah, 2000, Science 287:1265-69) were used. These animals were selected because they develop hα-synuclein immunoreactive inclusions in the brain as well as neurodegenerative and motor deficits that mimic certain aspects of LBD. Experimental animals were divided into two groups. For the first group, a total of 20 young (3 months old) tg mice were immunized for 8 months with recombinant hα-synuclein (n=10) or adjuvant alone (n=10). For the second group, a total of 20 young adult (6 months old) tg mice were immunized for 8 months with recombinant hα-synuclein (n=10) or adjuvant alone (n=10). The immunization protocol consisted first of an injection with recombinant hα-synuclein (80 μg/ml; 100 μl) with complete Freund's adjuvant (CFA). Two weeks later mice received another injection of hα-synuclein (80 μg/ml; 100 μl) with incomplete FA, followed by re-injection once a month (for the subsequent 7 months) with hα-synuclein (80 μg/ml; 100 μl) in phosphate-buffered saline. Recombinant hα-synuclein was prepared and purified as described in Masliah et al., 2005, Neuron 46:857-68, and tested for endotoxins.

Determination of antibody titers and relative affinity to hα-synuclein. hα-Synuclein antibody levels in plasma were determined using 96-well microtiter plates coated with 0.4 mg per well of purified full-length α-synuclein. The samples were incubated overnight at 4° C. followed by washing and incubation with goat anti-mouse IgG alkaline phosphatase conjugated antibody, (1:7500, Promega, Madison, Wis.). The plate was read at an excitation wavelength of 450 nm and an emission wavelength of 550 nm. Results were plotted on a semi-log graph with relative fluorescence units on the ordinate and serum dilution on the abscissa. Antibody titer was defined as the dilution at which there was a 50% reduction from the maximal antibody binding.

To determine the relative affinity for hα-synuclein by the antibodies generated in the vaccinated mice, two sets of experiments were performed. In the first, brain homogenates from non-immunized hα-synuclein tg mice were run in a minigel, multichannel apparatus (Invitrogen, Carlsbad, Calif.). Each channel was incubated with the diluted serum from each of the mice, blotted onto nitrocellulose and incubated with secondary rabbit anti-mouse antibody followed by I$^{125}$ tagged protein A (Alford et al., J. Histochem. Cytochem 42:283-287 (1994)). Blots were imaged and analyzed with the PhosphorImager (Molecular Dynamics, Piscataway, N.J.). The immunoreactive band was quantified using the ImageQuant software (Amersham Biosciences, Piscataway, N.J.). For the second set of experiments, serial vibratome sections from a non-immunized hα-synuclein tg mouse were incubated in the diluted serum from each of the treated mice followed by biotinylated horse anti-mouse IgG (1:100, Vector), Avidin D-horseradish peroxidase (HRP, 1:200, ABC Elite, Vector), and reacted with diaminobenzidine tetrahydrochloride (DAB) containing 0.001% $H_2O_2$. After microscopic examination, sections were scored according to the cellular compartment labeled (neuronal cell bodies, synapses and inclusions) and the degree of immunoreactivity (0=none; 1=very mild, 2=mild, 3=moderate, 4=intense).

Epitope mapping of hα-synuclein antibodies. The epitopes recognized by hα-synuclein antibodies were determined by an ELISA that measures the binding of an antibody to overlapping linear peptides that covered the entire hα-synuclein sequence. C-terminally biotinylated peptides with sequences of hα-synuclein (Mimotopes, San Diego, Calif.) were prepared as 15 amino acid (aa) long peptides with an overlap of 12 residues and a step of 3 residues per peptide. A total of 43 peptides were used to walk the entire 140 aa sequence of hα-synuclein with the last peptide having an overlap of 13 aa and a step of 2 aa. In addition, the last 3 peptides were repeated, but with the biotinylation occurring on the N-terminal of the peptide. This was done to improve the access to the C-terminal of the peptides by antibodies and to allow identification of free C-terminal specific antibodies. Furthermore, other features were added to this assay to allow a more thorough examination of interactions between antibodies and the non-amyloid β (Aβ) component (NAC) region (61-95) of hα-synuclein. Since the 21$^{st}$ peptide in this assay already contains the free N-terminal of the NAC region, one additional N-terminally biotinylated peptide that contains the free C-terminal of the NAC region was added to complete the assay with a total of 47 peptides.

To run the assay, these biotinylated peptides were coated down over night at 5 nM onto ELISA plates pre-coated with streptavidin (Pierce, Rockford, Ill.). The plates were then washed and serum samples, diluted to a titer equivalent of 6, were added for a 1-hour incubation. Serum samples with titers lower than 5,000 were diluted 1:1000 for this incubation. After another washing step, the bound antibodies were detected using species-specific second antibodies conjugated to HRP in a colorimetric ELISA format.

Tissue processing. Mice were euthanized and brains removed for detailed neurochemical and neuropathological analysis as described below. Briefly, the right hemibrain was frozen and homogenized for determinations of aggregated and unaggregated hα-synuclein immunoreactivity by Western blot (Masliah et al., 2000, supra). The left hemibrain was fixed in 4% paraformaldehyde (PFA) and serially sectioned with the vibratome (Leica, Wetzlar, Germany) for immunocytochemistry (ICC) and ultrastructural analysis.

Synaptosomal preparations and immunoblot analysis. To ascertain the effects of vaccination on α-synuclein accumulation in the brains of tg mice, synaptosomal fractions were prepared using sucrose gradients and analyzed by SDS-PAGE on a 10% tris-acetate polyacrylamide gel (NuPAGE™, Invitrogen). Immunoblots were probed with primary antibodies against hα-synuclein (LB509, 1:1000, Transduction Laboratories, San Diego, Calif.) and synaptophysin (1:20, Chemicon, Temecula, Calif.) and secondary goat anti-mouse IgG tagged with HRP (1:5000, SantaCruz Biotechnology, Inc., Santa Cruz, Calif.) and visualized by enhanced chemiluminescence and analyzed with a Versadoc XL imaging apparatus (BioRad, Hercules, Calif.).

Neuropathological and immunocytochemical analysis. Briefly, as previously described (Masliah et al., 2000), supra, to investigate the effects of vaccination on hα-synuclein accumulation, serially-sectioned, free-floating, blind-coded vibratome sections were incubated overnight at 4° C. with an affinity purified anti-hα synuclein specific antibody (72-10, rabbit polyclonal, 1:500) prepared as previously described (Masliah et al., 2000, supra) by immunizing rabbits with synthetic hα-synuclein peptides consisting of aa 101-124. Incubation with the primary antibody was followed by biotinylated goat anti-rabbit IgG (1:100, Vector), Avidin D-HRP (1:200, ABC Elite, Vector), and reacted with DAB tetrahydrochloride containing 0.001% $H_2O_2$. Sections were analyzed with the Quantimet 570C (Leica) in order to determine the number of hα-synuclein immunoreactive inclusions in the neocortex. For each case, three sections were analyzed and the results were averaged and expressed as numbers per sq mm. Further immunocytochemical analysis was performed by immunoreacting sections with antibodies against glial markers including CD45 (1:1000, DakoCytomation, Carpinteria, Calif.) and glial fibrillary acidic protein (GFAP, 1:500, Chemicon).

Double-immunocytochemical analysis was performed as previously described (Hashimoto et al., Neuron 32:213-223 (2001) to determine the effects of vaccination on nerve terminal density and hα-synuclein accumulation in synapses. For this purpose, vibratome sections were double-labeled with a polyclonal antibody against hα-synuclein (1:1000) and with the monoclonal antibody against synaptophysin (Chemicon). hα-Synuclein was detected with Tyramide Red (1:2000, Roche) and synaptophysin with horse anti-mouse IgG tagged with fluorescein isothiocyanate (FITC). For each case, sections were immunolabeled in duplicate and analyzed with the laser scanning confocal microscope (LSCM) and NIH Image 1.43 software to calculate the percent area of the neuropil covered by synaptophysin-immunoreactive terminals in the neocortex (Mucke et al., J. Neurosci 20:4050-4058 (2000)) and the proportion of synaptophysin-immunoreactive terminals that were hα-synuclein positive. In order to confirm the specificity of the primary antibodies, control experiments were performed where sections were incubated overnight in the absence of primary antibody (deleted), with the primary antibody preadsorbed for 48 hrs with 20-fold excess of the corresponding peptide or with preimmune serum.

All sections were processed simultaneously under the same conditions and experiments were performed twice in order to assess the reproducibility of results. Sections were imaged with a Zeiss 63X (N.A. 1.4) objective on an Axiovert 35 microscope (Zeiss, Germany) with an attached MRC1024 LSCM system (BioRad, Wattford, UK) (Masliah et al., 2000, supra).

Statistical analysis. Statistical comparisons between groups were performed utilizing the two-tailed unpaired Student's t-test. Linear regression analysis was performed to ascertain the relationship among variables. The Bonferroni correction was applied to account for multiple comparisons.

B. Results

Characterization of Antibody Titers, Affinity and Epitope Mapping

Antibody titers were analyzed at 3 time points (2 weeks, 6 months and 9 months after vaccination) in both experimental groups. Antibody titers varied considerably among mice, in animals belonging to group I, antibody titers among mice immunized with hα-synuclein ranged from 200 to 20,000 (Table 3).

TABLE 3

Summary of α-synuclein titers and immunoblot affinity (corrected for titer).

| Group | Antibody affinity by miniblot | Antibody affinity to synapses | Antibody affinity to inclusions | Antibody titers (first bleed) | Antibody titers (second bleed) | Antibody titers (third bleed) |
|---|---|---|---|---|---|---|
| Group I/α-syn | 109147 ± 2700 | 1.9 ± 0.73 | 1.2 ± 0.4 | 2332 ± 500 | 2772 ± 1176 | 3644 ± 2365 |
| Group I/CFA | 113 ± 113 | 0.4 ± 0.1 | 0 | 19 ± 6.7 | 30 ± 12 | 7 ± 4 |
| Group II/α-syn | 235747 ± 74000 | 4.1 ± 0.9 | 2.8 ± 1.0 | 3813 ± 1200 | 2926 ± 976 | 1468 ± 641 |
| Group II/CFA | 400 ± 358 | 0.3 ± 0.2 | 0.1 ± 0.1 | 23 ± 9 | 21 ± 14 | 0.6 ± 0.6 | in this group the average titers rose slightly over time. Similarly, for group II, animals immunized with hα-synuclein showed titers that ranged from 200 to 13,000 (Table 3). However, the average titer levels were higher at the first determination and then decreased over time. Immunoblotting analysis also showed significant variability from mouse to mouse in their ability to recognize hα-synuclein. Overall, levels of antibody relative affinity was higher in mice from group II compared to immunized mice from group I (Table 4).

TABLE 4

Summary of correlations between immunoblot affinity, neuropathology and titers.

| Neuropathological markers | Antibody affinity by miniblot | Antibody affinity to synapses | Antibody affinity to inclusions | Antibody affinity to neurons | Antibody titers (first bleed) |
|---|---|---|---|---|---|
| Number of α-syn (+) inclusions | −0.11 | 0.04 | 0.12 | −0.21 | 0.1 |
| % area of neuropil α-syn (+) synapses | −0.46 (p = 0.003) | −0.41 (p = 0.009) | −0.43 (p = 0.005) | 0.06 | −0.47 (p = 0.007) |
| % area of neuropil synaptophysin (+) | 0.06 | 0.35 (p = 0.04) | 0.01 | 0.04 | 0.12 |

TABLE 4-continued

Summary of correlations between immunoblot affinity, neuropathology and titers.

| Neuropathological markers | Antibody affinity by miniblot | Antibody affinity to synapses | Antibody affinity to inclusions | Antibody affinity to neurons | Antibody titers (first bleed) |
|---|---|---|---|---|---|
| synapses Antibody affinity by miniblot | — | 0.74 (p = 0.0001) | 0.70 (p = 0.0001) | −0.16 | 0.85 (p = 0.0001) |
| Antibody titers (first bleed) | 0.85 (p = 0.0001) | 0.62 (p = 0.0001) | −0.18 | 0.81 (p = 0.0001) | — |

By ICC, sera from mice vaccinated with hα-synuclein showed labeling of neurons, intraneuronal inclusions and presynaptic terminals. In contrast, mice treated with adjuvant alone showed diffuse and non-specific mild staining of cell bodies). Sera from mice belonging to group II showed higher affinity in recognizing hα-synuclein in the synapses and neurons in the tg mice compared to immunized mice from group I (Table 4).

Epitope mapping studies showed that in mice vaccinated with hα-synuclein, antibodies most frequently recognized peptide epitopes within the C-terminus region of hα-synuclein (FIG. 8). In addition, antibodies to additional epitopes were also occasionally recognized. In contrast, no reactivity or antibody epitopes were detected with the sera of mice treated with CFA alone.

Figure 9:
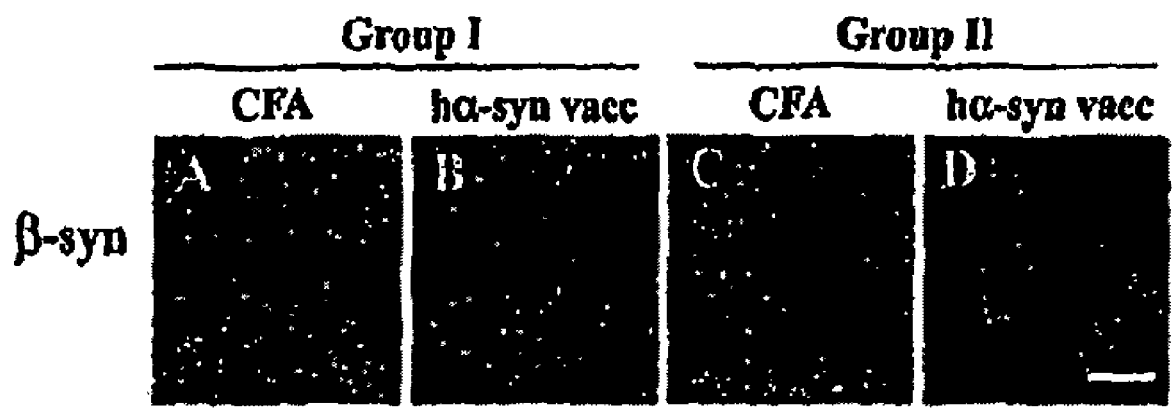
FIG. 9 shows image analysis of the levels of human α-synuclein immunoreactivity and other markers of neurodegeneration. (A) Mean number of hα-synuclein positive inclusions in the temporal cortex. Vaccination with human α-synuclein resulted in a significant decrease in the number of inclusions compared to controls. This effect was more pronounced in mice from group II as opposed to group I. (B) Percent area of the neuropil occupied by synaptophysin-immunoreactive terminals in the frontal cortex. In transgenic (tg) mice treated with CFA alone, the number of synaptophysin immunolabeled terminals decreased by 20%, whereas the levels of synaptophysin immunoreactivity per synapse was unchanged. (C) Levels of CD45 immunoreactivity (microglial marker) in the temporal cortex were slightly higher in the brains of human α-synuclein vaccinated mice. (D) Percent area of the neuropil of occupied by human α-synuclein immunoreactive terminals in the temporal cortex. In tg mice vaccinated with human α-synuclein, there was a decrease in the accumulation of α-synuclein in synaptophysin-immunoreactive terminals. *=significant difference compared to human α-synuclein tg mice treated with CFA alone (p<0.05, student's T test).

Immunization Reduces hα-Synuclein Accumulation and Preserves Synaptic Density in the Brains of tg Mice To determine the effects of immunotherapy on hα-synuclein accumulation, sections were labeled with antibodies against hα-synuclein and analyzed by bright field microscopy or by LSCM. In tg mice, abundant hα-synuclein immunoreactivity was observed in the neuropil as well as in intraneuronal inclusions. Compared to tg mice treated with CFA alone, mice from both of the immunized groups showed a comparable reduction (approximately 25%) in the number of inclusions in the temporal cortex (FIG. 9A). Moreover, immunization resulted in a decrease in hα-synuclein immunoreactivity in the neuropil. When compared to tg mice treated with CFA alone, this effect was greater in mice from group II than in mice from group I (FIG. 9A). To determine if the immunization effects were indeed related to the antibodies' ability to reduce neuronal hα-synuclein accumulation or to masking effects, control experiments were performed by comparing the levels of β synuclein immunoreactivity between CFA alone and hα-synuclein vaccinated tg mice. Consistent with the known distribution of β synuclein, a close homologue to α-synuclein (Iwai et al., Neuron 14:467-475 (1994)), abundant β-synuclein immunoreactivity was observed in the neuropil in association with the presynaptic terminals and mild immunolabeling was detected in the neuronal cell bodies, but not in the inclusions. Compared to tg mice treated with CFA alone, no differences in the patterns and levels of β-synuclein were found in mice immunized with hα-synuclein. To further investigate the specificity of the effects of the hα-synuclein antibodies, levels of murine (m) α synuclein immunoreactivity were compared between the CFA alone and hα-synuclein vaccinated tg mice. Similar to h αsynuclein, mαsynuclein immunoreactivity was abundant in the neuropil in association with nerve terminals but was absent in the neuronal cell bodies and in the inclusions. Both in the CFA and hα-synuclein immunized mice, patterns and levels of mαsynuclein were comparable. Taken together, these studies suggest that vaccination specifically affects hα-synuclein but not other related synaptic molecules.

To further ascertain the effects of the immunotherapy on neuropil integrity, sections were immunostained with an antibody against synaptophysin or by electron microscopy. Compared to non-transgenic (nontg) mice, tg mice treated with CFA alone showed an average of 20% decrease in the number of synaptophysin immunolabeled terminals, and levels of synaptophysin immunoreactivity per synapse remained unchanged (FIG. 9B). In contrast, immunized mice from both groups showed levels of synaptophysin immunoreactivity comparable to nontg controls (9B). Further immunocytochemical analysis with antibodies against glial markers such as GFAP and CD45 showed a trend toward increased immunoreactivity in the brains of tg mice vaccinated with hα-synuclein (FIG. 9C). Consistent with these findings, ultrastructural analysis showed that in the brains of tg mice immunized with hα-synuclein, the neuropil was well preserved, with intact presynaptic terminals and dendrites and the nerve terminals contained abundant clear vesicles and formed postsynaptic densities. Only occasional electrodense aggregates were identified in the neuritic processes and overall the mitochondria and myelin were well preserved.

To better characterize the effects of vaccination on hα-synuclein aggregation in the synapses, double immunocytochemical and Western blot analysis with synaptosomal preparations was performed. Under physiological conditions hα-synuclein is localized primarily to the presynaptic boutons (Iwai et al., 1994, supra) and in LBD and in the tg mice, increased accumulation of hα-synuclein in the synapses is associated with functional deficits and synapse loss (Hashimoto et al., 2001, supra). To ascertain the effects of vaccination on hα-synuclein accumulation in the nerve terminals, double immunolabeling studies with antibodies against the presynaptic terminal marker synaptophysin and hα-synuclein and WB analysis with synaptosomal preparations were performed. Confocal imaging of double-labeled sections showed that in comparison to hα-synuclein tg mice vaccinated with CFA alone (FIG. 9D), those that were injected with hα-synuclein displayed decreased accumulation of hα-synuclein in synaptophysin-immunoreactive nerve terminals in the neocortex (FIG. 9D).

Figure 10:
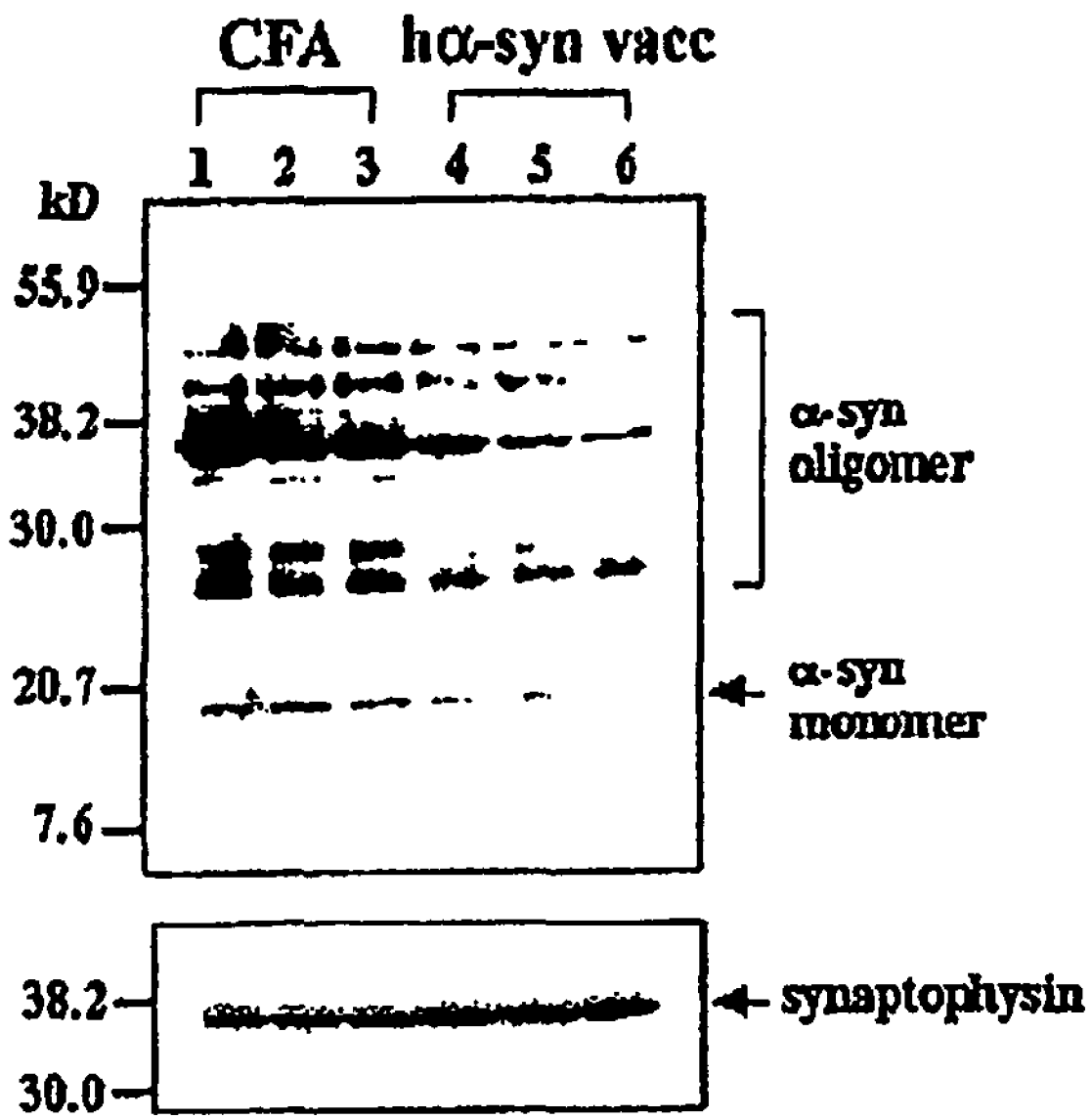
FIG. 10 shows Western blot analysis of the levels of human α-synuclein and synaptophysin immunoreactivity in vaccinated animals. Compared to brains of tg mice treated with CFA alone (lanes 1-3), in hα-synuclein vaccinated tg mice (lanes 4-6), levels of both human α-synuclein oligomers and monomers were decreased (upper panel), whereas levels of synaptophysin immunoreactivity increased in the latter group (lower panel).

Consistent with the immunocytochemical studies, immunoblot analysis showed that in the tg mice treated with CFA alone, there were abundant higher molecular weight bands, possibly reflecting the accumulation of hα-synuclein immunoreactive inclusions in the synapses (FIG. 10). In the immunized mice there was a considerable decrease in the accumulation of higher molecular weight bands of hα-synuclein and the native band, but no effects were observed on the levels of mα-synuclein. Furthermore, compared to tg mice treated with CFA alone, levels of synaptophysin immunoreactivity were higher in the synaptosomal preparations from immunized mice (FIG. 10). Taken together, these results suggest that immunotherapy can ameliorate the neuronal damage in the brains of tg mice by reducing the accumulation of potentially toxic hα-synuclein oligomers in the synapses.

The Effects of Immunization are Dependent on the Relative Affinity of Antibodies to Recognize Synaptic Terminals To better understand which factors predict the effectiveness of the immunotherapy, linear regression analysis was performed between the neuropathological markers of hα-synuclein accumulation and the antibody titers and affinity. This analysis showed a significant correlation between relative antibody affinity by immunoblot and levels of hα-synuclein immunoreactivity in the synapses but not with the numbers of neuronal inclusions. Similarly, relative antibody affinity to recognize synapses by ICC was inversely correlated with levels of hα-synuclein in the synapses and directly correlated with the percent area occupied by synaptophysin-labeled nerve terminals, but not with the numbers of neuronal inclusions. Levels of antibody reactivity by immunoblot and ICC were strongly correlated with antibody titers as determined by ELISA. Antibody titers were also correlated with the percent area of the neuropil labeled with the anti-hαsynuclein antibody but not with the numbers of inclusions in neurons (Table 4). Taken together, these results suggest that the relative immunoblot reactivity of the anti-human α-synuclein antibodies and to some extent the antibodies' ELISA titers correlate with the reduction of neuronal human α-synuclein accumulation.

The Anti-human α-synuclein Antibodies are Internalized and Bind to Synapses and Inclusion-containing Neurons in tg Mice To determine if trafficking antibodies recognize the characteristic neuronal sites where human α-synuclein accumulates in the brains of tg mice, single and double immunocytochemical analysis was performed with horse anti-mouse IgG antibodies. These antibodies putatively recognize the anti-human α-synuclein generated in the immunized animals but not in the CFA controls. Bright field digital microscopy of the immunolabeled sections showed that in mice immunized with hα-synuclein, the biotinylated anti-mouse IgG diffusely labeled neuronal cell bodies and neuritic processes in the neuropil. In tg animals treated with CFA alone there was mild labeling of blood vessels and occasional cells resembling microglia. Double immunostaining experiments confirmed that in the vaccinated mice, neuronal cell bodies labeled by a FITC tagged anti-mouse IgG displayed hα-synuclein immunoreactivity. Compared to tg mice treated with CFA alone, in hα-synuclein vaccinated mice, in some neurons, the anti-mouse IgG and the hα-synuclein immunoreactivity were co-localized in the periphery of the cell bodies, in other areas the two labels were detected in the neuritic processes and synapses. Moreover, in several human α-synuclein containing neurons the two markers were detected in granular subcellular structures averaging in size 0.4-0.8 μm in diameter. Additional double labeling experiments showed that these granular structures displayed cathepsin D immunoreactivity, suggesting that the internalized anti-human α-synuclein antibodies reacted with synuclein within lysosomes. Consistent with this finding, ultrastructural analysis showed that in some of the neurons of the human α-synuclein vaccinated mice, electrodense laminated structures suggestive of lysosomes and phagolysosomes were identified. Taken together, these results suggest that vaccination with human α-synuclein can promote degradation of this molecule via activation of a lysosomal pathway.

Example IX

Figure 11:
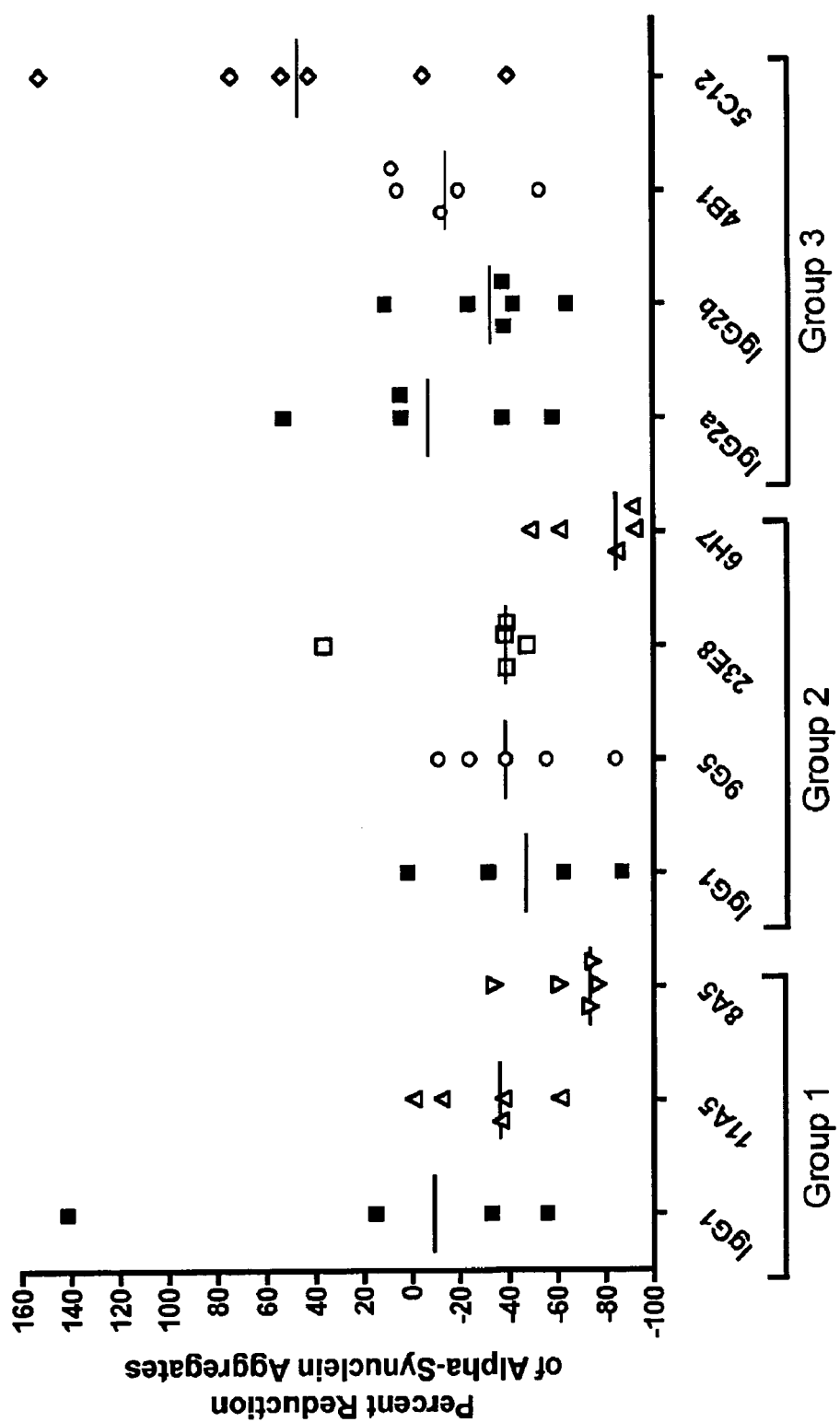
FIG. 11 shows analysis of intraneuronal α-synuclein aggregates after intracerebral injection of anti-α-synuclein antibodies. The C-terminal antibody 8A5 and the N-terminal antibody 6H7 had a clearing effect. IgG1, IgG2a, and IgG2b were isotype controls. Horizontal bars represent the median.

Clearance of α-Synuclein Aggregates In Vivo by Administration of α-Synuclein Antibodies This example demonstrates clearance of intraneuronal α-synuclein aggregates using monoclonal anti-α-synuclein antibodies that recognize the α-synuclein termini. The monoclonal antibodies were injected into the neocortex of transgenic mice that overexpress human α-synuclein and have intraneuronal α-synuclein aggregates. The two antibodies, one directed against the N-terminus and the other directed against the C-terminus of α-synuclein, reduced the number of intraneuronal α-synuclein aggregates by up to 80% compared to irrelevant control antibodies (FIG. 11).

Methods. Monoclonal antibodies recognizing different epitopes of the α-synuclein molecule and irrelevant, isotype-matched control antibodies were dissolved in sterile phosphate-buffered-saline solution (Table 5) for injection into mice. The animals used were 4 to 8 month-old heterozygous transgenic mice overexpressing human wildtype α-synuclein in the brain under the transcriptional control of the PDGF promoter. From 4 to 6 different transgenic mice were used for each of the antibodies.

TABLE 5

α-Synuclein Antibodies and Controls Used for Intracerebral Injection in a Transgenic Model of Neuronal Synucleopathy.

| Monoclonal antibody | Epitope/Specificity | Isotype |
|---|---|---|
| 11A5 | α-synuclein phospoSER129 | IgG1 |
| 8A5 | α-synuclein C-terminus | IgG1 |
| 9G5 | α-synuclein 91-96 | IgG1 |
| 23E8 | α-synuclein 40-55 | IgG1 |
| 6H7 | α-synuclein N-terminus | IgG1 |
| 4B1 | α-synuclein C-terminus | IgG2a |
| 5C12 | α-synuclein 109-120 | IgG2b |
| 27-1 | control | IgG1 |
| TY11-15 | control | IgG2a |
| 5B7 | control | IgG2b |

For each mouse, 2 μl of a 2 mg/ml antibody solution were injected stereotactically under anesthesia into the deep layers of the parietal neocortex of the right brain hemisphere (ipsilateral side). The left hemispheres (contralateral side) served as an baseline control for each mouse. Injection sites were sutured and mice were monitored until they recovered from anesthesia. The investigator performing the injections was blinded as to which antibody was injected each time. Two weeks after injection, mice were euthanized following institutional guidelines. Their brains were removed, fixed in 4% paraformaldehyde for 48 h, and cut coronally at 40 μm thickness using a Leica vibratome. Two sections per animal (around the injection site) were stained by immunoperoxidase staining with a polyclonal α-synuclein antibody (ELADW-47, recognizing α-synuclein amino acids 115-122). For each section, intraneuronal α-synuclein aggregates were counted in 4 microscopic fields (20× objective) around the injection site in the ipsilateral hemisphere, and in 4 fields corresponding fields in the contralateral control hemisphere. The α-synuclein aggregate counts for two sections were summed for each hemisphere. Finally, for each animal the difference between the total α-synuclein aggregate count between the two hemisphere was calculated and expressed as % difference between the contralateral and the ipsilateral hemisphere, thus providing a measure of the effect of α-synuclein antibodies on aggregate clearance for each individual mouse. Sections were blind-coded and the code was broken when analysis was complete.

The mice can be categorized into three groups based on which antibodies were injected:

Group 1: Mice injected with 11A5, 8A5 or an IgG$_1$ control.

Group 2: Mice injected with 9G5, 23E8, 6H7, or an IgG$_1$ control.

Group 3: Mice injected with 4B1, 5C12, an IgG$_{2a}$ or an IgG$_{2b}$ control.

Figure 12:
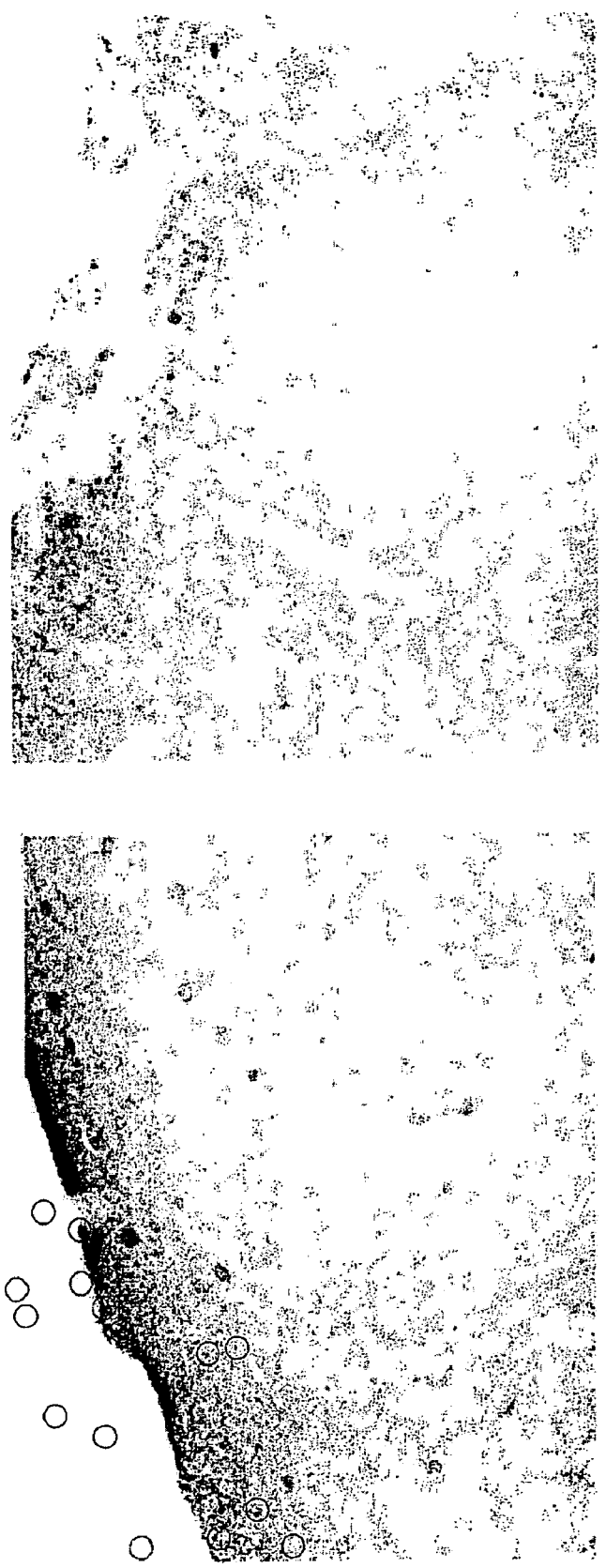
FIG. 12 shows sections of the contralateral side (left panel; round brown dots inside section are α-synuclein aggregates) and ipsilateral side (right panel) of a mouse injected with monoclonal antibody 8A5. Immunostaining was performed with a polyclonal antibody for α-synuclein. Intraneuronal α-synuclein aggregates in the contralateral side are circled.

Results. The results of the study are shown in FIGS. 11 and 12. Intraneuronal α-synuclein aggregates were cleared by two monoclonal antibodies: 8A5 (also called JH4.8A5) and 6H7 (also called JH17.6H7), both described in PCT patent publication WO 05047860A2 ("Antibodies to Alpha-Synuclein" filed May 26, 2005) and in copending patent application Ser. No. 10/984,192, both of which are incorporated by reference. MAb 6H7 was raised against recombinant human α-synuclein expressed in *E. coli* and recognizes the amino-terminus of human and mouse α-synucleins. It recognizes an epitope that includes the first three amino acids of α-synuclein. MAb 6H7 is able to recognize fusion proteins of synuclein in which the tag protein is fused to the N-terminus of synuclein, suggesting a free-amino terminus is not required (though it may be preferred). MAb 8A5 was raised against purified bovine synucleins (mixture of α and β) and recognizes an epitope at the carboxy-terminus of human and mouse α-synucleins. MAb 8A5 can bind truncated synuclein terminating at amino acid 139. Preliminary experiments suggest 8A5 has a 4-5 fold preference for synuclein with a free C-terminus compared to a C-terminus conjugated to biotin. Both mAb 6H7 and mAb 8A5 also recognize beta-synuclein. MAb 4B1 recognizes the C-terminal region of synuclein and binds synuclein on western blots, but does not recognize synuclein in solution (i.e., mAb 4B1 does not immunoprecipitate synuclein). FIG. 12 shows sections of the contralateral side (left panel; round brown dots inside section are α-synuclein aggregates) and ipsilateral side (right panel) of a mouse injected with 8A5. The difference between the 8A5-injected mice and the IgG$_1$-injected controls was statistically significant ($p<0.05$ by non-parametric Kruskall-Wallis followed by Dunn's post-hoc test). These results indicate that targeting the α-synuclein C-terminus and/or the N-terminus is therapeutically beneficial in synucleopathies such as PD and DLB. Administration of other anti-α-synuclein antibodies tested (Table 5, FIG. 11) did not result in clearing of aggregates.

Example X

Clearance of α-Synuclein Aggregates In Vivo by Administration of α-Synuclein Antibodies This example demonstrates clearance of intraneuronal α-synuclein aggregates using monoclonal anti-α-synuclein antibodies that recognize the α-synuclein termini (6H7 and 8A5) as described in Example IX. This example also demonstrates clearance of intraneuronal α-synuclein aggregates using a monoclonal anti-α-synuclein antibody that recognizes an epitope near the C-terminus (9E4). mAb 9E4 recognizes an epitope of alpha-synuclein in the region of amino acids 118-126.

Figure 13:
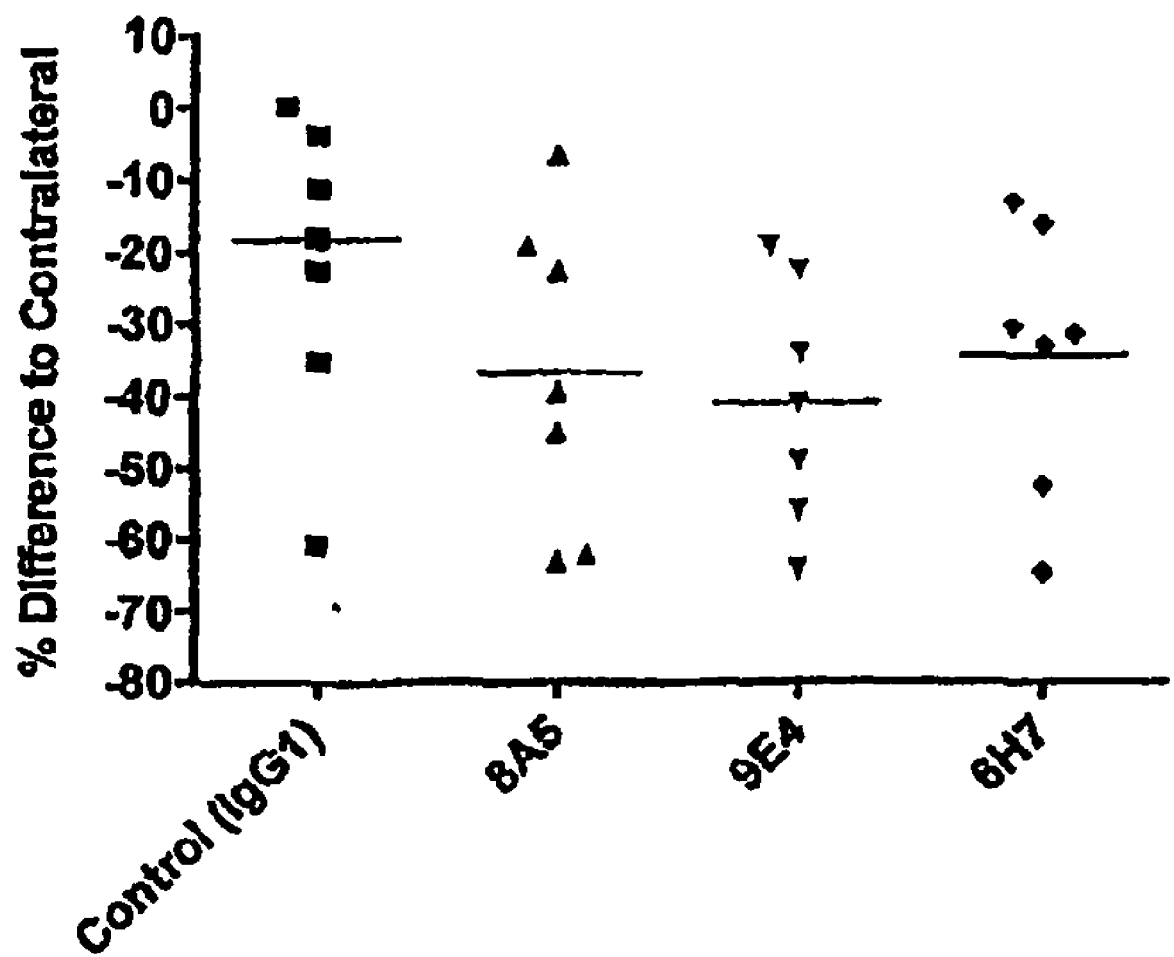
FIG. 13 shows clearance of intraneuronal α-synuclein aggregates in the neocortex of transgenic mice overexpressing human α-synuclein by anti-α-synuclein monoclonal antibodies 8A5, 9E4, and 6H7.

The monoclonal antibodies were injected 3× in the neocortex of the right hemisphere of transgenic mice that overexpress human α-synuclein and form intraneuronal α-synuclein aggregates. As described above, mAb 6H7, which recognizes the N-terminus of α-synuclein and mAb 8A5, which recognizes the C-terminus of α-synuclein, reduced the number of intraneuronal α-synuclein aggregates by up to 80% compared to an irrelevant control antibody (FIG. 13). In addition, mAb 9E4, which recognizes an α-synuclein epitope at aa118-126, had a similar α-synuclein aggregate-reducing effect (FIG. 13).

Methods. Monoclonal antibodies recognizing different epitopes of the α-synuclein molecule and an irrelevant, isotype-matched control antibody were dissolved in sterile phosphate-buffered-saline solution for injection into mice (Table 6). The animals used were 4 to 8 month-old heterozygous transgenic mice overexpressing human wildtype α-synuclein in the brain under the transcriptional control of the PDGF promoter. From 4 to 6 different transgenic mice were used for each of the antibodies.

TABLE 6

α-Synuclein Antibodies and Controls Used for 3 Intracerebral Injection in a Transgenic Model of Neuronal Synucleopathy.

| Monoclonal antibody | Epitope | Isotype |
| --- | --- | --- |
| 8A5 | α-synuclein C-terminus | IgG1 |
| 6H7 | α-synuclein N-terminus | IgG1 |
| 9E4 | α-synuclein aa118-126 | IgG1 |
| 27/1 | control | IgG1 |

For each mouse, 2 μl of a 2 mg/ml antibody solution were injected for each injection site stereotactically under anesthesia into the deep layers of the parietal neocortex of the right brain hemisphere (ipsilateral side). The left hemispheres (contralateral side) served as an baseline control for each mouse. The three stereotactic injection coordinates were: injection 1: 2.0 mm Bregma, 1.5 mm Lateral, 2.0 mm Depth; injection 2: 0.4 mm Bregma, 1.5 mm Lateral, 1.4 mm Depth; injection 3: −2.3 mm Bregma, 1.5 mm Lateral, 1.2 mm Depth). Injection sites were sutured and mice were monitored until they recovered from anesthesia. The investigator performing the injections was blinded as to which antibody was injected each time. Two weeks after injection, mice were euthanized following institutional guidelines. Their brains were removed, fixed in 4% paraformaldehyde for 48 h, and cut coronally at 40 μm thickness using a Leica vibratome. Every third section throughout the brain for each animal was stained by immunoperoxidase staining with a polyclonal α-synuclein antibody (ELADW-47, recognizing α-synuclein amino acids 115-122). Based on location for each injection site, two-four sections around each of the three injection site were selected for each animal. Intraneuronal α-synuclein aggregates were counted in 4 microscopic fields (20× objective) around the injection site in the ipsilateral hemisphere, and in 4 fields corresponding fields in the contralateral control hemisphere. The α-synuclein aggregate counts for all sections counted (3-12 sections total/animal) were summed for each hemisphere. Finally, for each animal the difference between the total α-synuclein aggregate count between the two hemisphere was calculated and expressed as % difference between the contralateral and the ipsilateral hemisphere, thus providing a measure of the effect of α-synuclein antibodies on aggregate clearance for each individual mouse. Sections were blind-coded and the code was broken when analysis was complete.

Example XI

Figure 14:
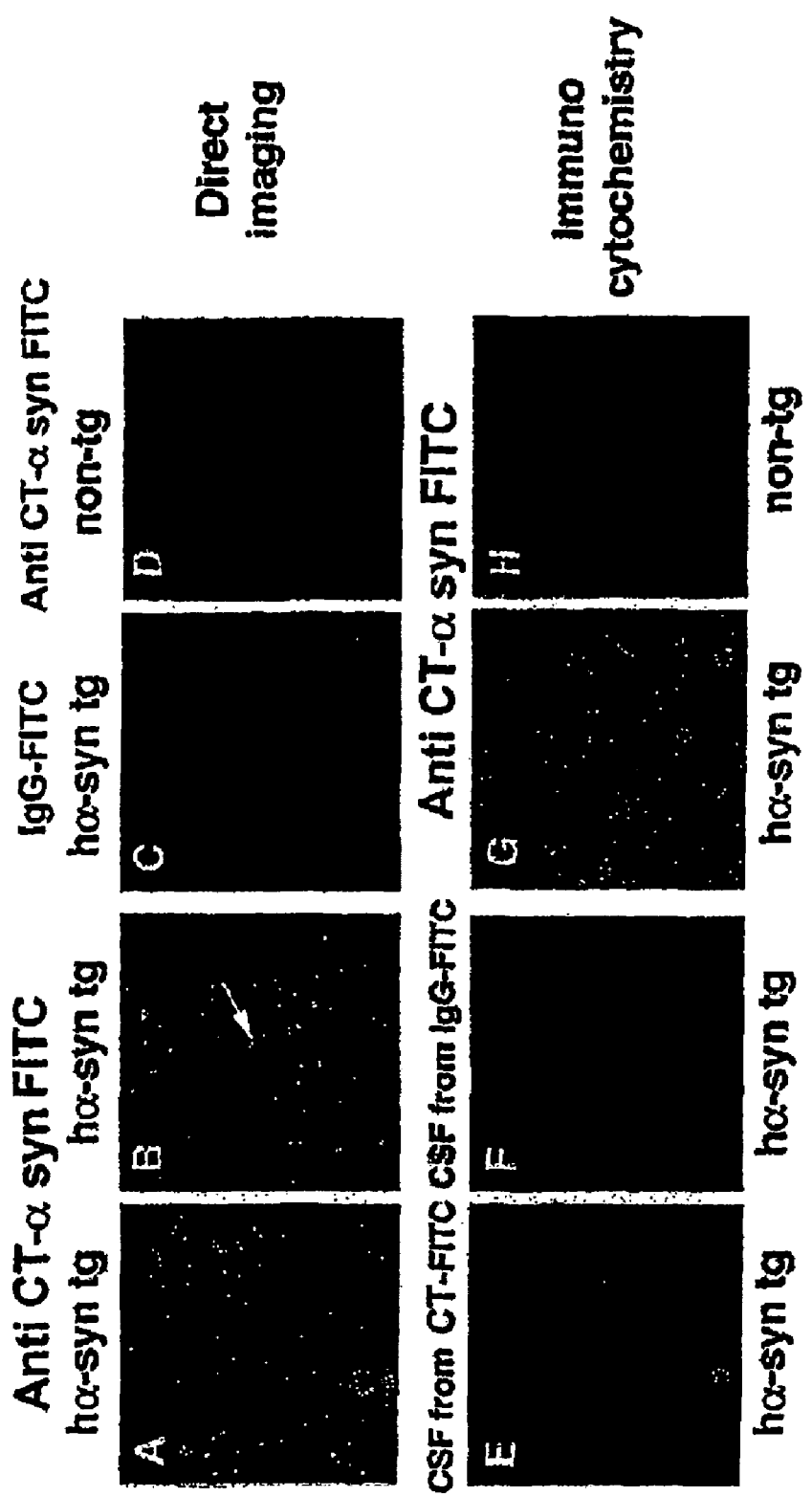
FIG. 14 shows aggregation of α-synuclein in the membrane and localization of α-synuclein to lysozomes in human α-synuclein mice after a single intravenous injection with 9E4-FITC.

A Monoclonal Antibody Against the C-terminus of Alpha-synuclein Enters the Brain and Recognizes Alpha-synuclein Human α-syn tg mice were intravenously injected with 9E4-FITC at a dosage of 5 mg/kg; 100 μl. The mice were euthanized one week later to determine the presence of the antibody in the brain and CSF. We visualized the fluorescent antibody directly, and found that the antibody did, in fact, traffic into the brain and specifically recognized asyn in the neuronal cell body and synapses. A peripherally-delivered control IgG showed only background immunoreactivity in both tg and nontg mice. Furthermore, we found that CSF from treated mice was immunoreactive against asyn in the brains of untreated tg mice, and showed a pattern of staining similar to direct immunolabeling with the 9E4-FITC antibody. (See FIG. 14.)

Example XII

Figure 15:
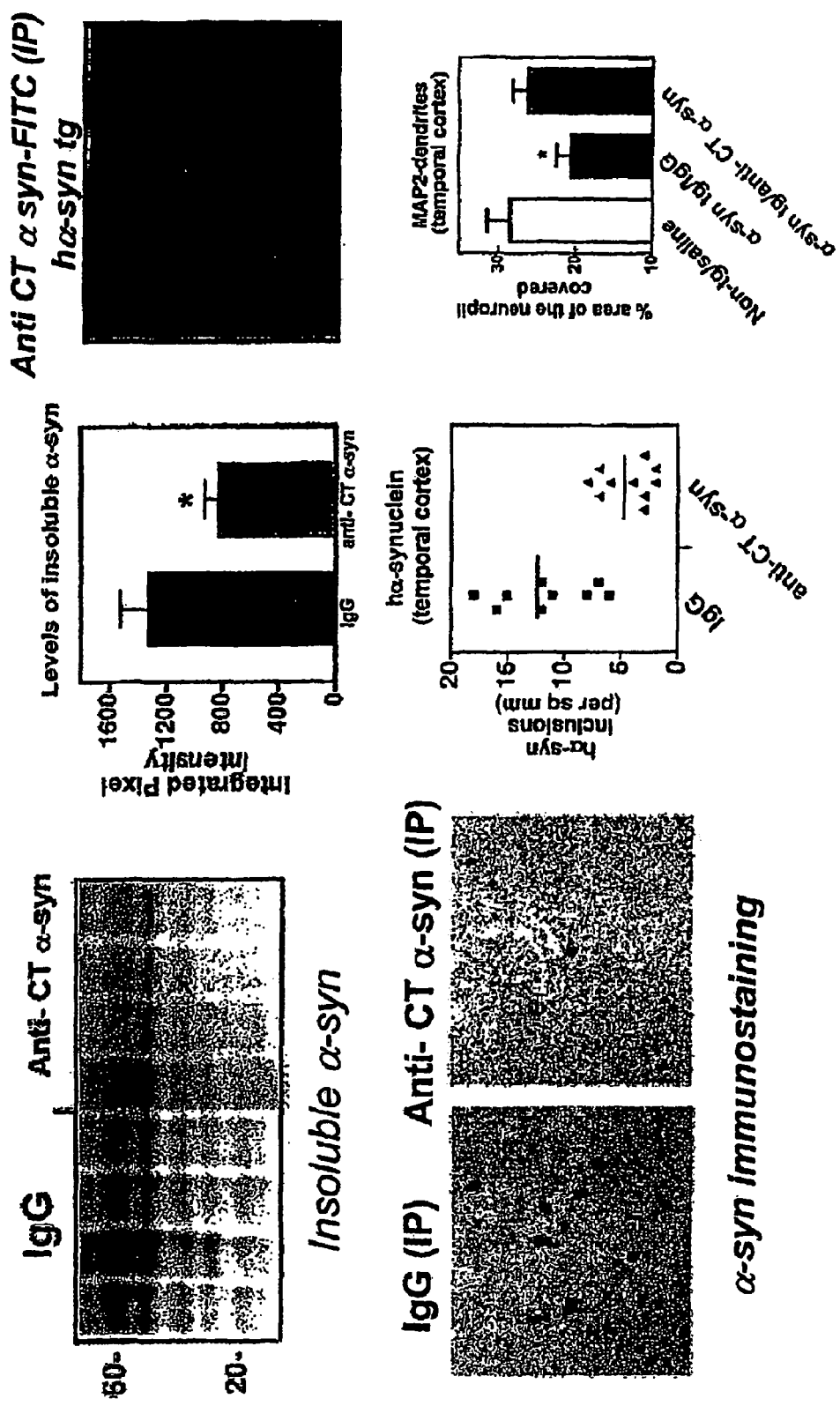
FIG. 15 shows reduced levels of α-syn oligomers and insoluble forms of α-syn were found in the brains of tg mice injected intraperitoneally with 9E4 at a dosage of 1 mg/kg for six months.

Passive Immunization with an Antibody Against C-terminal α-Syn Reduces α-syn Deficits in tg Mice The objective of the present study was to show passive immunization with an antibody against α-syn C-terminus traffics into the CNS and is capable of recognizing and clearing α-syn aggregates in the brain of tg mice. For this purpose human α-syn tg mice were injected intraperitoneally with 9E4 at a dosage of 1 mg/kg for six months. Animals treated with 9E4 were euthanized after 6 months of weekly injections. Reduced levels of α-syn oligomers and insoluble forms of α-syn were found in the brains of injected tg mice. (See FIG. 15.)

Example XIII

Immunization with an Antibody Against the C-terminus of α-synuclein Promotes Clearance Via Activation of the Autophagy Pathway in a transgenic of Parkinson's Disease A monoclonal antibody (clone 9E4) tagged with FITC was injected IV in nontg and alpha-syn tg mice. After 3 days post injection low levels of the antibody were detected in the brain, while high levels were detected in plasma. At 14 and 30 days post injection higher levels were detected in the brain with decreasing levels in the plasma as evidenced both by immunocytochemistry and ELISA. In the brains of tg mice, the 9E4-FITC antibody was detected in association with granular α-syn aggregates in neurons. These aggregates were co-labeled with antibodies against lysosomal markers (cathepsin D). Control experiments with a non-immune IgG-FITC show only background labeling in nontg and alpha-syn tg mice. Moreover, immunolabeling of sections from alpha-syn tg mice with the CSF of mice treated with 9E4-FITC immunolabeled synapses and neurons in sections from untreated alpha-syn tg mice, in contrast no labeling was observed with the CSF of mice treated with non-immune IgG-FITC.

Figure 16:
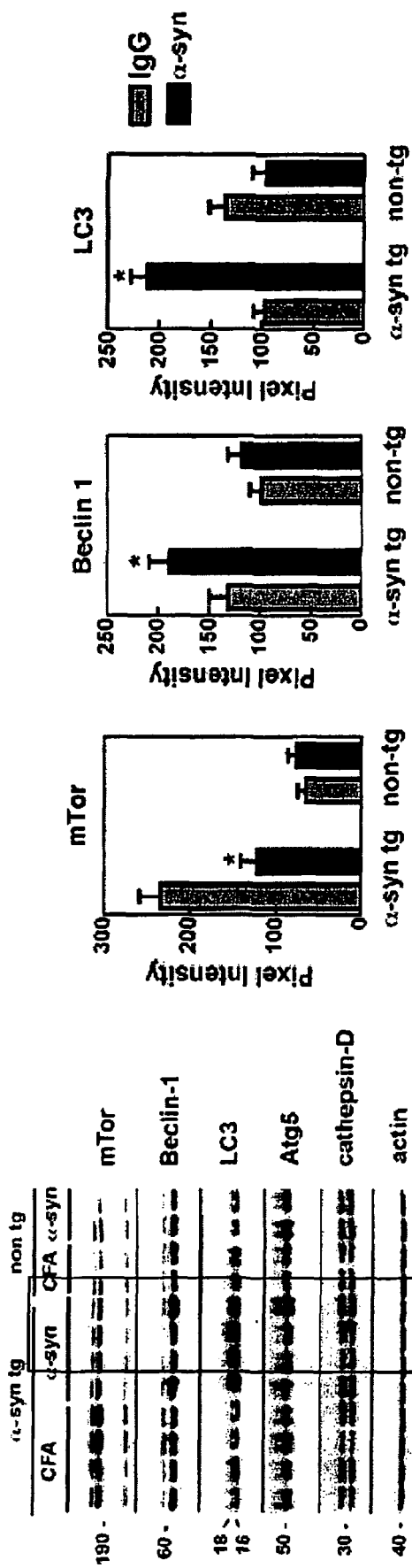
FIG. 16 shows levels of beclin-1, LC3 cleavage and Atg5 were increased and co-localized with the α-syn aggregates in the neurons of immunized tg mice.
Figure 17:
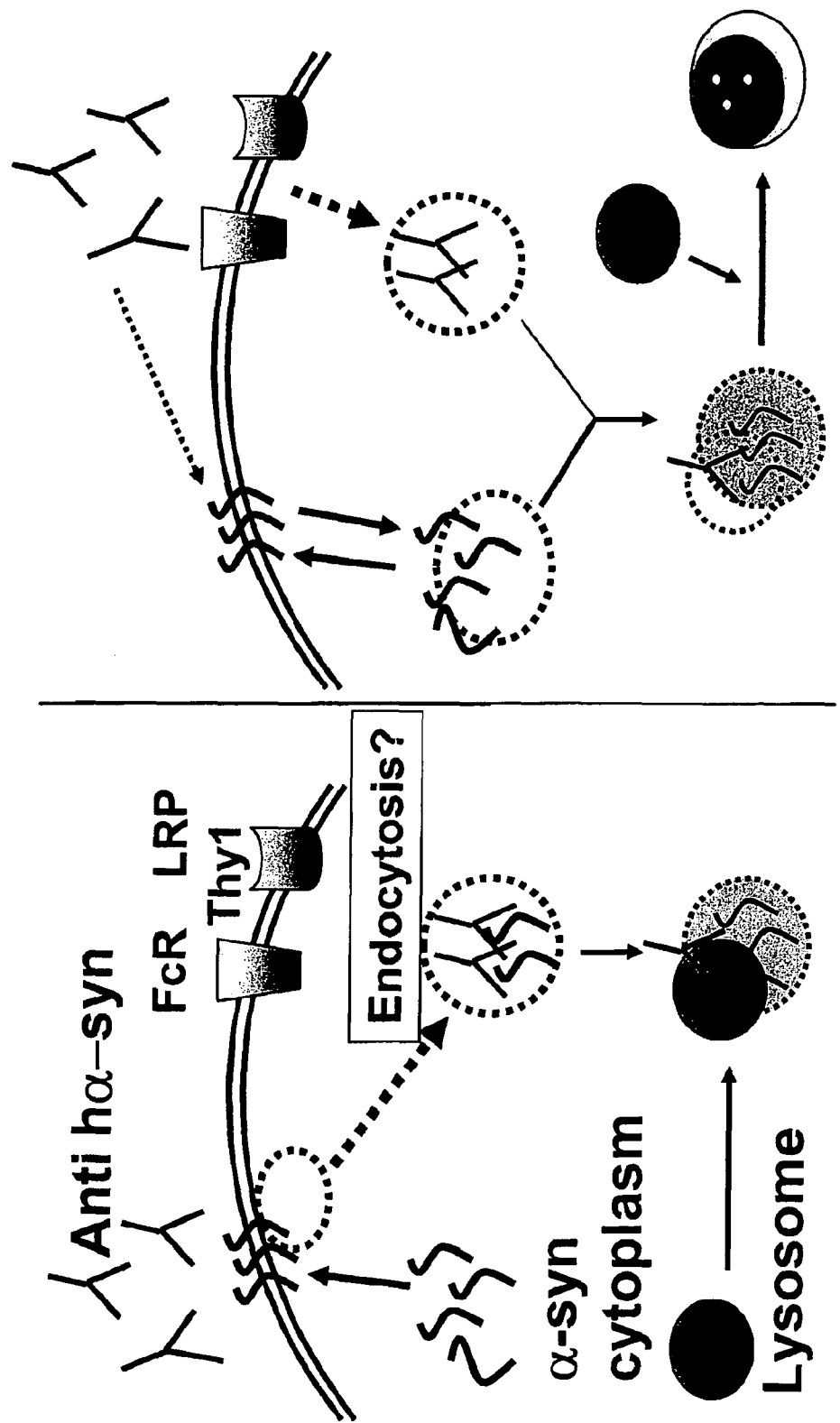
FIG. 17 shows how an antibody against an epitope at or near the c-terminus of α-syn traffics into the CNS, recognizes aggregates in affected neurons and triggers clearance via a lysosomal pathway, such as autophagy.

Clearance of alpha-syn in the tg mice immunized with 9E4 was probably related to activation of the autophagy pathway because levels of beclin-1, LC3 cleavage and Atg5 were increased and co-localized with the α-syn aggregates in the neurons of immunized tg mice. (See FIG. 16.) These results suggest that a monoclonal antibody against an epitope at or near the c-terminus of α-syn traffics into the CNS, recognizes aggregates in affected neurons and t triggers clearance via a lysosomal pathway, such as autophagy. FIG. 17 illustrates such pathways. In the left of the figure, the antibody binds to membrane-bound alpha synuclein from outside the cells, and the resulting complex is endocytosed and combines with a lysosome inside the cell forming an autophagosome and triggering degradation by lysosomal enzymes. In the right of the figure, alpha-synuclein and the antibody to alpha-synuclein are separately endocytosed, the antibody likely gaining entry via Fc receptors, and combined with a lysosome in the cell, followed by lysosomal degradation.

Deposit

The following monoclonal antibody-producing cell lines have been deposited under the provisions of the Budapest Treaty with the American Type Culture Collection (ATCC, P.O. Box 1549, Manassas, Va. 20108) on the dates indicated:

| Monoclonal antibody | Cell Line | Epitope/Specificity | Isotype | Date of Deposit | Accession No. |
|---|---|---|---|---|---|
| 11A5 | JH22.11A5.6.29.70.54.16.14 | alpha-synuclein residues 124-134 phospoSER129 | IgG1 | Feb. 26, 2007 | PTA-8222 |
| 8A5 | JH4.8A5.25.7.36 | alpha-synuclein C-terminus | IgG1 | Aug. 4, 2005 | PTA-6909 |
| 1H7 | JH17.1H7.4.24.34 | alpha-synuclein residues 91-99 | IgG1 | Feb. 26, 2007 | PTA-8220 |
| 9E4 | JH17.9E4.3.37.1.14.2 | alpha-synuclein residues 118-126 | IgG1 | Feb. 26, 2007 | PTA-8221 |
| 6H7 | JH17.6H7.1.54.28 | alpha-synuclein N-terminus | IgG1 | Aug. 4, 2005 | PTA-6910 |

It will be apparent to one of ordinary skill in the art that many changes and modifications can be made thereto without departing from the spirit or scope of the appended claims. Unless otherwise apparent from the context, any step, feature, embodiment, or aspect can be used in combination with any other. All publications and patent applications mentioned in this specification are herein incorporated by reference to the same extent as if each individual publication or patent application was specifically and individually indicated to be incorporated by reference.

What is claimed is:

1. A method of treating, reducing the risk of, lessening the severity of, or delaying the outset of a disease characterized by Lewy bodies or alpha-synuclein aggregation in the brain, the method comprising administering to a patient having or at risk of the disease an effective regime of an antibody that specifically binds to human alpha-synuclein (SEQ ID:1), wherein the antibody is 1H7 (ATCC accession number PTA-8220) or a humanized or chimeric form thereof.

2. The method of claim 1, wherein the antibody is an antibody of human IgG1 isotype.

3. The method of claim 1, wherein the antibody has the CDRs of antibody 1H7 as defined by Kabat.

4. The method of claim 1, wherein the antibody has the CDRs of antibody 1H7 as defined by Chothia.

* * * * *